(12) United States Patent
Papadopoulos et al.

(10) Patent No.: US 12,324,839 B2
(45) Date of Patent: Jun. 10, 2025

(54) TESTOSTERONE-INDUCING PEPTIDE COMPOUNDS AND ASSOCIATED COMBINATIONS

(71) Applicant: THE ROYAL INSTITUTION FOR THE ADVANCEMENT OF LEARNING/MCGILL UNIVERSITY, Montreal (CA)

(72) Inventors: Vassilios Papadopoulos, Pasadena, CA (US); Daniel Benjamin Martinez-Arguelles, Ottawa (CA)

(73) Assignee: ACESIS BIOMED US, INC., Centennial, CO (US)

( * ) Notice: Subject to any disclaimer, the term of this patent is extended or adjusted under 35 U.S.C. 154(b) by 380 days.

(21) Appl. No.: 17/291,328

(22) PCT Filed: Nov. 4, 2019

(86) PCT No.: PCT/CA2019/051559
§ 371 (c)(1),
(2) Date: May 5, 2021

(87) PCT Pub. No.: WO2020/093142
PCT Pub. Date: May 14, 2020

(65) Prior Publication Data
US 2022/0387606 A1    Dec. 8, 2022

Related U.S. Application Data

(60) Provisional application No. 62/756,767, filed on Nov. 7, 2018.

(51) Int. Cl.
| A61K 47/60 | (2017.01) |
| A61K 47/54 | (2017.01) |
| A61P 5/26  | (2006.01) |

(52) U.S. Cl.
CPC .......... *A61K 47/60* (2017.08); *A61K 47/542* (2017.08); *A61P 5/26* (2018.01)

(58) Field of Classification Search
CPC .... A61K 35/16; A61K 38/17; A61K 38/1709; G01N 33/92
See application file for complete search history.

(56) References Cited

U.S. PATENT DOCUMENTS

| 7,824,898 B2 * | 11/2010 | Davis .................... C12N 9/88 435/232 |
| 8,907,053 B2 | 12/2014 | Sasikumar et al. |
| 10,301,357 B2 * | 5/2019 | Papadopoulos ........ C07K 14/47 |
| 2007/0269437 A1 | 11/2007 | Djurup et al. |
| 2009/0075377 A1 | 3/2009 | Lu et al. |
| 2013/0330335 A1 | 12/2013 | Bremel et al. |
| 2016/0108087 A1 | 4/2016 | Papadopoulos et al. |
| 2017/0161430 A1 | 6/2017 | Bremel |

FOREIGN PATENT DOCUMENTS

| WO | 2013143504 A1 | 10/2013 | |
| WO | 2014039718 A1 | 3/2014 | |
| WO | WO2014/197979 | * 12/2014 | ............. C07K 14/47 |
| WO | 2018158985 A1 | 7/2018 | |

OTHER PUBLICATIONS

Chain et al. Burkholderia xenovorans LB400 harbors a multi-replicon, 9,73 MBP genome shaped for versatility. PNAS, 2006, vol. 103, No. 42, pp. 15280-15287. (Year: 2006).*
https://web.expasy.org/protparam/ accessed online Dec. 4, 2024, 1 page. (Year: 2024).*
https://www.expasy.org/resources/protparam, accessed online Dec. 4, 2024, 2 pages. (Year: 2024).*
Gelman, Julia S.et al., "Peptidomic Analysis of Human Cell Lines", Journal of Proteome Research, vol. 10, No. 4, (Apr. 1, 2022), pp. 1583-1592.
Gelman, Julia S. et al., "Supplemental Information Peptidomic analysis of human cell lines", Journal of Proteome Research, (Apr. 1, 2011), https://pubs.acs.org/doi/suppl/10.1021/pr100952f/suppl_file/pr100952f_si_001.pdf, 29 pages.
Werle, M. et al., "Strategies to improve plasma half life time of peptide and protein drugs", Amino Acids; the Forum for Amino Acid and Protean Research, vol. 30, No. 4, (Apr. 20, 2006), pp. 351-367.
Supplemental Partial European Search Report, dated Sep. 8, 2022, for Europe Patent Application 19 88 2324.7, 14 pages.
Aghazadeh, Y. et al., Induction of Androgen Formation in the Male by a TAT-VDAC1 Fusion Peptide Blocking 12-3-3 ε Protein Adaptor and Mitochondrial VDAC1 Interation, Mol Ther. 2014, 22(10):1779-1791. ISSN 1525-0024.
International Search Report for PCT/CA2019/051559, Dated Jul. 2019, 6 Pages.
Japan Office Action issued on Nov. 28, 2023, in the corresponding Japanese Patent Application 2021-0525026, 25 pages, with English Translation.
Chinese Office Action issued on Nov. 23, 2024, in the corresponding Chinese Patent Application 2024112300425080, 8 pages, with English Translation.

* cited by examiner

*Primary Examiner* — Marcela M Cordero Garcia

(57) ABSTRACT

The present disclosure concerns peptide compounds of formula I or II and combinations thereof that can be administered orally for promoting endogenous steroid, and particularly testosterone, production:

(I)
A-Xaa$_1$-Xaa$_2$-Xaa$_3$-Xaa$_4$-Xaa$_5$-Xaa$_6$-Xaa$_7$-Xaa$_8$-B (II)
A-Xaa$_1$-Xaa$_A$-Xaa$_B$-Xaa$_2$-Xaa$_3$-Xaa$_4$-Xaa$_5$-Xaa$_6$-Xaa$_7$-Xaa$_C$-Xaa$_D$-Xaa$_E$-Xaa$_8$-B.

20 Claims, 23 Drawing Sheets
Specification includes a Sequence Listing.

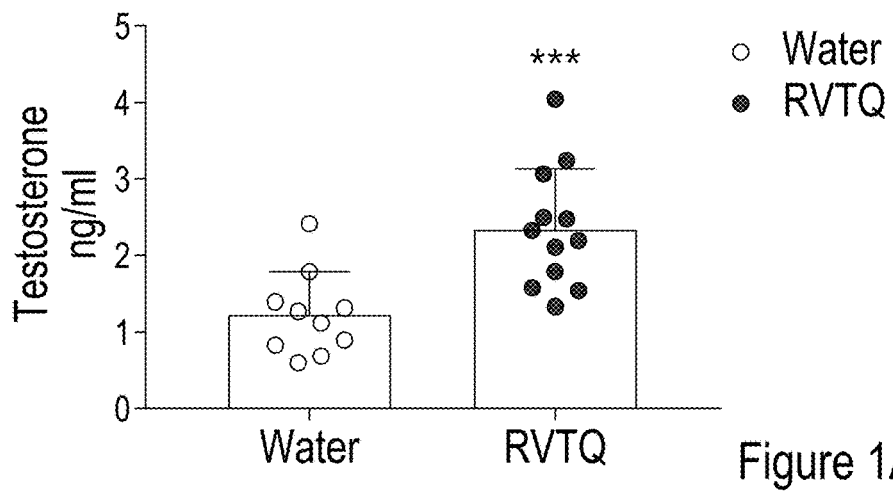
Figure 1A
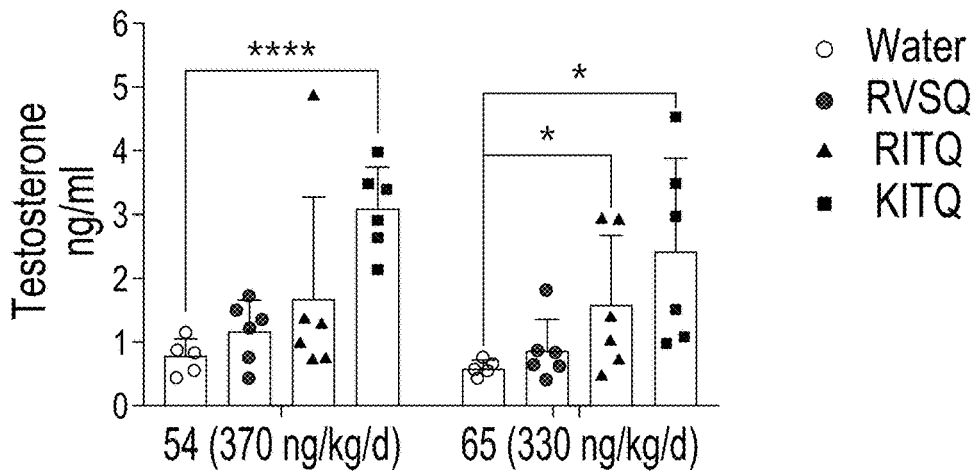
Figure 1B
Figure 1C

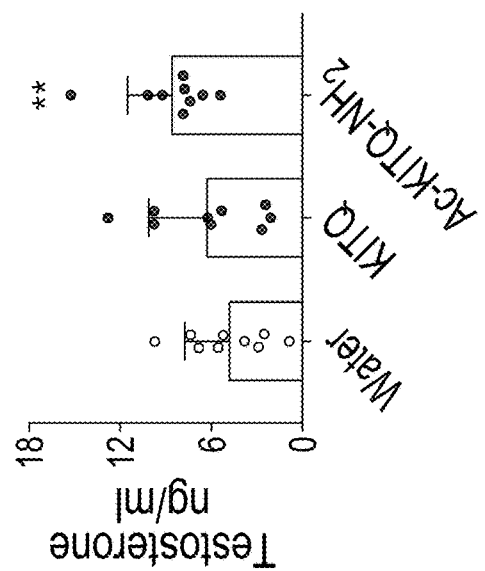
Figure 3A
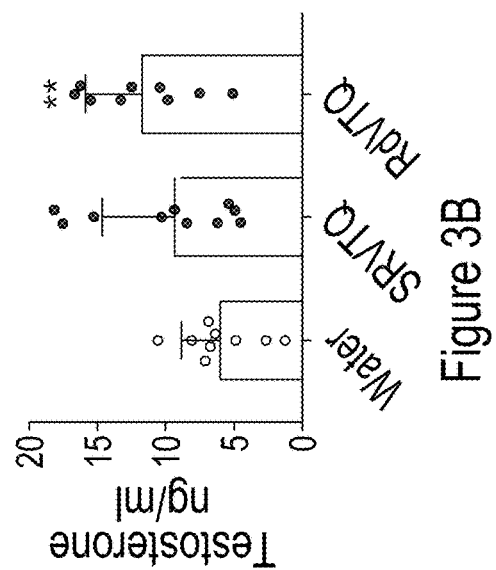
Figure 3B
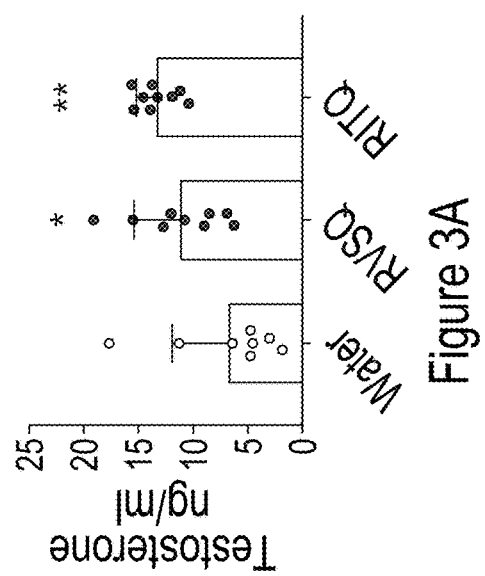
Figure 3C
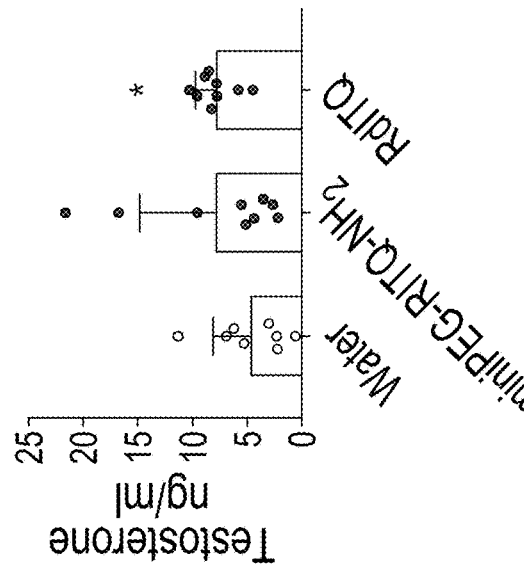
Figure 3D
Figure 3E
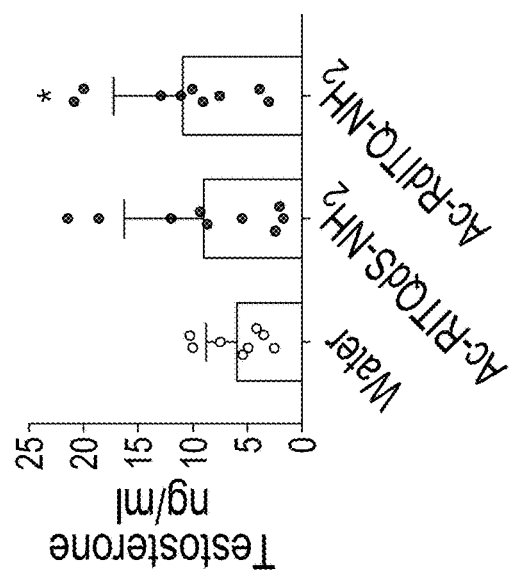
Figure 3F

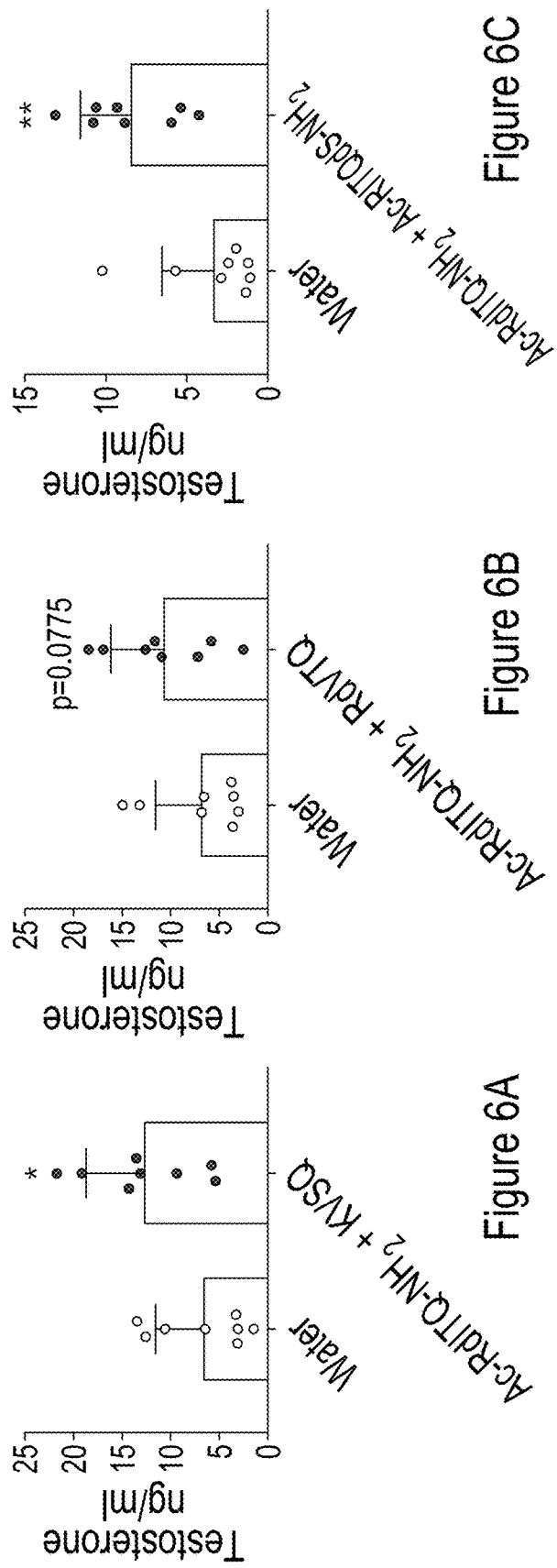
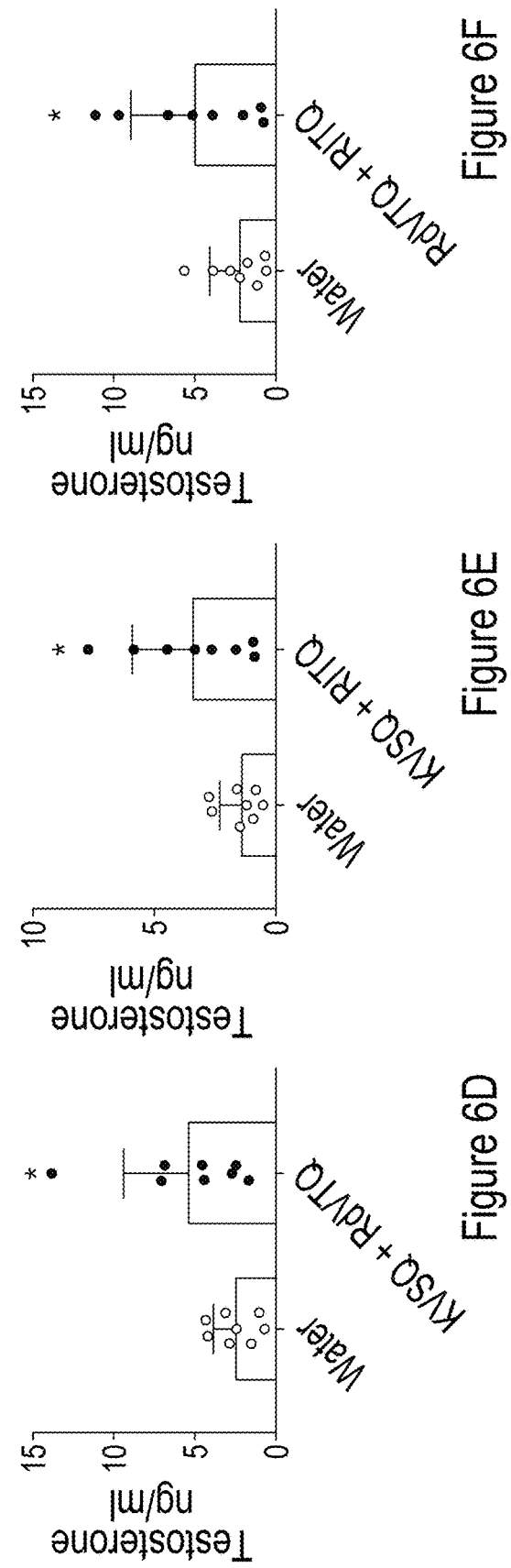

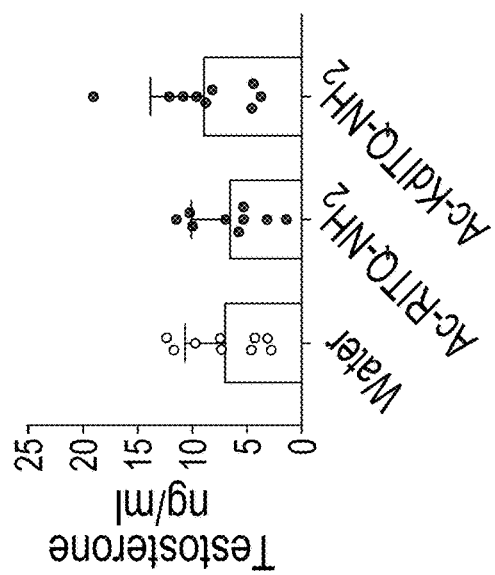
Figure 11A
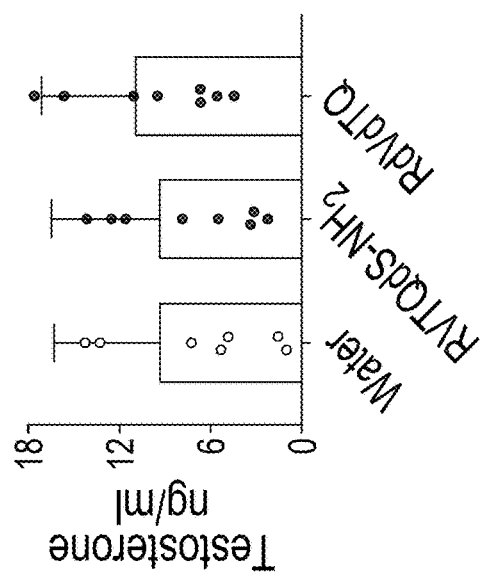
Figure 11B
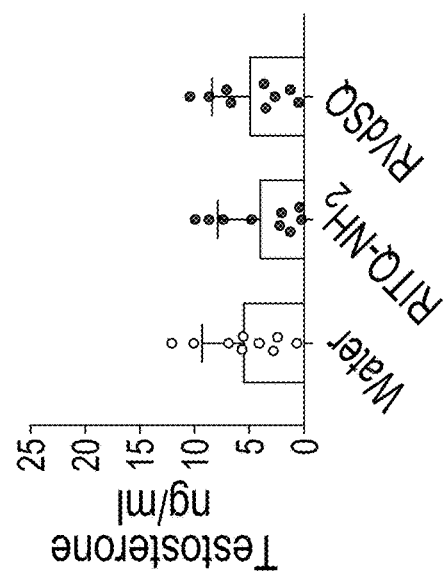
Figure 11C
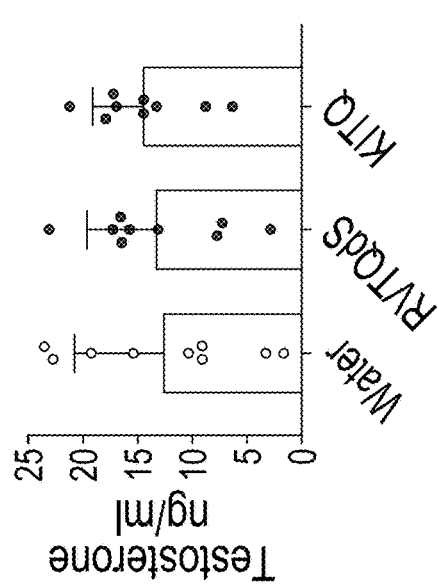
Figure 11D
Figure 11E
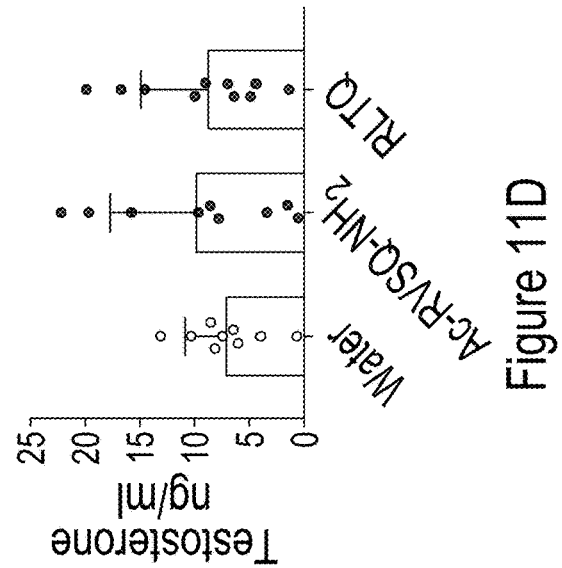
Figure 11F

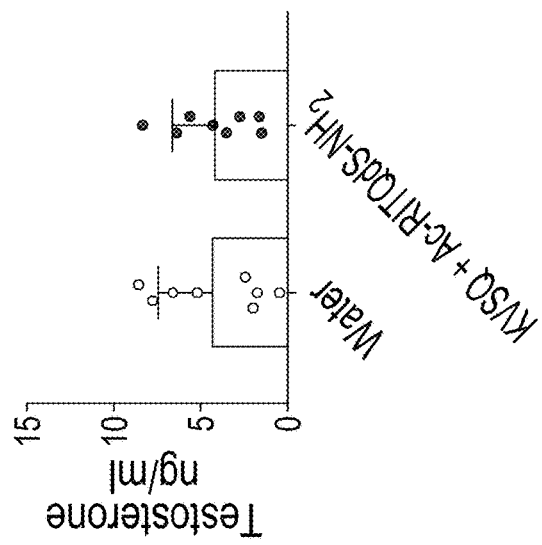
Figure 12C
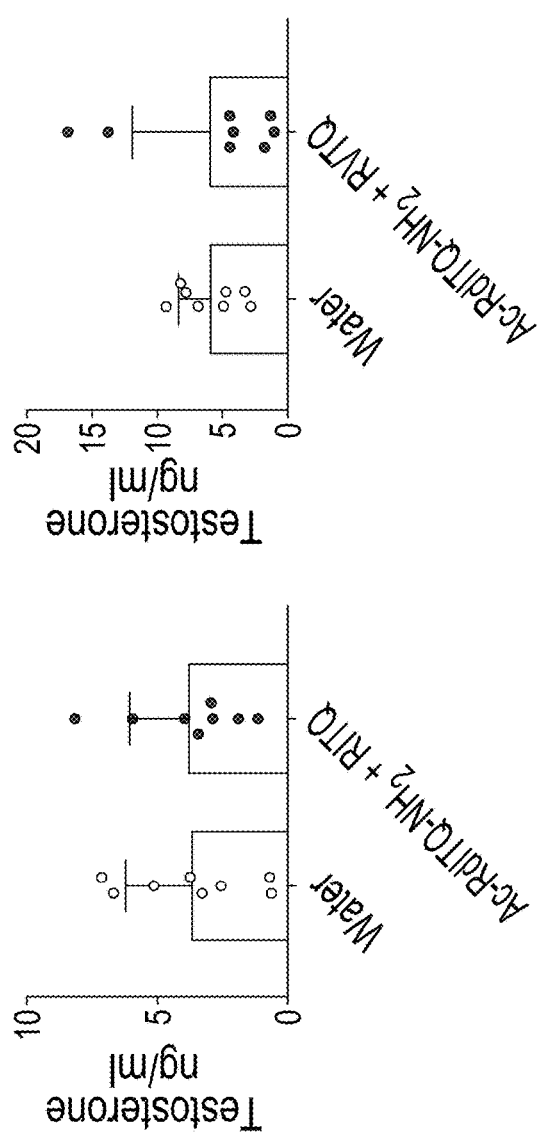
Figure 12B
Figure 12A
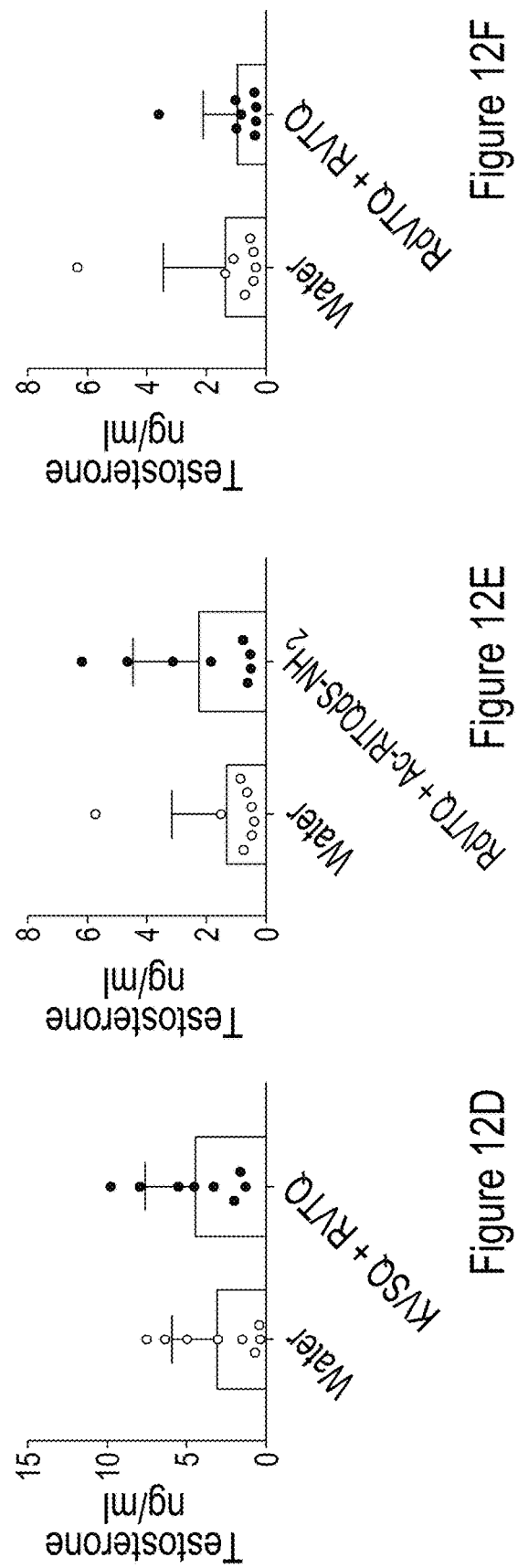
Figure 12F
Figure 12E
Figure 12D

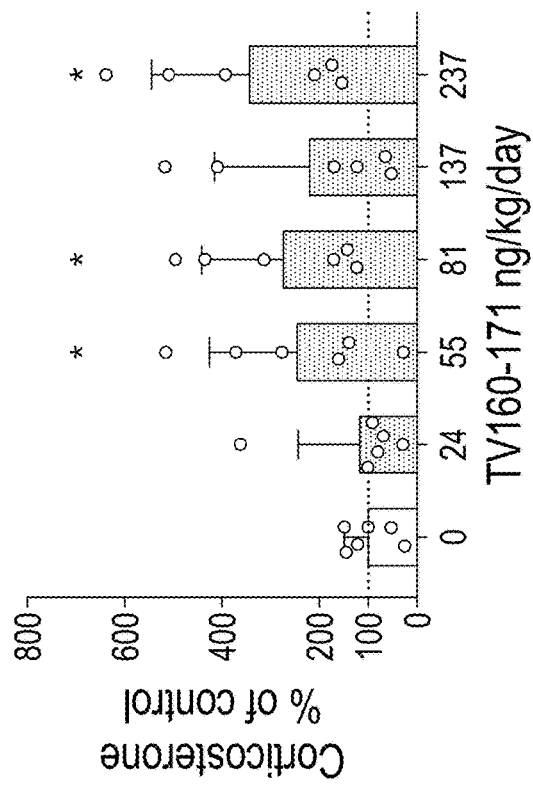
Figure 14B
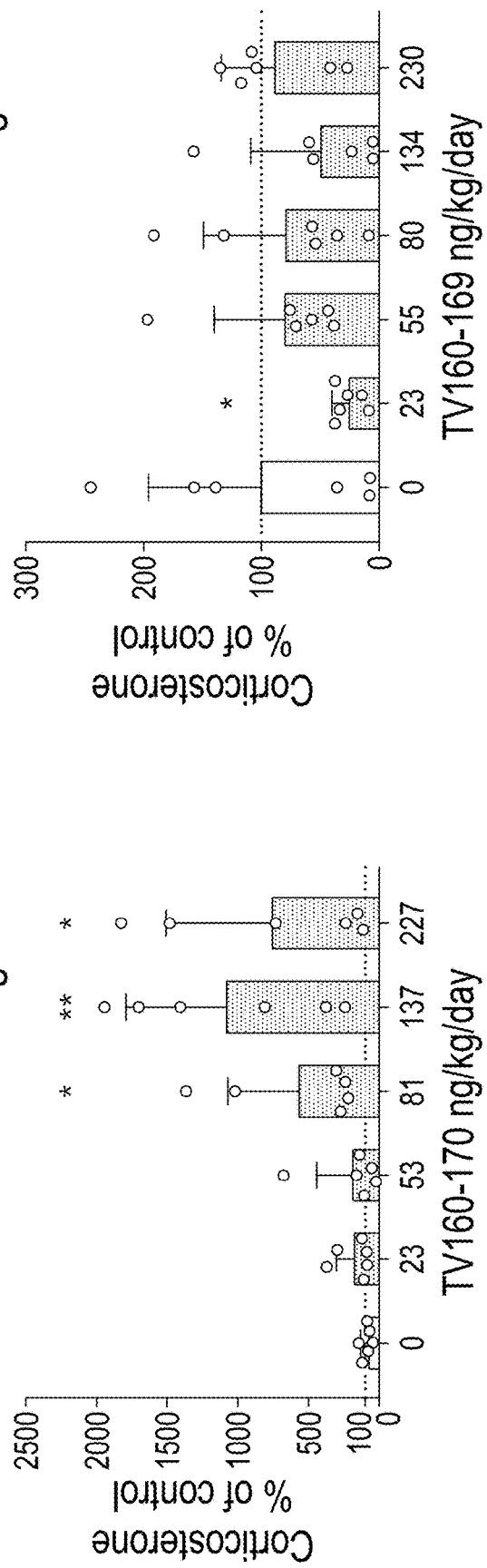
Figure 14D
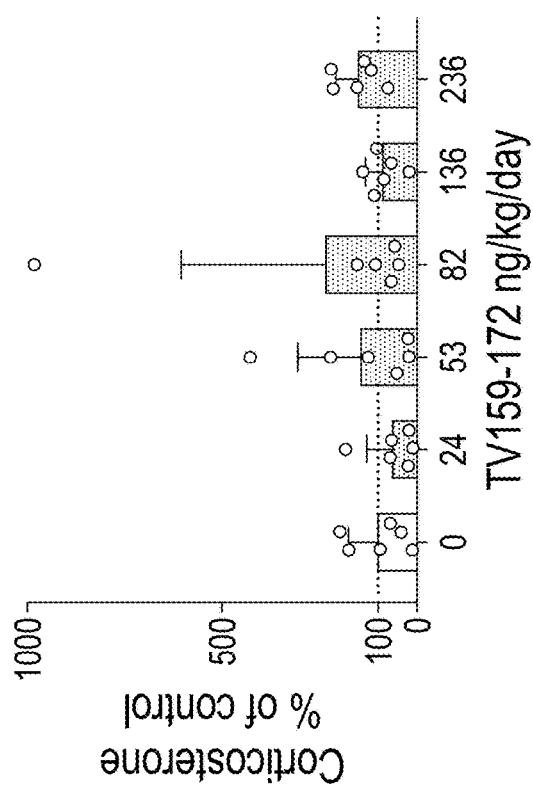
Figure 14A
Figure 14C

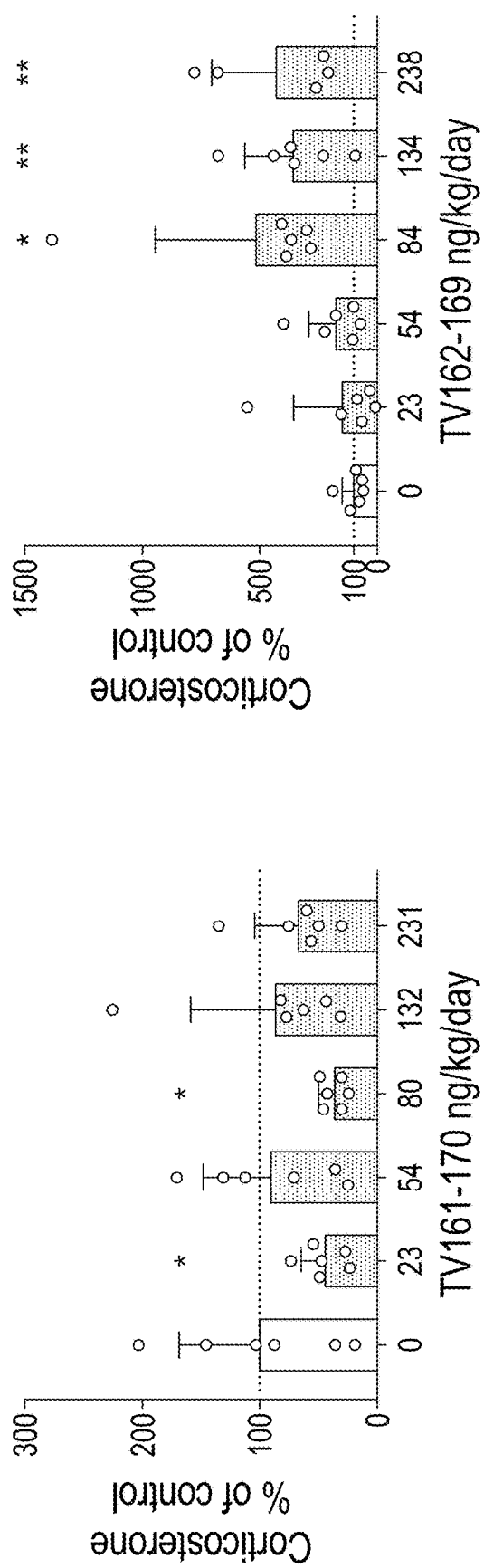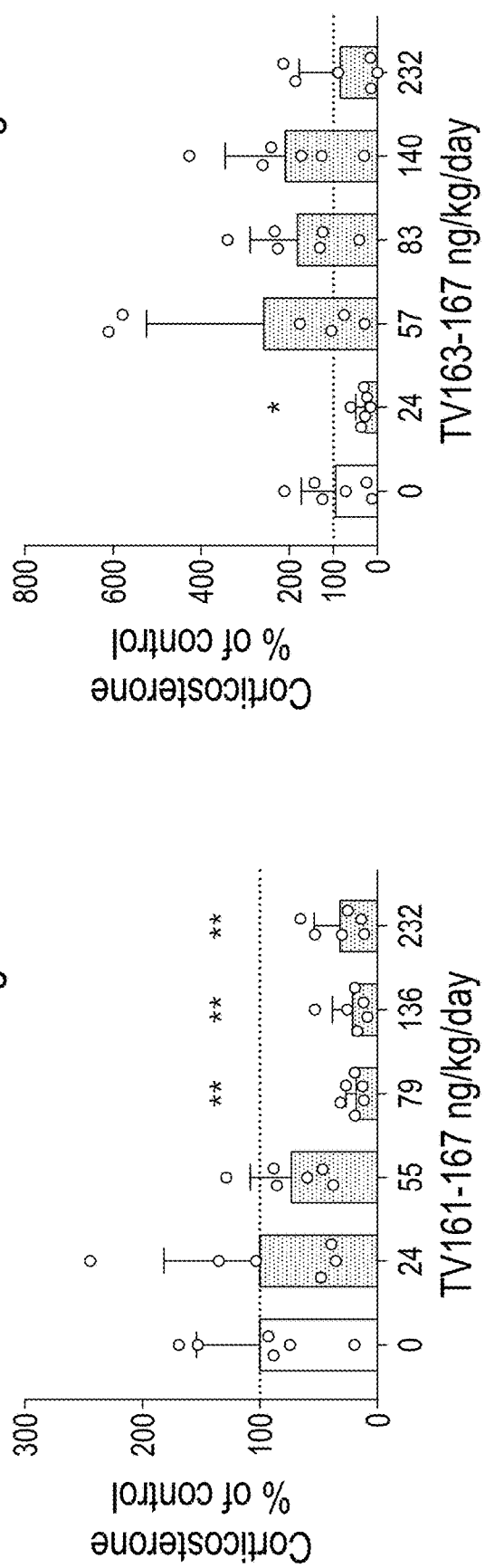
Figure 14E
Figure 14F
Figure 14G
Figure 14H

| | | 159 | 160 | 161 | 162 | 163 | 164 | 165 | 166 | 167 | 168 | 169 | 170 | 171 | 172 | MW (Da) |
|---|---|---|---|---|---|---|---|---|---|---|---|---|---|---|---|---|
| TV159-172 | TAT G | T | S | K | S | R | V | T | Q | S | N | F | A | V | G | 3,082 |
| TV160-171 | TAT G | | S | K | S | R | V | T | Q | S | N | F | A | V | | 2,922 |
| TV160-170 | TAT G | | S | K | S | R | V | T | Q | S | N | F | A | | | 2,823 |
| TV160-169 | TAT G | | S | K | S | R | V | T | Q | S | N | F | | | | 2,752 |
| TV161-170 | TAT G | | | K | S | R | V | T | Q | S | N | F | A | | | 2,736 |
| TV162-169 | TAT G | | | | S | R | V | T | Q | S | N | F | | | | 2,537 |
| TV161-167 | TAT G | | | K | S | R | V | T | Q | S | | | | | | 2,518 |
| TV163-167 | TAT G | | | | | R | V | T | Q | S | | | | | | 2,189 |
| TV162-166 | TAT G | | | | S | R | V | T | Q | | | | | | | 2,189 |
| N163-166 | | | | | | R | V | T | Q | | | | | | | 503 |
Figure 15A
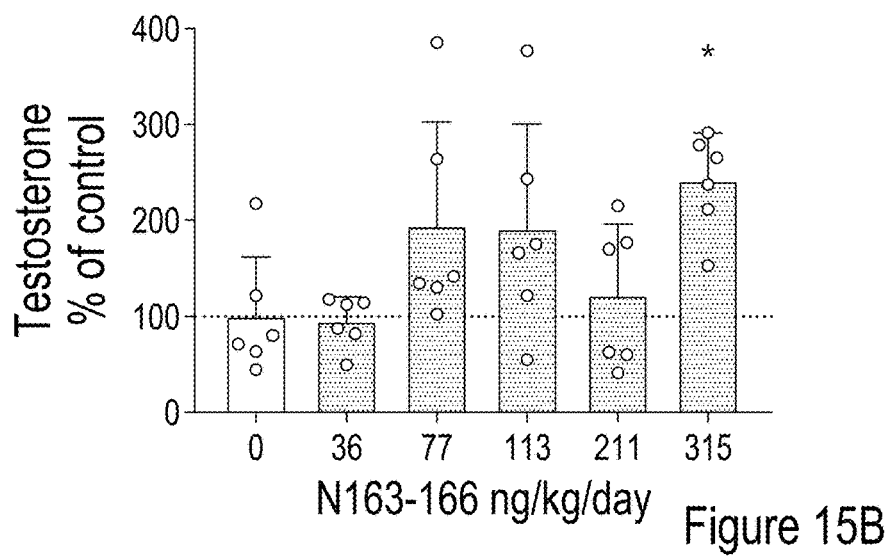
Figure 15B
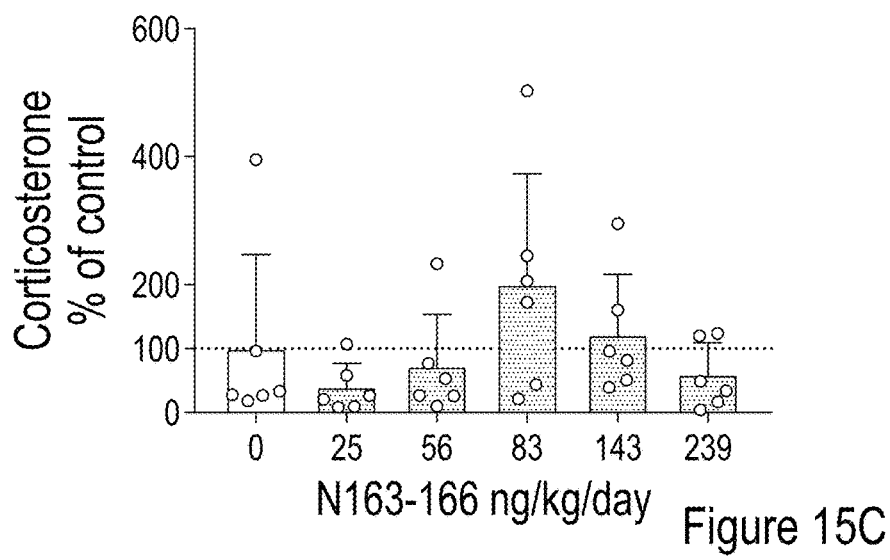
Figure 15C

SEQUENCE LISTING

<160> NUMBER OF SEQ ID NOS: 34

<210> SEQ ID NO 1

```
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 1

Lys Val Ser Gln
1

<210> SEQ ID NO 2
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 2

Arg Val Thr Gln
1

<210> SEQ ID NO 3
<211> LENGTH: 4
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (2)..(2)
<223> OTHER INFORMATION: Xaa is a D-valine

<400> SEQUENCE: 3

Arg Xaa Thr Gln
1

<210> SEQ ID NO 4
<211> LENGTH: 4
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (3)..(3)
<223> OTHER INFORMATION: Xaa is a D-threonine

<400> SEQUENCE: 4

Arg Val Xaa Gln
1

<210> SEQ ID NO 5
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 5

Arg Val Ser Gln
1

<210> SEQ ID NO 6
<211> LENGTH: 4
<212> TYPE: PRT
<213> ORGANISM: Artificial Sequence
<220> FEATURE:
<223> OTHER INFORMATION: SYNTHETIC PEPTIDE
<220> FEATURE:
```

```
<221> NAME/KEY: VARIANT
<222> LOCATION: (2)..(2)
<223> OTHER INFORMATION: Xaa is a D-valine

<400> SEQUENCE: 6

Arg Xaa Ser Gln
1

<210> SEQ ID NO 7
<211> LENGTH: 4
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (3)..(3)
<223> OTHER INFORMATION: Xaa is a D-serine

<400> SEQUENCE: 7

Arg Val Xaa Gln
1

<210> SEQ ID NO 8
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 8

Arg Ile Thr Gln
1

<210> SEQ ID NO 9
<211> LENGTH: 4
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (2)..(2)
<223> OTHER INFORMATION: Xaa is D-isoleucine

<400> SEQUENCE: 9

Arg Xaa Thr Gln
1

<210> SEQ ID NO 10
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 10

Lys Ile Thr Gln
1

<210> SEQ ID NO 11
<211> LENGTH: 4
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (2)..(2)
```

```
<223> OTHER INFORMATION: Xaa is D-isoleucine

<400> SEQUENCE: 11

Lys Xaa Thr Gln
1

<210> SEQ ID NO 12
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 12

Arg Val Thr Gln Ser
1               5

<210> SEQ ID NO 13
<211> LENGTH: 5
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (5)..(5)
<223> OTHER INFORMATION: Xaa is D-serine

<400> SEQUENCE: 13

Arg Val Thr Gln Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 14

Arg Ile Thr Gln Ser
1               5

<210> SEQ ID NO 15
<211> LENGTH: 5
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (5)..(5)
<223> OTHER INFORMATION: Xaa is D-serine

<400> SEQUENCE: 15

Arg Ile Thr Gln Xaa
1               5

<210> SEQ ID NO 16
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 16

Arg Ile Ser Gln
1
```

```
<210> SEQ ID NO 17
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 17

Ser Arg Val Thr Gln
1               5

<210> SEQ ID NO 18
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 18

Ser Arg Val Thr Gln
1               5

<210> SEQ ID NO 19
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 19

Lys Ile Ser Gln
1

<210> SEQ ID NO 20
<211> LENGTH: 4
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (2)..(2)
<223> OTHER INFORMATION: Xaa is D-isoleucine

<400> SEQUENCE: 20

Lys Xaa Ser Gln
1

<210> SEQ ID NO 21
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 21

Arg Val Thr Glu
1

<210> SEQ ID NO 22
<211> LENGTH: 4
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
```

```
<222> LOCATION: (2)..(2)
<223> OTHER INFORMATION: Xaa is a D-valine
<220> FEATURE:
<221> NAME/KEY: VARIANT
<222> LOCATION: (3)..(3)
<223> OTHER INFORMATION: Xaa is D-threonine

<400> SEQUENCE: 22

Arg Xaa Xaa Gln
1

<210> SEQ ID NO 23
<211> LENGTH: 6
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (1)..(1)
<223> OTHER INFORMATION: Xaa is D-serine
<220> FEATURE:
<221> NAME/KEY: VARIANT
<222> LOCATION: (6)..(6)
<223> OTHER INFORMATION: Xaa is D-serine

<400> SEQUENCE: 23

Xaa Arg Val Thr Gln Xaa
1               5

<210> SEQ ID NO 24
<211> LENGTH: 4
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (1)..(1)
<223> OTHER INFORMATION: Xaa is lysine or arginine
<220> FEATURE:
<221> NAME/KEY: VARIANT
<222> LOCATION: (2)..(2)
<223> OTHER INFORMATION: Xaa is valine, isoleucine or leucine
<220> FEATURE:
<221> NAME/KEY: VARIANT
<222> LOCATION: (3)..(3)
<223> OTHER INFORMATION: Xaa is serine or threonine
<220> FEATURE:
<221> NAME/KEY: VARIANT
<222> LOCATION: (4)..(4)
<223> OTHER INFORMATION: Xaa is glutamine or glutamic acid

<400> SEQUENCE: 24

Xaa Xaa Xaa Xaa
1

<210> SEQ ID NO 25
<211> LENGTH: 6
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (1)..(1)
<223> OTHER INFORMATION: Xaa can be present or absent, when present can
      be serine
<220> FEATURE:
<221> NAME/KEY: VARIANT
<222> LOCATION: (2)..(2)
<223> OTHER INFORMATION: Xaa is lysine or arginine
<220> FEATURE:
```

```
<221> NAME/KEY: VARIANT
<222> LOCATION: (3)..(3)
<223> OTHER INFORMATION: Xaa is valine, isoleucine or leucine
<220> FEATURE:
<221> NAME/KEY: VARIANT
<222> LOCATION: (4)..(4)
<223> OTHER INFORMATION: Xaa is serine or threonine
<220> FEATURE:
<221> NAME/KEY: VARIANT
<222> LOCATION: (5)..(5)
<223> OTHER INFORMATION: Xaa is glutamine or glutamic acid
<220> FEATURE:
<221> NAME/KEY: VARIANT
<222> LOCATION: (6)..(6)
<223> OTHER INFORMATION: Xaa can be present or absent, when present can
      be serine

<400> SEQUENCE: 25

Xaa Xaa Xaa Xaa Xaa Xaa
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: Xaa can be present or absent, when present can
      be any amino acid
<220> FEATURE:
<221> NAME/KEY: VARIANT
<222> LOCATION: (2)..(2)
<223> OTHER INFORMATION: Xaa can be present or absent, when present can
      be serine
<220> FEATURE:
<221> NAME/KEY: VARIANT
<222> LOCATION: (3)..(3)
<223> OTHER INFORMATION: Xaa is lysine or arginine
<220> FEATURE:
<221> NAME/KEY: VARIANT
<222> LOCATION: (4)..(4)
<223> OTHER INFORMATION: Xaa is valine, isoleucine or leucine
<220> FEATURE:
<221> NAME/KEY: VARIANT
<222> LOCATION: (5)..(5)
<223> OTHER INFORMATION: Xaa is serine or threonine
<220> FEATURE:
<221> NAME/KEY: VARIANT
<222> LOCATION: (6)..(6)
<223> OTHER INFORMATION: Xaa is glutamine or glutamic acid
<220> FEATURE:
<221> NAME/KEY: VARIANT
<222> LOCATION: (7)..(7)
<223> OTHER INFORMATION: Xaa can be present or absent, when present can
      be serine
<220> FEATURE:
<221> NAME/KEY: VARIANT
<222> LOCATION: (8)..(8)
<223> OTHER INFORMATION: Xaa can be present or absent, when present can
      be any amino acid

<400> SEQUENCE: 26

Xaa Xaa Xaa Xaa Xaa Xaa Xaa Xaa
1               5

<210> SEQ ID NO 27
<211> LENGTH: 10
<212> TYPE: PRT
<213> ORGANISM: Artificial Sequence
<220> FEATURE:
<223> OTHER INFORMATION: synthetic peptide
<220> FEATURE:
```

```
<221> NAME/KEY: VARIANT
<222> LOCATION: (1)..(1)
<223> OTHER INFORMATION: Xaa can be present or absent, when present can
      be any amino acid
<220> FEATURE:
<221> NAME/KEY: VARIANT
<222> LOCATION: (2)..(2)
<223> OTHER INFORMATION: Xaa can be present or absent, when present can
      be a serine
<220> FEATURE:
<221> NAME/KEY: VARIANT
<222> LOCATION: (3)..(3)
<223> OTHER INFORMATION: Xaa can be present or absent, when present can
      be a proline
<220> FEATURE:
<221> NAME/KEY: VARIANT
<222> LOCATION: (4)..(4)
<223> OTHER INFORMATION: Xaa can be present or absent, when present can
      be a serine
<220> FEATURE:
<221> NAME/KEY: VARIANT
<222> LOCATION: (5)..(5)
<223> OTHER INFORMATION: Xaa is lysine or arginine
<220> FEATURE:
<221> NAME/KEY: VARIANT
<222> LOCATION: (6)..(6)
<223> OTHER INFORMATION: Xaa is valine, isoleucine or leucine
<220> FEATURE:
<221> NAME/KEY: VARIANT
<222> LOCATION: (7)..(7)
<223> OTHER INFORMATION: Xaa is serine or threonine
<220> FEATURE:
<221> NAME/KEY: VARIANT
<222> LOCATION: (8)..(8)
<223> OTHER INFORMATION: Xaa is glutamine or glutamic acid
<220> FEATURE:
<221> NAME/KEY: VARIANT
<222> LOCATION: (9)..(9)
<223> OTHER INFORMATION: Xaa can be present or absent, when present can
      be a serine
<220> FEATURE:
<221> NAME/KEY: VARIANT
<222> LOCATION: (10)..(10)
<223> OTHER INFORMATION: Xaa can be present or absent, when present can
      be any amino acid

<400> SEQUENCE: 27

Xaa Xaa Xaa Xaa Xaa Xaa Xaa Xaa Xaa Xaa
1               5                   10

<210> SEQ ID NO 28
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: Xaa can be present or absent, when present can
      be any amino acid
<220> FEATURE:
<221> NAME/KEY: VARIANT
<222> LOCATION: (2)..(2)
<223> OTHER INFORMATION: Xaa can be present or absent, when present can
      be serine
<220> FEATURE:
<221> NAME/KEY: VARIANT
<222> LOCATION: (3)..(3)
<223> OTHER INFORMATION: Xaa is lysine or arginine
<220> FEATURE:
<221> NAME/KEY: VARIANT
<222> LOCATION: (4)..(4)
<223> OTHER INFORMATION: Xaa is valine, isoleucine or leucine
<220> FEATURE:
<221> NAME/KEY: VARIANT
<222> LOCATION: (5)..(5)
```

```
<223> OTHER INFORMATION: Xaa is serine or threonine
<220> FEATURE:
<221> NAME/KEY: VARIANT
<222> LOCATION: (6)..(6)
<223> OTHER INFORMATION: Xaa is glutamine or glutamic acid
<220> FEATURE:
<221> NAME/KEY: VARIANT
<222> LOCATION: (7)..(7)
<223> OTHER INFORMATION: Xaa can be present or absent, when present can
      be serine
<220> FEATURE:
<221> NAME/KEY: VARIANT
<222> LOCATION: (8)..(8)
<223> OTHER INFORMATION: Xaa can be present or absent, when present can
      be arginine
<220> FEATURE:
<221> NAME/KEY: VARIANT
<222> LOCATION: (9)..(9)
<223> OTHER INFORMATION: Xaa can be present or absent, when present can
      be phenylalanine
<220> FEATURE:
<221> NAME/KEY: VARIANT
<222> LOCATION: (10)..(10)
<223> OTHER INFORMATION: Xaa can be present or absent, when present can
      be alanine
<220> FEATURE:
<221> NAME/KEY: VARIANT
<222> LOCATION: (11)..(11)
<223> OTHER INFORMATION: Xaa can be present or absent, when present can
      be any amino acid

<400> SEQUENCE: 28

Xaa Xaa Xaa Xaa Xaa Xaa Xaa Xaa Xaa Xaa Xaa
1               5                   10

<210> SEQ ID NO 29
<211> LENGTH: 13
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: VARIANT
<222> LOCATION: (1)..(1)
<223> OTHER INFORMATION: Xaa can be present or absent, when present can
      be any amino acid
<220> FEATURE:
<221> NAME/KEY: VARIANT
<222> LOCATION: (2)..(2)
<223> OTHER INFORMATION: Xaa can be present or absent, when present can
      be a serine
<220> FEATURE:
<221> NAME/KEY: VARIANT
<222> LOCATION: (3)..(3)
<223> OTHER INFORMATION: Xaa can be present or absent, when present can
      be a proline
<220> FEATURE:
<221> NAME/KEY: VARIANT
<222> LOCATION: (4)..(4)
<223> OTHER INFORMATION: Xaa can be present or absent, when present can
      be serine
<220> FEATURE:
<221> NAME/KEY: VARIANT
<222> LOCATION: (5)..(5)
<223> OTHER INFORMATION: Xaa is lysine or arginine
<220> FEATURE:
<221> NAME/KEY: VARIANT
<222> LOCATION: (6)..(6)
<223> OTHER INFORMATION: Xaa is valine, isoleucine or leucine
<220> FEATURE:
<221> NAME/KEY: VARIANT
<222> LOCATION: (7)..(7)
<223> OTHER INFORMATION: Xaa is serine or threonine
<220> FEATURE:
<221> NAME/KEY: VARIANT
<222> LOCATION: (8)..(8)
<223> OTHER INFORMATION: Xaa is glutamine or glutamic acid
```

```
<220> FEATURE:
<221> NAME/KEY: VARIANT
<222> LOCATION: (9)..(9)
<223> OTHER INFORMATION: Xaa can be present or absent, when present can
      be serine.
<220> FEATURE:
<221> NAME/KEY: VARIANT
<222> LOCATION: (10)..(10)
<223> OTHER INFORMATION: Xaa can be present or absent, when present can
      be arginine
<220> FEATURE:
<221> NAME/KEY: VARIANT
<222> LOCATION: (11)..(11)
<223> OTHER INFORMATION: Xaa can be present or absent, when present can
      be phenylalanine
<220> FEATURE:
<221> NAME/KEY: VARIANT
<222> LOCATION: (12)..(12)
<223> OTHER INFORMATION: Xaa can be present or absent, when present can
      be alanine
<220> FEATURE:
<221> NAME/KEY: VARIANT
<222> LOCATION: (13)..(13)
<223> OTHER INFORMATION: Xaa can be present or absent, when present can
      be any amino acid

<400> SEQUENCE: 29

Xaa Xaa Xaa Xaa Xaa Xaa Xaa Xaa Xaa Xaa Xaa Xaa Xaa
1               5                   10

<210> SEQ ID NO 30
<211> LENGTH: 7
<212> TYPE: PRT
<213> ORGANISM: Artificial Sequence
<220> FEATURE:
<223> OTHER INFORMATION: SYNTHETIC PEPTIDE

<400> SEQUENCE: 30

Lys Ser Arg Val Thr Gln Ser
1               5

<210> SEQ ID NO 31
<211> LENGTH: 8
<212> TYPE: PRT
<213> ORGANISM: Artificial Sequence
<220> FEATURE:
<223> OTHER INFORMATION: SYNTHETIC PEPTIDE

<400> SEQUENCE: 31

Ser Arg Val Thr Gln Ser Asn Phe
1               5

<210> SEQ ID NO 32
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 32

Lys Ser Arg Val Thr Gln Ser Asn Phe Ala
1               5                   10

<210> SEQ ID NO 33
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 33
```

```
Ser Lys Ser Arg Val Thr Gln Ser Asn Phe
1               5                   10

<210> SEQ ID NO 34
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 34

Ser Lys Ser Arg Val Thr Gln Ser Asn Phe Ala
1               5                   10
```

TESTOSTERONE-INDUCING PEPTIDE COMPOUNDS AND ASSOCIATED COMBINATIONS

CROSS-REFERENCE TO RELATED APPLICATIONS AND DOCUMENTS

This application claims priority from U.S. provisional application 62/756,767 filed on Nov. 7, 2018, incorporated herewith in its entirety. The sequence listing associated with this application is provided in text format in lieu of a paper copy and is hereby incorporated by reference into the specification. The name of the text file containing the sequence listing is 56080224-2PCT_Sequence listing as filed. The text file is 12 KB, was created on Nov. 4, 2019 and is being submitted electronically via EFS-Web.

TECHNOLOGICAL FIELD

The present disclosure relates to therapeutic compounds having an amino acid core which are capable of inducing the production of endogenous testosterone.

BACKGROUND

Testosterone levels in men physiologically decrease at a rate of 0.4 to 2% per year starting at age 30. The hypothalamic-pituitary-gonadal (HPG) axis regulates these testosterone levels via a series of feedback loops. Briefly, testosterone is produced in the testes by Leydig cells in response to luteinizing hormone (LH), which is released by the gonadotrophic cells of the anterior pituitary. The release of LH, which is pulsatile and follows a circadian rhythm, is controlled by the hypothalamic release of gonadotropin-releasing hormone (GnRH).

Hypogonadism is the decrease of testosterone levels that is often accompanied by erectile dysfunction, decreased muscle mass, gynecomastia, and osteoporosis, as well as, physiological symptoms like fatigue, mental fogginess, and decreased libido. Primary hypogonadism occurs when Leydig cell androgen production is insufficient. However, in most of the cases (85%), hypogonadism is secondary, where GnRH or LH signaling is inadequate to maintain testosterone levels. There is also a subgroup of males with a mix of central (hypothalamic and/or pituitary) and gonadal deficiency known as late-onset hypogonadism. This group is characterized by decreased testosterone levels, where the symptoms of aging overlap with those of hypogonadism, leading to confusion in their therapeutic options. Other forms of hypogonadism include compensated hypogonadism, where LH levels are increased to maintain testosterone levels in the low-normal range and which most often evolves into primary hypogonadism. Additionally, testosterone levels can decrease during trauma and may be a biomarker for surgical prognosis.

Testosterone replacement therapy (TRT) is currently the only approved therapy to treat hypogonadism and uses synthetic testosterone analogs to improve the symptoms of patients. Side effects of TRT include polycythemia, gynecomastia, and infertility. Other side effects, like cross-contamination in patients using gels and rashes in those using patches, are associated with the route of administration. There are also concerns about suppression of reproduction and abuse. Moreover, cardiovascular concerns were raised in retrospective and prospective studies. However, some studies showed no effects or even cardiovascular improvements. All these concerns lead the FDA to issue a warning and guidelines that aim to reduce the abuse of TRT, whose prescription has tripled in the past decade. Abuse of TRT is also a concern, since improper use of TRT may affect the HPG axis up to 2-3 years and, in some cases, permanently. The FDA restricted the use of TRT to those individuals with a history of decreased testosterone levels and excluded those using TRT to counter physiological testosterone decreases and those with unknown etiology. The FDA also brought attention to the cardiovascular concerns by mandating warning labels on TRT packaging.

Parental administration is an accurate way of dosing TRT, but users frequently miss doses and have the least compliance. The oral route, which is shown to have the best compliance, is not a therapeutic option due to liver toxicity. New alternatives to TRT that use the oral route and that act within the HPG axis are needed. The use of hCG, modulators of the estrogen receptor (ER) like clomiphene citrate, and aromatase inhibitors, which block the conversion of testosterone into estrogen, have been proposed but are not currently endorsed by the FDA. Overall, there is a compelling need to re-double efforts on finding a viable oral therapy.

It would be highly desirable to be provided with therapeutic agents, in some embodiments, suitable for oral dosage, for the treatment or the alleviation of symptoms associated with hypogonadism.

BRIEF SUMMARY

The present disclosure concerns peptide compounds as well as combinations of peptide compounds that are capable of promoting steroid production, testosterone and, some embodiments, upon oral administration.

In a first aspect, the present disclosure provides a peptide compound of formula (I)

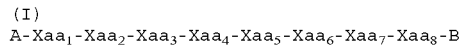

(I)
A-Xaa$_1$-Xaa$_2$-Xaa$_3$-Xaa$_4$-Xaa$_5$-Xaa$_6$-Xaa$_7$-Xaa$_8$-B wherein: A is present or absent and is a moiety improving the circulation half-life of the peptide compound; Xaa$_1$ is present or absent, when present Xaa$_1$ is one or more L- or D-amino acid residue; Xaa$_2$ is present or absent, when present Xaa$_2$ is a L-serine or D-serine; Xaa$_3$ is a L-lysine, a D-lysine, a L-arginine or a D-arginine; Xaa$_4$ is a L-valine, a D-valine, a L-isoleucine, a D-isoleucine, a L-leucine, a D-leucine, a D-glycine, a L-glycine, a D-alanine or a L-alanine; Xaa$_5$ is a L-serine, a D-serine, a L-threonine or a D-threonine; Xaa$_6$ is a L-glutamine, a D-glutamine, a L-glutamic acid or a D-glutamic acid; Xaa$_7$ is present or absent, when present Xaa$_7$ is a a L-serine or a D-serine; Xaa$_8$ is present or absent, when present Xaa$_8$ is one or more L- or D-amino acid residue; and B is present of absent and is a moiety improving the circulation half-life of the peptide compound. In some embodiments, Xaa$_1$ is absent. In further embodiments, Xaa$_2$ is absent. In such embodiments, Xaa$_3$-Xaa$_4$-Xaa$_5$-Xaa$_6$-Xaa$_7$ can have the amino acid sequence of SEQ ID NO: 1, 2, 3, 4, 5, 6, 7, 8, 9, 10, 11, 12, 13, 14, 15, 16, 18, 19, 20 or 21. In alternative embodiments, Xaa$_2$ is present. In such embodiments, Xaa$_2$-Xaa$_3$-Xaa$_4$-Xaa$_5$-Xaa$_6$-Xaa$_7$ can have the amino acid sequence of SEQ ID NO: 16 or 23. In some embodiments, Xaa$_3$ is L- or D-lysine. In such embodiments, Xaa$_3$-Xaa$_4$-Xaa$_5$-Xaa$_6$-Xaa$_7$ can have the amino acid sequence of SEQ ID NO: 1, 10, 11, 19 or 20. In some embodiments, Xaa$_3$ is L- or D-arginine. In such embodiments, Xaa$_3$-Xaa$_4$-Xaa$_5$-Xaa$_6$-Xaa$_7$ can have the amino acid sequence of SEQ ID NO: 2, 3, 4, 5, 6, 7, 8, 9, 12, 13, 14, 15, 16, 17, 18, 21, 22 or 23. In some embodiments, Xaa₄ is L-valine or D-valine. In such embodiments, Xaa₃-Xaa₄-Xaa₅-Xaa₆-Xaa₇ can have the amino acid sequence of SEQ ID NO: 1, 2, 3, 4, 5, 6, 7, 12, 13, 17, 21, 22 or 23. In some embodiments, Xaa₄ is L-isoleucine or D-isoleucine. In such embodiments, Xaa₃-Xaa₄-Xaa₅-Xaa₆-Xaa₇ can have the amino acid sequence of SEQ ID NO: 8, 9, 10, 11, 14, 15, 16, 19 or 20. In some embodiments, Xaa₄ is L-leucine or D-leucine. In such embodiments, Xaa₃-Xaa₄-Xaa₅-Xaa₆-Xaa₇ can have the amino acid sequence of SEQ ID NO: 18. In some embodiments, Xaa₅ is L-serine or D-serine. In such embodiments, Xaa₃-Xaa₄-Xaa₅-Xaa₆-Xaa₇ can have the amino acid sequence of SEQ ID NO: 1, 5, 6, 7, 16, 19, 20 or 22. In some embodiments, Xaa₅ is L-threonine or D-threonine. In such embodiments, Xaa₃-Xaa₄-Xaa₅-Xaa₆-Xaa₇ can have the amino acid sequence of SEQ ID NO: 2, 3, 4, 8, 9, 10, 11, 12, 13, 14, 15, 17, 18, 21 or 23. In some embodiments, Xaa₆ is L-glutamine or D-glutamine. In such embodiments, Xaa₃-Xaa₄-Xaa₅-Xaa₆-Xaa₇ can have the amino acid sequence of SEQ ID NO: 1, 2, 3, 4, 5, 6, 7, 8, 9, 10, 11, 12, 13, 14, 15, 16, 17, 18, 19, 20, 22 or 23. In some embodiments, Xaa₆ is L-glutamic acid or D-glutamic acid. In such embodiments, Xaa₃-Xaa₄-Xaa₅-Xaa₆-Xaa₇ can have the amino acid sequence of SEQ ID NO: 21. In some embodiments, Xaa₇ is absent. In such embodiments, Xaa₃-Xaa₄-Xaa₅-Xaa₆-Xaa₇ can have the amino acid sequence of SEQ ID NO: 1, 2, 3, 4, 5, 6, 7, 8, 9, 10, 11, 16, 17, 18, 19, 20 or 21. In some embodiments, Xaa₇ is present. In such embodiments, Xaa₃-Xaa₄-Xaa₅-Xaa₆-Xaa₇ can have the amino acid sequence of SEQ ID NO: 12, 13, 14, 15 or 23. In some embodiments, Xaa₈ is absent. In some additional embodiments, A is an acetyl cap or a polyethylene glycol. In some further embodiments, B is an amide caped amino acid residue.

In a second aspect, the present disclosure provides a peptide compound as described in Table 3.

In a third aspect, the present disclosure provides a combination of a first peptide compound as defined herein and a second peptide compound as defined herein.

In a fourth aspect, the present disclosure provides a peptide compound of formula II:

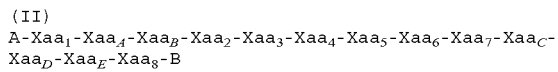

(II)
A-Xaa₁-Xaa_A-Xaa_B-Xaa₂-Xaa₃-Xaa₄-Xaa₅-Xaa₆-Xaa₇-Xaa_C-Xaa_D-Xaa_E-Xaa₈-B wherein: A is present or absent and is a moiety improving the circulation half-life of the peptide compound; Xaa₁ is present or absent, when present Xaa₁ is one or more L- or D-amino acid residue; Xaa_A is present or absent, when present Xaa_A is a L-serine or D-serine; Xaa_B is present or absent, when present Xaa_B is a L-lysine or D-lysine; Xaa₂ is present or absent, when present Xaa₂ is a L-serine or D-serine; Xaa₃ is a L-lysine, a D-lysine, a L-arginine or a D-arginine; Xaa₄ is a L-valine, a D-valine, a L-isoleucine, a D-isoleucine, a L-leucine, a D-leucine, a D-glycine, a L-glycine, a D-alanine or a L-alanine; Xaa₅ is a L-serine, a D-serine, a L-threonine or a D-threonine; Xaa₆ is a L-glutamine, a D-glutamine, a L-glutamic acid or a D-glutamic acid; Xaa₇ is present or absent, when present Xaa₇ is a a L-serine or a D-serine; Xaa_C is present or absent, when present Xaa_C is a L-asparagine or D-asparagine; Xaa_D is present or absent, when present Xaa_D is a L-phenylalanine or D-phenylalanine; Xaa_E is present or absent, when present Xaa_E is a L-alanine or D-alanine; Xaa₈ is present or absent, when present Xaa₈ is one or more L- or D-amino acid residue; and B is present of absent and is a moiety improving the circulation half-life of the peptide compound.

In a fourth aspect, the present disclosure provides a pharmaceutical composition comprising (i) a peptide compound as defined herein or a combination as defined herein and (ii) a pharmaceutically acceptable carrier. In an embodiment, the pharmaceutical composition is formulated for oral administration or parenteral administration. In yet another embodiment, the first peptide compound of the combination is formulated for administration together with the second peptide compound of the combination.

In a fifth aspect, the present disclosure provides a method for promoting the endogenous production of a steroid in a cell, said method comprising contacting the cell with at least one of: the peptide compound defined herein, the combination defined herein or the pharmaceutical composition defined herein so as to promote the endogenous production of the steroid in the cell. The present disclosure also provide the use of the peptide compound defined herein, the combination defined herein or the pharmaceutical composition defined herein for promoting the endogenous production of a steroid in a cell. The present disclosure further provides use of the peptide compound defined or the combination defined herein for manufacturing a medicament for promoting the endogenous production of a steroid in a cell. The present disclosure also provides a peptide compound defined herein, a combination as defined herein or a pharmaceutical composition as defined herein for promoting the endogenous production of a steroid in a cell. In an embodiment, the steroid is testosterone. In yet another embodiment, the cell is in vivo. In still another embodiment, the method further comprises administering a therapeutically effective amount of the peptide compound, the combination or the pharmaceutical composition to a subject in need thereof and comprising the cell. In an embodiment, the subject is a mammal, such as, for example, a male. In yet another embodiment, the cell is from a testis, such as, for example, a Leydig cell. In an embodiment, the method, use, peptide compound, combination or pharmaceutical composition is for the prevention, treatment and/or alleviation of symptoms of a condition associated with hypogonadism. In an embodiment, the condition associated with hypogonadism is at least one of infertility, aging, decreased libido, sexual dysfunction, altered mood, fatigue, decreased lean body mass, decreased bone mineral density, increased visceral fat, wasting or metabolic syndrome. In yet another embodiment, the hypogonadism is a primary hypogonadism, a secondary hypogonadism, a tertiary hypogonadism or an acquired hypogonadism.

Throughout this application, various terms are used and some of them are more precisely defined herein.

14-3-3ε protein. As used in the context of the present disclosure, the 14-3-3ε protein is encoded by the YWHAE gene and is an adapter protein involved in the regulation of a large spectrum of both general and specialized signaling pathways. The 14-3-3ε protein binds to a large number of partners, usually by recognition of a phosphoserine or phosphothreonine motif. The 14-3-3ε protein has been shown to interact with the VDAC1 protein and such interaction modulates (e.g., decreases) endogenous steroid production, such as endogenous testosterone protein.

VDAC1 protein. As used in the context of the present disclosure, the VDAC1 protein, also known as voltage-dependent anion-selective channel protein 1, is encoded by the VDAC1 gene and forms a channel through the mitochondrial outer membrane and the plasma membrane. As shown herein, the VDAC1 protein can interact with the TSPO protein to form a mitochondrial channel for the transport of cholesterol. VDAC1 has been documented in humans (Accession Number NP_003365), in mouse (Accession Number NP_035824) as well as in rats (Accession NP_112643).

BRIEF DESCRIPTION OF THE DRAWINGS

Having thus generally described the nature of the invention, reference will now be made to the accompanying drawings, showing by way of illustration, a preferred embodiment thereof, and in which:

FIGS. 1A to 1C show that subcutaneous infusion of VDAC1-derived tetrapeptides increase plasma testosterone levels. (FIG. 1A) Testosterone levels in 54 day-old Brown-Norway rats implanted with osmotic pump delivering water (○) or 377 ng/kg/d of N163-166 peptide (●, RVTQ, SEQ ID NO: 2); N=12; results shown as mean±SD; *p<0.001. (FIG. 1B) Protein sequence alignment identifying the amino acid variations (underlined) of RVTQ in other species. (FIG. 1C) Testosterone levels in 54 and 65 day-old Brown-Norway rats infused with water (○), RVSQ (●, SEQ ID NO: 3), RITQ (▲, SEQ ID NO: 4), or KITQ (■, SEQ ID NO: 5). N=6; results shown as mean±SD; **p<0.0001, *p<0.05.

(FIG. 2A) Testosterone levels in Brown-Norway rats 3 hrs after gavage with water (○), RVTQ (●, SEQ ID NO: 2) or RVTQdS-NH$_2$ (■, SEQ ID NO: 6). (FIG. 2B) Pool data showing time course of testosterone levels obtained in two rounds, 1 & 3 hrs and 2 & 5 hrs, post-gavage with water (○), RVTQ (●, SEQ ID NO: 2) or RVTQdS-NH$_2$ (■, SEQ ID NO: 6). Age of Brown-Norway rats during experiment was 60-123 days-old; N=7; results shown as mean±SD; *p<0.05.

FIGS. 3A to 3I show that amino acid changes to the RVTQ (SEQ ID NO: 2) core with or without modifications increase plasma testosterone levels after oral administration. (FIG. 3A-H) Testosterone levels 2 hrs post-gavage with various modified and naked protein cores. (FIG. 3I) Normalized testosterone levels of all peptides in the order tested. Age of Brown-Norway rats during experiment was 60-136 days-old; N=8; results shown as mean±SD; *p<0.05; **p<0.01.

(FIG. 4A) Testosterone and (FIG. 4B) corticosterone levels of Brown-Norway rats 2 hrs after gavage with the various concentrations of RdVTQ (SEQ ID NO: 7). (FIG. 4C) Testosterone and (FIG. 4D) corticosterone levels of Brown-Norway rats 2 hrs after gavage with the various concentrations of RITQ (SEQ ID NO: 4). Age of Brown-Norway rats during experiment was 88-138 days-old; N=8; results shown as mean±SD; *p<0.05.

FIGS. 6A to 6G show that oral administration of very low doses of a combination of two peptides increase plasma testosterone levels. (FIG. 6A-6F) Testosterone levels in Brown-Norway rats aged 91-134 days-old treated with 2-peptide combinations at ~10 µg peptide/kg. (FIG. 6G) Normalized testosterone levels of all peptides in the order tested. N=8; results shown as mean±SD; *p<0.05; **p<0.01.

(FIG. 8A-C) Circulating levels after single oral dose of the various peptides. Age of Brown-Norway rats during experiment was 71-110 days-old; N=4 in two rounds; Results shown as mean±SEM.

FIGS. 11A to 11J show that some modifications to the RVTQ (SEQ ID NO: 2) core sequence did not increase plasma testosterone levels. Results are shown as the plasma testosterone level in Brown-Norway rats 3 hrs after gavage with water or different peptides.

FIGS. 12A to 12I show that some dual peptide combinations that increase testosterone levels as monotherapy at higher levels did not increase plasma testosterone levels at ~10 µg/kg. Results are shown as the plasma testosterone level in Brown-Norway rats 3 hrs after gavage with water or different combinations of peptides.

(FIG. 13A to 13I) Results are shown as the plasma testosterone level in Brown-Norway rats implanted subcutaneously with osmotic pumps delivering increasing concentrations of various TV159-172 derivatives for one week. Peptides were composed of TAT sequence, glycine linker, and the VDAC1-derived sequence shown in bold. (FIG. 13J) Pooled testosterone levels of all water-treated rats and each peptide, independent of the dose. N=6; results shown as means±standard deviation.

FIGS. 14A to 14I show that various deletions of TV159-172 can still increase corticosterone levels. (FIGS. 14A to 14I) Results are shown as the plasma corticosterone level in Brown-Norway rats implanted subcutaneously with osmotic pumps delivering increasing concentrations of various TV159-172 derivatives for one week. Peptides were composed of TAT sequence, glycine linker, and the VDAC1-derived sequence shown in bold. N=6; results shown as means±standard deviation.

FIGS. 15A to 15C show that subcutaneous administration of the tetrapeptide RVTQ increases testosterone levels. (FIG. 15A) Summary of peptides used in deletion experiments delivered subcutaneously. Results are shown as testosterone (FIG. 15B) and corticosterone (FIG. 15C) plasma levels in Brown-Norway rats implanted subcutaneously with osmotic pumps delivering increasing concentrations of RVTQ peptide for one week. N=6; results shown as means±standard deviation.

DETAILED DESCRIPTION

Figure 2A:
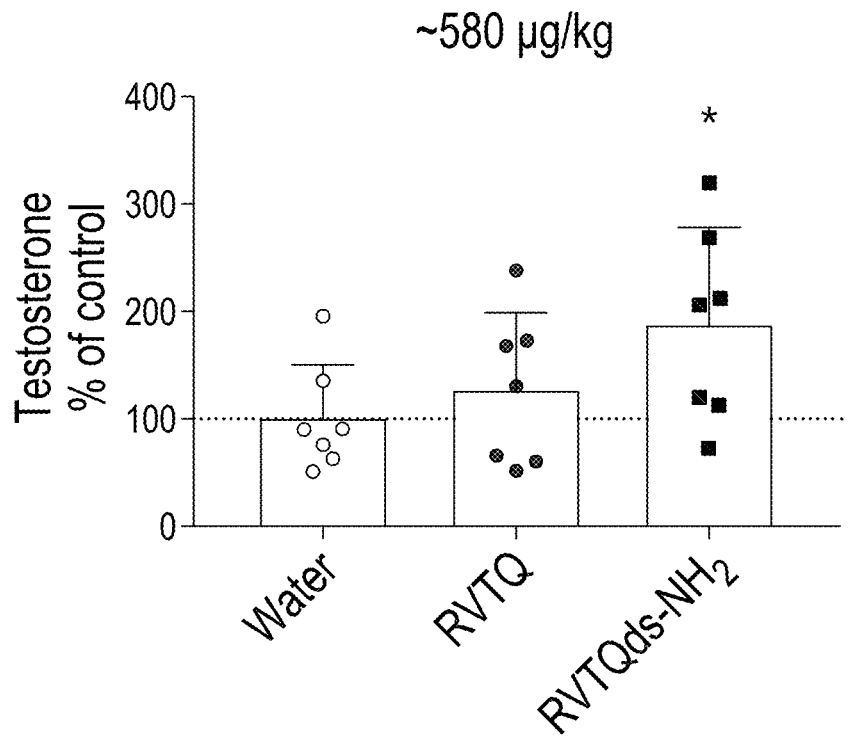
FIGS. 2A and 2B show that modifications to the RVTQ (SEQ ID NO: 2) core increase plasma testosterone levels after oral administration.

Cholesterol is the precursor of all steroids and the rate with which cholesterol enters the mitochondria directly impacts steroid biosynthesis. The voltage-sensitive anion-selective protein 1 (VDAC1) is located at the outer mitochondrial membrane and forms a permeable channel that traffics molecules across the mitochondria. In steroidogenic tissues, VDAC1 is part of a protein complex that modulates the entry of cholesterol into the mitochondria. It is known that a fusion peptide bearing a TAT-cell penetrating tag, a glycine linker, and a 14-amino acid VDAC1 sequence was capable of increasing testosterone levels ex vivo and in vivo (Aghazadeh et al., 2014).

The present disclosure concerns peptide compounds as well as combinations of peptide compounds that are capable of promoting steroid production, testosterone and, some embodiments, upon oral administration. In some embodiments, the peptide compounds and/or their associated combinations fail to modify adrenal steroidogenesis since they fail to significantly increase corticosterone levels. In some other embodiments, the peptide compounds and/or their associated combinations do increase both testosterone and corticosterone levels. In some additional embodiments, the peptide compounds and/or their associated combinations escape HPG repression because they are capable of increasing steroid levels during a ⅔ hours window. As such, the peptide compounds and/or associated combinations can thus conveniently be used for multiple dosing.

Peptide Compounds

The peptide compounds of the present disclosure comprise an amino acid core which can be modified at the amino- and/or the carboxyl-end to improve the circulation half-life. The amino acid core of the peptide compounds of the present disclosure can be composed of L-amino acid residues, D-amino acid residues as well as combinations thereof. In some embodiments, the amino acid core of the peptide compounds of the present disclosure can be composed in part or exclusively of peptidomimetics corresponding to the amino acid residues disclosed herewith.

The peptide compounds of the present disclosure can have the following formula (I):

(I)
A-$Xaa_1$-$Xaa_2$-$Xaa_3$-$Xaa_4$-$Xaa_5$-$Xaa_6$-$Xaa_7$-$Xaa_8$-B

In the peptide compounds of formula I, residues A, $Xaa_1$, $Xaa_2$, $Xaa_7$, $Xaa_8$ and B are optional and residues $Xaa_3$, $Xaa_4$, $Xaa_5$ and $Xaa_6$ are always present. As used in the context of the present disclosure, the "amino acid core" refers to "$Xaa_1$-$Xaa_2$-$Xaa_3$-$Xaa_4$-$Xaa_5$-$Xaa_6$-$Xaa_7$-$Xaa_8$" and excludes the A and B residues. The symbol "-" in the amino acid core refers to a peptide bound that is formed between two contiguous amino acid residues. Furthermore, the "amino acid core" always includes "$Xaa_3$-$Xaa_4$-$Xaa_5$-$Xaa_6$".

As indicated above, at minimum, the amino acid core of the peptide compounds comprises "$Xaa_3$-$Xaa_4$-$Xaa_5$-$Xaa_6$". Residue $Xaa_3$ can be any amino acid residue, and preferably a lysine or an arginine (each independently selected to be the D- or L-enantiomer). In some embodiments, $Xaa_3$ is an arginine (in the D- or L-enantiomer). Residue $Xaa_4$ can be any amino acid residue, and preferably a valine, an isoleucine, a leucine, a glycine or an alanine (each independently selected to be the D- or L-enantiomer) or an unnatural amino acid similar in structure to valine. In some embodiments, $Xaa_4$ is a valine (in the D- or L-enantiomer). Residue $Xaa_5$ can be any amino acid residue, and preferably a serine or a threonine (each independently selected to be the D- or L-enantiomer). In some embodiments, $Xaa_5$ is a serine (in the D- or L-enantiomer). Residue $Xaa_6$ can be any amino acid residue, and preferably a glutamine or a glutamic acid (each independently selected to be the D- or L-enantiomer).

In some embodiments, $Xaa_6$ is a glutamine (in the D- or L-enantiomer). In some specific embodiments, in the peptide compounds of the present disclosure $Xaa_5$ is a serine and $Xaa_6$ is a glutamine (both independently selected from the D- or L-enantiomer).

In some embodiments, the peptide compounds of the present disclosure can have the following amino acid core consensus and optionally include additional amino acid residues or modifications:

(formula Ia, SEQ ID NO: 24)
$Xaa_3$-$Xaa_4$-$Xaa_5$-$Xaa_6$ (formula Ib, SEQ ID NO: 25)
$Xaa_2$-$Xaa_3$-$Xaa_4$-$Xaa_5$-$Xaa_6$-$Xaa_7$
or (formula Ic, SEQ ID NO: 26)
$Xaa_1$-$Xaa_2$-$Xaa_3$-$Xaa_4$-$Xaa_5$-$Xaa_6$-$Xaa_7$-$Xaa_8$.

In the formula Ia, Ib, Ic, $Xaa_3$, $Xaa_4$, $Xaa_5$ and $Xaa_6$ are defined as above. Residue $Xaa_1$ can present or absent, when present $Xaa_1$ can be any amino acid residue. Residue $Xaa_2$ can be present or absent, $Xaa_2$ can be any amino acid residue, and preferably a serine (in the D- or L-enantiomer). Residue $Xaa_7$ can be present or absent, when present $Xaa_7$ can be any amino acid residue, and preferably a serine (in the D- or L-enantiomer). Residue $Xaa_8$ can be present or absent, when present $Xaa_8$ can be any amino acid residue.

The peptide compounds having the amino acid core of formula Ib include those having one of the following amino acid core (all derived from SEQ ID NO: 25, ✓ indicates that the amino acid residue is present, ✗ indicates that the amino acid residue is absent):

| $Xaa_2$ | $Xaa_3$ | $Xaa_4$ | $Xaa_5$ | $Xaa_6$ | $Xaa_7$ |
|---|---|---|---|---|---|
| ✓ | ✓ | ✓ | ✓ | ✓ | ✓ |
| ✗ | ✓ | ✓ | ✓ | ✓ | ✓ |
| ✓ | ✓ | ✓ | ✓ | ✓ | ✗ |
| ✗ | ✓ | ✓ | ✓ | ✓ | ✗ |

The peptide compounds having the amino acid core of formula Ic include those having one of the following amino acid core (all derived from SEQ ID NO: 26, ✓ indicates that the amino acid residue is present, ✗ indicates that the amino acid residue is absent):

| $Xaa_1$ | $Xaa_2$ | $Xaa_3$ | $Xaa_4$ | $Xaa_5$ | $Xaa_6$ | $Xaa_7$ | $Xaa_8$ |
|---|---|---|---|---|---|---|---|
| ✓ | ✓ | ✓ | ✓ | ✓ | ✓ | ✓ | ✓ |
| ✗ | ✓ | ✓ | ✓ | ✓ | ✓ | ✓ | ✓ |
| ✓ | ✗ | ✓ | ✓ | ✓ | ✓ | ✓ | ✓ |
| ✓ | ✓ | ✓ | ✓ | ✓ | ✓ | ✗ | ✓ |
| ✓ | ✓ | ✓ | ✓ | ✓ | ✓ | ✓ | ✗ |
| ✗ | ✗ | ✓ | ✓ | ✓ | ✓ | ✓ | ✓ |
| ✗ | ✓ | ✓ | ✓ | ✓ | ✓ | ✗ | ✓ |
| ✗ | ✓ | ✓ | ✓ | ✓ | ✓ | ✓ | ✗ |
| ✗ | ✗ | ✓ | ✓ | ✓ | ✓ | ✗ | ✓ |
| ✗ | ✗ | ✓ | ✓ | ✓ | ✓ | ✓ | ✗ |
| ✗ | ✗ | ✓ | ✓ | ✓ | ✓ | ✗ | ✗ |
| ✗ | ✓ | ✓ | ✓ | ✓ | ✓ | ✗ | ✗ |
| ✓ | ✗ | ✓ | ✓ | ✓ | ✓ | ✗ | ✓ |
| ✓ | ✗ | ✓ | ✓ | ✓ | ✓ | ✓ | ✗ |
| ✓ | ✗ | ✓ | ✓ | ✓ | ✓ | ✗ | ✗ |
| ✓ | ✓ | ✓ | ✓ | ✓ | ✓ | ✗ | ✗ |

Table 1 summarizes the amino acid core of the peptide compounds of the Examples. In some embodiments, the peptide compounds of the present disclosure have the amino acid core as described in Table 1 and optionally include additional amino acid residues or modifications (at the amino- or carboxy-terminus). In some embodiments, the peptide compounds of the present disclosure have the amino acid core as described in Table 1 and no additional amino acid residues or modifications (at the amino- or carboxy-terminus).

TABLE 1

Core amino acid sequence of the peptide compounds of the Example. The nomenclature on the first line of the table refers to the residues of Formula (I). The symbol "—" indicates that the amino acid residue is absent from the core amino acid sequence. The symbol "*" Indicates that the amino acid residue can be the L- or D-enantiomer. The compound # refers to the compound designation presented in Table 3.

| $Xaa_2$ | $Xaa_3$ | $Xaa_4$ | $Xaa_5$ | $Xaa_6$ | $Xaa_7$ | SEQ ID NO: | Compound # |
|---|---|---|---|---|---|---|---|
| — | K | V | S | Q | | 1 | 1, 2 |
| — | R | V* | T* | Q | | 2, 3, 4, 22 | 3, 4, 5, 6, 7, 10, 11, 12 |
| — | R | V* | S* | Q | | 5, 6, 7 | 14, 15, 16, 17 |
| — | R | I* | T | Q | | 8, 9 | 18, 20, 21, 22, 23 |
| — | K | I* | T | Q | | 10, 11 | 24, 25, 26, 27 |
| — | R | V | T | Q | S* | 12, 13 | 13 |
| — | R | I | T | Q | S* | 14, 15 | 19 |
| — | R | I | S | Q | | 16 | 28, 29 |
| S | R | V | T | Q | | 17 | 8 |
| — | R | L | T | Q | | 18 | 30, 31 |
| — | K | I* | S | Q | | 19, 20 | 32, 33, 34 |
| — | R | V | T | E | | 21 | 35, 36 |
| S* | R | V | T | Q | S* | 23 | 9 |
| —/S | K/R | V/I/L | S/T | Q/E | —/S | 24, 25, 26 | Consensus Ia, Ib, Ic |

The peptide compounds or amino acid core of the peptide compounds of the present disclosure can include only L-amino acid residues. In such embodiments, the peptide compounds and amino acid cores can be produced in a host, such as a cell or a cell line, which has been genetically engineered to express the peptide compound or amino acid core. Amino acid core or peptides compounds produced in a recombinant host can be substantially purified prior to being used to modulate steroid production or further chemically modified.

The peptide compounds of the present disclosure can have the following formula (II):

(II)
A-$Xaa_1$-$Xaa_A$-$Xaa_B$-$Xaa_2$-$Xaa_3$-$Xaa_4$-$Xaa_5$-

$Xaa_6$-$Xaa_7$-$Xaa_C$-$Xaa_D$-$Xaa_E$-$Xaa_8$-B

In the peptide compounds of formula II, residues A, $Xaa_1$, $Xaa_A$, $Xaa_B$, $Xaa_2$, $Xaa_7$, $Xaa_C$, $Xaa_D$, $Xaa_E$, $Xaa_8$, and B are optional and residues $Xaa_3$, $Xaa_4$, $Xaa_5$ and $Xaa_6$ are always present. As used in the context of the present disclosure, in the context of the peptides of formula (II), the "amino acid core" refers to "$Xaa_1$-$Xaa_A$-$Xaa_B$-$Xaa_2$-$Xaa_3$-$Xaa_4$-$Xaa_5$-$Xaa_6$-$Xaa_7$-$Xaa_C$-$Xaa_D$-$Xaa_E$-$Xaa_8$" and excludes the A and B residues. The symbol "-" in the amino acid core refers to a peptide bound that is formed between two contiguous amino acid residues. Furthermore, the "amino acid core" always includes "$Xaa_3$-$Xaa_4$-$Xaa_5$-$Xaa_6$".

As indicated above, at minimum, the amino acid core of the peptide compounds comprises "$Xaa_3$-$Xaa_4$-$Xaa_5$-$Xaa_6$". Residue $Xaa_3$ can be any amino acid residue, and preferably a lysine or an arginine (each independently selected to be the D- or L-enantiomer). In some embodiments, $Xaa_3$ is an arginine (in the D- or L-enantiomer). Residue $Xaa_4$ can be any amino acid residue, and preferably a valine, an isoleucine or a leucine (each independently selected to be the D- or L-enantiomer). In some embodiments, $Xaa_4$ is a valine (in the D- or L-enantiomer). Residue $Xaa_5$ can be any amino acid residue, and preferably a serine or a threonine (each independently selected to be the D- or L-enantiomer). In some embodiments, $Xaa_5$ is a serine (in the D- or L-enantiomer). Residue $Xaa_6$ can be any amino acid residue, and preferably a glutamine or a glutamic acid (each independently selected to be the D- or L-enantiomer). In some embodiments, $Xaa_6$ is a glutamine (in the D- or L-enantiomer). In some specific embodiments, in the peptide compounds of the present disclosure $Xaa_5$ is a serine and $Xaa_6$ is a glutamine (both independently selected from the D- or L-enantiomer).

In some embodiments, the peptide compounds of the present disclosure can have the following amino acid core consensus and optionally include additional amino acid residues or modifications:

(formula IIa, SEQ ID NO: 27)
$Xaa_1$-$Xaa_A$-$Xaa_B$-$Xaa_2$-$Xaa_3$-$Xaa_4$-$Xaa_5$-

$Xaa_6$-$Xaa_7$-$Xaa_8$;

(formula IIb, SEQ ID NO: 28)
$Xaa_1$-$Xaa_2$-$Xaa_3$-$Xaa_4$-$Xaa_5$-$Xaa_6$-$Xaa_7$-

$Xaa_C$-$Xaa_D$-$Xaa_E$-$Xaa_8$ (formula IIc, SEQ ID NO: 29)
$Xaa_1$-$Xaa_A$-$Xaa_B$-$Xaa_2$-$Xaa_3$-$Xaa_4$-$Xaa_4$-

$Xaa_6$-$Xaa_7$-$Xaa_C$-$Xaa_D$-$Xaa_E$-$Xaa_8$.

In the formula IIa, IIb, IIc, $Xaa_3$, $Xaa_4$, $Xaa_5$ and $Xaa_6$ are defined as above. Residue $Xaa_1$ can present or absent, when present $Xaa_1$ can be any amino acid residue. Residue $Xaa_A$ can be present or absent, when present $Xaa_A$ can be any amino acid residues, preferably a serine (in the D- or L-enantiomer). Residue $Xaa_B$ can be present or absent, when present $Xaa_B$ can be any amino acid residues, preferably a lysine (in the D- or L-enantiomer). Residue $Xaa_2$ can be present or absent, $Xaa_2$ can be any amino acid residue, and preferably a serine (in the D- or L-enantiomer). Residue $Xaa_7$ can be present or absent, when present $Xaa_7$ can be any amino acid residue, and preferably a serine (in the D- or L-enantiomer). Residue $Xaa_C$ can be present or absent, when present $Xaa_C$ can be any amino acid residues, preferably an asparagine (in the D- or L-enantiomer). Residue $Xaa_D$ can be present or absent, when present $Xaa_D$ can be any amino acid residues, preferably a phenylalanine (in the D- or L-enantiomer). Residue $Xaa_E$ can be present or absent, when present $Xaa_E$ can be any amino acid residues, preferably an alanine (in the D- or L-enantiomer). Residue $Xaa_8$ can be present or absent, when present $Xaa_8$ can be any amino acid residue.

The peptide compounds having the amino acid core of formula Ia include those having one of the following amino acid core (all derived from SEQ ID NO: 27, ✓ indicates that the amino acid residue is present, ✗ indicates that the amino acid residue is absent):

| $Xaa_1$ | $Xaa_A$ | $Xaa_B$ | $Xaa_2$ | $Xaa_3$ | $Xaa_4$ | $Xaa_5$ | $Xaa_6$ | $Xaa_7$ | $Xaa_8$ |
|---|---|---|---|---|---|---|---|---|---|
| ✓ | ✓ | ✓ | ✓ | ✓ | ✓ | ✓ | ✓ | ✓ | ✓ |
| ✓ | ✓ | ✓ | ✓ | ✓ | ✓ | ✓ | ✓ | ✓ | ✗ |

-continued

| Xaa$_1$ | Xaa$_A$ | Xaa$_B$ | Xaa$_2$ | Xaa$_3$ | Xaa$_4$ | Xaa$_5$ | Xaa$_6$ | Xaa$_7$ | Xaa$_8$ |
|---|---|---|---|---|---|---|---|---|---|
| ✓ | ✓ | ✓ | ✓ | ✓ | ✓ | ✓ | ✓ | x | ✓ |
| ✓ | ✓ | ✓ | ✓ | ✓ | ✓ | ✓ | ✓ | x | x |
| x | ✓ | ✓ | ✓ | ✓ | ✓ | ✓ | ✓ | ✓ | ✓ |
| x | ✓ | ✓ | ✓ | ✓ | ✓ | ✓ | ✓ | ✓ | x |
| x | ✓ | ✓ | ✓ | ✓ | ✓ | ✓ | ✓ | x | ✓ |
| x | ✓ | ✓ | ✓ | ✓ | ✓ | ✓ | ✓ | x | x |
| x | x | ✓ | ✓ | ✓ | ✓ | ✓ | ✓ | ✓ | ✓ |
| x | x | ✓ | ✓ | ✓ | ✓ | ✓ | ✓ | ✓ | x |
| x | x | ✓ | ✓ | ✓ | ✓ | ✓ | ✓ | x | ✓ |
| x | x | ✓ | ✓ | ✓ | ✓ | ✓ | ✓ | x | x |
| x | x | x | ✓ | ✓ | ✓ | ✓ | ✓ | ✓ | ✓ |
| x | x | x | ✓ | ✓ | ✓ | ✓ | ✓ | ✓ | x |
| x | x | x | ✓ | ✓ | ✓ | ✓ | ✓ | x | x |
| x | x | x | x | ✓ | ✓ | ✓ | ✓ | ✓ | ✓ |
| x | x | x | x | ✓ | ✓ | ✓ | ✓ | ✓ | x |
| x | x | x | x | ✓ | ✓ | ✓ | ✓ | x | ✓ |
| x | x | x | x | ✓ | ✓ | ✓ | ✓ | x | x |

The peptide compounds having the amino acid core of formula IIb include those having one of the following amino acid core (all derived from SEQ ID NO: 28, ✓ indicates that the amino acid residue is present, x indicates that the amino acid residue is absent):

| Xaa$_1$ | Xaa$_2$ | Xaa$_3$ | Xaa$_4$ | Xaa$_5$ | Xaa$_6$ | Xaa$_7$ | Xaa$_C$ | Xaa$_D$ | Xaa$_E$ | Xaa$_8$ |
|---|---|---|---|---|---|---|---|---|---|---|
| ✓ | ✓ | ✓ | ✓ | ✓ | ✓ | ✓ | ✓ | ✓ | ✓ | ✓ |
| ✓ | ✓ | ✓ | ✓ | ✓ | ✓ | ✓ | ✓ | ✓ | ✓ | x |
| ✓ | ✓ | ✓ | ✓ | ✓ | ✓ | ✓ | ✓ | ✓ | x | ✓ |
| ✓ | ✓ | ✓ | ✓ | ✓ | ✓ | ✓ | ✓ | ✓ | x | x |
| ✓ | ✓ | ✓ | ✓ | ✓ | ✓ | ✓ | ✓ | x | x | ✓ |
| ✓ | ✓ | ✓ | ✓ | ✓ | ✓ | ✓ | ✓ | x | x | x |
| ✓ | ✓ | ✓ | ✓ | ✓ | ✓ | ✓ | x | x | x | ✓ |
| ✓ | ✓ | ✓ | ✓ | ✓ | ✓ | ✓ | x | x | x | x |
| ✓ | ✓ | ✓ | ✓ | ✓ | ✓ | x | x | x | x | x |
| ✓ | ✓ | ✓ | ✓ | ✓ | ✓ | x | x | x | x | ✓ |
| x | ✓ | ✓ | ✓ | ✓ | ✓ | ✓ | ✓ | ✓ | ✓ | ✓ |
| x | ✓ | ✓ | ✓ | ✓ | ✓ | ✓ | ✓ | ✓ | ✓ | x |
| x | ✓ | ✓ | ✓ | ✓ | ✓ | ✓ | ✓ | ✓ | x | ✓ |
| x | ✓ | ✓ | ✓ | ✓ | ✓ | ✓ | ✓ | ✓ | x | x |
| x | ✓ | ✓ | ✓ | ✓ | ✓ | ✓ | ✓ | x | x | ✓ |
| x | ✓ | ✓ | ✓ | ✓ | ✓ | ✓ | ✓ | x | x | x |
| x | ✓ | ✓ | ✓ | ✓ | ✓ | ✓ | x | x | x | ✓ |
| x | ✓ | ✓ | ✓ | ✓ | ✓ | ✓ | x | x | x | x |
| x | ✓ | ✓ | ✓ | ✓ | ✓ | x | x | x | x | x |
| x | ✓ | ✓ | ✓ | ✓ | ✓ | x | x | x | x | ✓ |
| ✓ | x | ✓ | ✓ | ✓ | ✓ | ✓ | ✓ | ✓ | ✓ | ✓ |
| ✓ | x | ✓ | ✓ | ✓ | ✓ | ✓ | ✓ | ✓ | ✓ | x |
| ✓ | x | ✓ | ✓ | ✓ | ✓ | ✓ | ✓ | ✓ | x | ✓ |
| ✓ | x | ✓ | ✓ | ✓ | ✓ | ✓ | ✓ | ✓ | x | x |
| ✓ | x | ✓ | ✓ | ✓ | ✓ | ✓ | ✓ | x | x | ✓ |
| ✓ | x | ✓ | ✓ | ✓ | ✓ | ✓ | ✓ | x | x | x |
| ✓ | x | ✓ | ✓ | ✓ | ✓ | ✓ | x | x | x | ✓ |
| ✓ | x | ✓ | ✓ | ✓ | ✓ | ✓ | x | x | x | x |
| ✓ | x | ✓ | ✓ | ✓ | ✓ | x | x | x | x | ✓ |
| ✓ | x | ✓ | ✓ | ✓ | ✓ | x | x | x | x | x |

The peptide compounds having the amino acid core of formula IIc include those having one of the following amino acid core (all derived from SEQ ID NO: 29, ✓ indicates that the amino acid residue is present, x indicates that the amino acid residue is absent):

| Xaa$_1$ | Xaa$_A$ | Xaa$_B$ | Xaa$_2$ | Xaa$_3$ | Xaa$_4$ | Xaa$_5$ | Xaa$_6$ | Xaa$_7$ | Xaa$_C$ | Xaa$_D$ | Xaa$_E$ | Xaa$_8$ |
|---|---|---|---|---|---|---|---|---|---|---|---|---|
| ✓ | ✓ | ✓ | ✓ | ✓ | ✓ | ✓ | ✓ | ✓ | ✓ | ✓ | ✓ | ✓ |
| ✓ | x | ✓ | ✓ | ✓ | ✓ | ✓ | ✓ | ✓ | ✓ | ✓ | ✓ | ✓ |
| ✓ | x | x | ✓ | ✓ | ✓ | ✓ | ✓ | ✓ | ✓ | ✓ | ✓ | ✓ |
| x | x | x | ✓ | ✓ | ✓ | ✓ | ✓ | ✓ | ✓ | ✓ | ✓ | ✓ |
| ✓ | ✓ | ✓ | ✓ | ✓ | ✓ | ✓ | ✓ | ✓ | ✓ | ✓ | ✓ | x |
| ✓ | x | ✓ | ✓ | ✓ | ✓ | ✓ | ✓ | ✓ | ✓ | ✓ | ✓ | x |
| ✓ | x | x | ✓ | ✓ | ✓ | ✓ | ✓ | ✓ | ✓ | ✓ | ✓ | x |
| x | x | x | ✓ | ✓ | ✓ | ✓ | ✓ | ✓ | ✓ | ✓ | ✓ | x |
| ✓ | ✓ | ✓ | ✓ | ✓ | ✓ | ✓ | ✓ | ✓ | ✓ | ✓ | x | ✓ |
| ✓ | x | ✓ | ✓ | ✓ | ✓ | ✓ | ✓ | ✓ | ✓ | ✓ | x | ✓ |
| ✓ | x | x | ✓ | ✓ | ✓ | ✓ | ✓ | ✓ | ✓ | ✓ | x | ✓ |
| x | x | x | ✓ | ✓ | ✓ | ✓ | ✓ | ✓ | ✓ | ✓ | x | ✓ |
| ✓ | ✓ | ✓ | ✓ | ✓ | ✓ | ✓ | ✓ | ✓ | ✓ | ✓ | x | x |
| ✓ | x | ✓ | ✓ | ✓ | ✓ | ✓ | ✓ | ✓ | ✓ | ✓ | x | x |
| ✓ | x | x | ✓ | ✓ | ✓ | ✓ | ✓ | ✓ | ✓ | ✓ | x | x |
| x | x | x | ✓ | ✓ | ✓ | ✓ | ✓ | ✓ | ✓ | ✓ | x | x |

-continued

| Xaa₁ | Xaa₄ | Xaa_B | Xaa₂ | Xaa₃ | Xaa₄ | Xaa₅ | Xaa₆ | Xaa₇ | Xaa_C | Xaa_D | Xaa_E | Xaa₈ |
|---|---|---|---|---|---|---|---|---|---|---|---|---|
| ✓ | ✓ | ✓ | ✓ | ✓ | ✓ | ✓ | ✓ | ✓ | ✓ | x | x | ✓ |
| ✓ | x | ✓ | ✓ | ✓ | ✓ | ✓ | ✓ | ✓ | ✓ | x | x | ✓ |
| ✓ | x | x | ✓ | ✓ | ✓ | ✓ | ✓ | ✓ | ✓ | x | x | ✓ |
| x | x | x | ✓ | ✓ | ✓ | ✓ | ✓ | ✓ | ✓ | x | x | ✓ |
| ✓ | ✓ | ✓ | ✓ | ✓ | ✓ | ✓ | ✓ | ✓ | ✓ | x | x | x |
| ✓ | x | ✓ | ✓ | ✓ | ✓ | ✓ | ✓ | ✓ | ✓ | x | x | x |
| ✓ | x | x | ✓ | ✓ | ✓ | ✓ | ✓ | ✓ | ✓ | x | x | x |
| x | x | x | ✓ | ✓ | ✓ | ✓ | ✓ | ✓ | ✓ | x | x | x |
| ✓ | ✓ | ✓ | ✓ | ✓ | ✓ | ✓ | ✓ | ✓ | x | x | x | ✓ |
| ✓ | x | ✓ | ✓ | ✓ | ✓ | ✓ | ✓ | ✓ | x | x | x | ✓ |
| ✓ | x | x | ✓ | ✓ | ✓ | ✓ | ✓ | ✓ | x | x | x | ✓ |
| x | x | x | ✓ | ✓ | ✓ | ✓ | ✓ | ✓ | x | x | x | ✓ |
| ✓ | ✓ | ✓ | ✓ | ✓ | ✓ | ✓ | ✓ | ✓ | x | x | x | x |
| ✓ | x | ✓ | ✓ | ✓ | ✓ | ✓ | ✓ | ✓ | x | x | x | x |
| ✓ | x | x | ✓ | ✓ | ✓ | ✓ | ✓ | ✓ | x | x | x | x |
| x | x | x | ✓ | ✓ | ✓ | ✓ | ✓ | ✓ | x | x | x | x |
| ✓ | ✓ | ✓ | ✓ | ✓ | ✓ | ✓ | ✓ | x | x | x | x | x |
| ✓ | x | ✓ | ✓ | ✓ | ✓ | ✓ | ✓ | x | x | x | x | x |
| ✓ | x | x | ✓ | ✓ | ✓ | ✓ | ✓ | x | x | x | x | x |
| x | x | x | ✓ | ✓ | ✓ | ✓ | ✓ | x | x | x | x | x |
| ✓ | ✓ | ✓ | ✓ | ✓ | ✓ | ✓ | ✓ | x | x | x | x | ✓ |
| ✓ | x | ✓ | ✓ | ✓ | ✓ | ✓ | ✓ | x | x | x | x | ✓ |
| ✓ | x | x | ✓ | ✓ | ✓ | ✓ | ✓ | x | x | x | x | ✓ |
| x | x | x | ✓ | ✓ | ✓ | ✓ | ✓ | x | x | x | x | ✓ |
| x | ✓ | ✓ | ✓ | ✓ | ✓ | ✓ | ✓ | ✓ | ✓ | ✓ | ✓ | ✓ |
| x | x | ✓ | ✓ | ✓ | ✓ | ✓ | ✓ | ✓ | ✓ | ✓ | ✓ | ✓ |
| x | x | x | ✓ | ✓ | ✓ | ✓ | ✓ | ✓ | ✓ | ✓ | ✓ | ✓ |
| x | ✓ | ✓ | ✓ | ✓ | ✓ | ✓ | ✓ | ✓ | ✓ | ✓ | ✓ | x |
| x | x | ✓ | ✓ | ✓ | ✓ | ✓ | ✓ | ✓ | ✓ | ✓ | ✓ | x |
| x | x | x | ✓ | ✓ | ✓ | ✓ | ✓ | ✓ | ✓ | ✓ | ✓ | x |
| x | ✓ | ✓ | ✓ | ✓ | ✓ | ✓ | ✓ | ✓ | ✓ | ✓ | x | ✓ |
| x | x | ✓ | ✓ | ✓ | ✓ | ✓ | ✓ | ✓ | ✓ | ✓ | x | ✓ |
| x | x | x | ✓ | ✓ | ✓ | ✓ | ✓ | ✓ | ✓ | ✓ | x | ✓ |
| x | ✓ | ✓ | ✓ | ✓ | ✓ | ✓ | ✓ | ✓ | ✓ | ✓ | x | x |
| x | x | ✓ | ✓ | ✓ | ✓ | ✓ | ✓ | ✓ | ✓ | ✓ | x | x |
| x | x | x | ✓ | ✓ | ✓ | ✓ | ✓ | ✓ | ✓ | ✓ | x | x |
| x | ✓ | ✓ | ✓ | ✓ | ✓ | ✓ | ✓ | ✓ | ✓ | x | x | ✓ |
| x | x | ✓ | ✓ | ✓ | ✓ | ✓ | ✓ | ✓ | ✓ | x | x | ✓ |
| x | x | x | ✓ | ✓ | ✓ | ✓ | ✓ | ✓ | ✓ | x | x | ✓ |
| x | ✓ | ✓ | ✓ | ✓ | ✓ | ✓ | ✓ | ✓ | ✓ | x | x | x |
| x | x | ✓ | ✓ | ✓ | ✓ | ✓ | ✓ | ✓ | ✓ | x | x | x |
| x | x | x | ✓ | ✓ | ✓ | ✓ | ✓ | ✓ | ✓ | x | x | x |
| x | ✓ | ✓ | ✓ | ✓ | ✓ | ✓ | ✓ | ✓ | x | x | x | ✓ |
| x | x | ✓ | ✓ | ✓ | ✓ | ✓ | ✓ | ✓ | x | x | x | ✓ |
| x | x | x | ✓ | ✓ | ✓ | ✓ | ✓ | ✓ | x | x | x | ✓ |
| x | ✓ | ✓ | ✓ | ✓ | ✓ | ✓ | ✓ | ✓ | x | x | x | x |
| x | x | ✓ | ✓ | ✓ | ✓ | ✓ | ✓ | ✓ | x | x | x | x |
| x | x | x | ✓ | ✓ | ✓ | ✓ | ✓ | ✓ | x | x | x | x |
| x | ✓ | ✓ | ✓ | ✓ | ✓ | ✓ | ✓ | x | x | x | x | ✓ |
| x | x | ✓ | ✓ | ✓ | ✓ | ✓ | ✓ | x | x | x | x | ✓ |
| x | x | x | ✓ | ✓ | ✓ | ✓ | ✓ | x | x | x | x | ✓ |
| x | ✓ | ✓ | ✓ | ✓ | ✓ | ✓ | ✓ | x | x | x | x | x |
| x | x | ✓ | ✓ | ✓ | ✓ | ✓ | ✓ | x | x | x | x | x |
| x | x | x | ✓ | ✓ | ✓ | ✓ | ✓ | x | x | x | x | x |
| ✓ | x | x | x | ✓ | ✓ | ✓ | ✓ | ✓ | ✓ | ✓ | ✓ | ✓ |
| ✓ | x | x | x | ✓ | ✓ | ✓ | ✓ | ✓ | ✓ | ✓ | ✓ | x |
| ✓ | x | x | x | ✓ | ✓ | ✓ | ✓ | ✓ | ✓ | ✓ | x | ✓ |
| ✓ | x | x | x | ✓ | ✓ | ✓ | ✓ | ✓ | ✓ | ✓ | x | x |
| ✓ | x | x | x | ✓ | ✓ | ✓ | ✓ | ✓ | ✓ | x | x | ✓ |
| ✓ | x | x | x | ✓ | ✓ | ✓ | ✓ | ✓ | ✓ | x | x | x |

-continued

| Xaa$_1$ | Xaa$_A$ | Xaa$_B$ | Xaa$_2$ | Xaa$_3$ | Xaa$_4$ | Xaa$_5$ | Xaa$_6$ | Xaa$_7$ | Xaa$_C$ | Xaa$_D$ | Xaa$_E$ | Xaa$_8$ |
|---|---|---|---|---|---|---|---|---|---|---|---|---|
| ✓ | x | x | x | ✓ | ✓ | ✓ | ✓ | ✓ | x | x | x | ✓ |
| ✓ | x | x | x | ✓ | ✓ | ✓ | ✓ | ✓ | x | x | x | x |
| ✓ | x | x | x | ✓ | ✓ | ✓ | ✓ | x | x | x | x | ✓ |
| ✓ | x | x | x | ✓ | ✓ | ✓ | ✓ | x | x | x | x | x |

Table 2 summarizes the amino acid core of some of the peptide compounds of the Examples. In some embodiments, the peptide compounds of the present disclosure have the amino acid core as described in Table 2 and optionally include additional amino acid residues or modifications (at the amino- or carboxy-terminus). In some embodiments, the peptide compounds of the present disclosure have the amino acid core as described in Table 1 and no additional amino acid residues or modifications (at the amino- or carboxy-terminus).

TABLE 2

Core amino acid sequence of the peptide compounds of the Example. The nomenclature on the first line of the table refers to the residues of Formula (II). The symbol "--" indicates that the amino acid residue is absent from the core amino acid sequence. The symbol "*" Indicates that the amino acid residue can be the L- or D-enantiomer. The compound # refers to the compound designation presented in Table 3.

| Xaa$_A$ | Xaa$_B$ | Xaa$_2$ | Xaa$_3$ | Xaa$_4$ | Xaa$_5$ | Xaa$_6$ | Xaa$_7$ | Xaa$_C$ | Xaa$_D$ | Xaa$_E$ | SEQ ID NO: |
|---|---|---|---|---|---|---|---|---|---|---|---|
|   |   |   | R | V | T | Q |   |   |   |   | 2 |
|   |   | S | R | V | T | Q |   |   |   |   | 17 |
|   |   |   | R | V | T | Q | S |   |   |   | 12 |
|   | K | S | R | V | T | Q | S |   |   |   | 30 |
|   |   | S | R | V | T | Q | S | N | F |   | 31 |
|   | K | S | R | V | T | Q | S | N | F | A | 32 |
| S | K | S | R | V | T | Q | S | N | F |   | 33 |
| S | K | S | R | V | T | Q | S | N | F | A | 34 |

The peptide compounds or amino acid core of the peptide compounds of the present disclosure can include only L-amino acid residues. In such embodiments, the peptide compounds and amino acid cores can be produced in a host, such as a cell or a cell line, which has been genetically engineered to express the peptide compound or amino acid core. Amino acid core or peptides compounds produced in a recombinant host can be substantially purified prior to being used to modulate steroid production or further chemically modified.

Alternatively, the peptide compounds or amino acid core of the peptide compounds of the present disclosure can include at least one and, in some embodiments, only D-amino acid residues. In such embodiment, the peptide compounds and amino acids core can be synthesized chemically and substantially purified prior to being used to modulate steroid production or further chemically modified.

In some embodiments, the amino acid core can be used without further modification as a peptide compound. Alternatively, the amino acid core can be modified, at its amino- and/or carboxy-terminus to further improve the therapeutic profile of the peptide compounds. These additional modifications are labelled as residues "A" and "B" in the peptide compounds of formula I. Modifications "A" and "B" can be any modifications made to the amino acid core which, in some embodiments, will retain the ability of the peptide compound to promote endogenous testosterone synthesis and increase the circulation half-life of the peptide compounds (when compared to a corresponding compound lacking the modifications). Residues A and B are independently selected from an amide cap, an acetyl cap, an uncharged, hydrophilic and/or non-toxic polymer (such as a polyethylene glycol polymer). In embodiments in which it is desirable to locate the peptide compound in a cell or an organism, residues A and B can be a label, such as a biotin or fluorescent label or an isotope (radioactive or non-radioactive) label.

In some embodiments, the peptide compounds of the present disclosure include residue A and can have the following formula:

(I)
A-Xaa$_1$-Xaa$_2$-Xaa$_3$-Xaa$_4$-Xaa$_5$-Xaa$_6$-Xaa$_7$-Xaa$_8$-B (Id)
A-Xaa$_1$-Xaa$_2$-Xaa$_3$-Xaa$_4$-Xaa$_5$-Xaa$_6$-Xaa$_7$-Xaa$_8$

In such embodiments, residues A, Xaa$_1$ (when present), Xaa$_2$ (when present), Xaa$_3$, Xaa$_4$, Xaa$_5$, Xaa$_6$, Xaa$_7$ (when present), Xaa$_8$ (when present) and B (when present) are defined as above.

In some embodiments, the peptide compounds of the present disclosure do not include residue A and can have the following formula:

(Ie)
Xaa$_1$-Xaa$_2$-Xaa$_3$-Xaa$_4$-Xaa$_5$-Xaa$_6$-Xaa$_7$-Xaa$_8$-B (If)
Xaa$_1$-Xaa$_2$-Xaa$_3$-Xaa$_4$-Xaa$_5$-Xaa$_6$-Xaa$_7$-Xaa$_8$

In such embodiments, residues Xaa$_1$ (when present), Xaa$_2$ (when present), Xaa$_3$, Xaa$_4$, Xaa$_5$, Xaa$_6$, Xaa$_7$ (when present), Xaa$_8$ (when present) and B (when present) are defined as above.

In some embodiments, the peptide compounds of the present disclosure include residue B and can have the following formula:

(I)
A-Xaa$_1$-Xaa$_2$-Xaa$_3$-Xaa$_4$-Xaa$_5$-Xaa$_6$-Xaa$_7$-Xaa$_8$-B (Ie)
Xaa$_1$-Xaa$_2$-Xaa$_3$-Xaa$_4$-Xaa$_5$-Xaa$_6$-Xaa$_7$-Xaa$_8$-B

In such embodiments, residues A (when present), Xaa$_1$ (when present), Xaa$_2$ (when present), Xaa$_3$, Xaa$_4$, Xaa$_5$, Xaa$_6$, Xaa$_7$ (when present), Xaa$_8$ (when present) and B are defined as above.

In some embodiments, the peptide compounds of the present disclosure do not include residue B and can have the following formula:

(Id)
A-Xaa$_1$-Xaa$_2$-Xaa$_3$-Xaa$_4$-Xaa$_5$-Xaa$_6$-Xaa$_7$-Xaa$_8$ (If)
Xaa$_1$-Xaa$_2$-Xaa$_3$-Xaa$_4$-Xaa$_5$-Xaa$_6$-Xaa$_7$-Xaa$_8$

In such embodiments, residues A (when present), Xaa$_1$ (when present), Xaa$_2$ (when present), Xaa$_3$, Xaa$_4$, Xaa$_5$, Xaa$_6$, Xaa$_7$ (when present) and Xaa$_8$ (when present) are defined as above.

In some embodiments, the peptide compounds of the present disclosure include residue A and can have the following formula:

(II)
A-Xaa$_1$-Xaa$_A$-Xaa$_B$-Xaa$_2$-Xaa$_3$-Xaa$_4$-Xaa$_5$-
Xaa$_6$-Xaa$_7$-Xaa$_C$-Xaa$_D$-Xaa$_E$-Xaa$_8$-B (IId)
A-Xaa$_1$-Xaa$_A$-Xaa$_B$-Xaa$_2$-Xaa$_3$-Xaa$_4$-Xaa$_5$-
Xaa$_6$-Xaa$_7$-Xaa$_C$-Xaa$_D$-Xaa$_E$-Xaa$_8$

In such embodiments, residues A, Xaa$_1$ (when present), Xaa$_A$ (when present), Xaa$_B$ (when present) Xaa$_2$ (when present), Xaa$_3$, Xaa$_4$, Xaa$_5$, Xaa$_6$, Xaa$_7$ (when present), Xaa$_C$ (when present), Xaa$_D$ (when present), Xaa$_E$ (when present), Xaa$_8$ (when present) and B (when present) are defined as above.

In some embodiments, the peptide compounds of the present disclosure do not include residue A and can have the following formula:

(IIe)
Xaa$_1$-Xaa$_A$-Xaa$_B$-Xaa$_2$-Xaa$_3$-Xaa$_4$-Xaa$_5$-
Xaa$_6$-Xaa$_7$-Xaa$_C$-Xaa$_D$-Xaa$_E$-Xaa$_8$-B (IIf)
Xaa$_1$-Xaa$_A$-Xaa$_B$-Xaa$_2$-Xaa$_3$-Xaa$_4$-Xaa$_5$-
Xaa$_6$-Xaa$_7$-Xaa$_C$-Xaa$_D$-Xaa$_E$-Xaa$_8$

In such embodiments, residues Xaa$_1$ (when present), Xaa$_A$ (when present), Xaa$_B$ (when present) Xaa$_2$ (when present), Xaa$_3$, Xaa$_4$, Xaa$_5$, Xaa$_6$, Xaa$_7$ (when present), Xaa$_C$ (when present), Xaa$_D$ (when present), Xaa$_E$ (when present), Xaa$_8$ (when present) and B (when present) are defined as above.

In some embodiments, the peptide compounds of the present disclosure include residue B and can have the following formula:

(II)
A-Xaa$_1$-Xaa$_A$-Xaa$_B$-Xaa$_2$-Xaa$_3$-Xaa$_4$-Xaa$_5$-
Xaa$_6$-Xaa$_7$-Xaa$_C$-Xaa$_D$-Xaa$_E$-Xaa$_8$-B (IIe)
Xaa$_1$-Xaa$_A$-Xaa$_B$-Xaa$_2$-Xaa$_3$-Xaa$_4$-Xaa$_5$-
Xaa$_6$-Xaa$_7$-Xaa$_C$-Xaa$_D$-Xaa$_E$-Xaa$_8$-B

In such embodiments, residues A (when present), Xaa$_1$ (when present), Xaa$_A$ (when present), Xaa$_B$ (when present) Xaa$_2$ (when present), Xaa$_3$, Xaa$_4$, Xaa$_5$, Xaa$_6$, Xaa$_7$ (when present), Xaa$_C$ (when present), Xaa$_D$ (when present), Xaa$_E$ (when present), Xaa$_8$ (when present) and B (when present) are defined as above.

In some embodiments, the peptide compounds of the present disclosure do not include residue B and can have the following formula:

(IId)
A-Xaa$_1$-Xaa$_A$-Xaa$_B$-Xaa$_2$-Xaa$_3$-Xaa$_4$-Xaa$_5$-
Xaa$_6$-Xaa$_7$-Xaa$_C$-Xaa$_D$-Xaa$_E$-Xaa$_8$ (IIf)
Xaa$_1$-Xaa$_A$-Xaa$_B$-Xaa$_2$-Xaa$_3$-Xaa$_4$-Xaa$_5$-
Xaa$_6$-Xaa$_7$-Xaa$_C$-Xaa$_D$-Xaa$_E$-Xaa$_8$

In such embodiments, residues A (when present), Xaa$_1$ (when present), Xaa$_A$ (when present), Xaa$_B$ (when present) Xaa$_2$ (when present), Xaa$_3$, Xaa$_4$, Xaa$_5$, Xaa$_6$, Xaa$_7$ (when present), Xaa$_C$ (when present), Xaa$_D$ (when present), Xaa$_E$ (when present) and Xaa$_8$ (when present) are defined as above.

Combinations of Peptide Compounds

The present disclosure provides combination of peptide compounds for increasing endogenous steroid production, including endogenous testosterone production. The combination comprises at least two or more distinct peptide compounds. In the combinations of the present disclosure, the peptide compounds are considered distinct because they structurally differ from one another. The peptide compounds of the combination are considered "distinct" if they differ with respect to at least one of the amino acid identity in their amino acid core, the length of consecutive amino acid residues in their amino acid core, the amino acid enantiomer used of the amino, the presence, absence and identity of the modification made at their amino-terminus or the presence, absence and identity of the modification(s) made at their carboxy-terminus. In some embodiments, the combination comprises no more than two peptide compounds.

In order to achieve the desired therapeutic endpoint (e.g., increase in endogenous steroid production), it is possible to provide the peptide compounds of the combination in the same dosage form or in discrete dosage forms. The peptide compounds of the present disclosure can be (or intended to be) co-administered or administered sequentially.

The combination of the present disclosure encompass the combination of at least two distinct peptide compounds of formula (I), (Ia), (Ib), (Ic), (Id), (Ie), (If), (II), (IIa), (IIb), (IIc), (IId), (IIe), (IIf), described in Table 1, 2 or 3. In some specific embodiments, the combinations of the present disclosure concerns a combination including (or consisting essentially of) at least two distinct peptide compounds as described in Table 3. For example, the combination includes (or consists essentially of) the following pairs of peptide compounds described in Table 3: 1 and 2, 1 and 3, 1 and 4, 1 and 5, 1 and 6, 1 and 7, 1 and 8, 1 and 9, 1 and 10, 1 and 11, 1 and 12, 1 and 13, 1 and 14, 1 and 15, 1 and 16, 1 and 17, 1 and 18, 1 and 19, 1 and 20, 1 and 21, 1 and 22, 1 and 23, 1 and 24, 1 and 25, 1 and 26, 1 and 27, 1 and 28, 1 and 29, 1 and 30, 1 and 31, 1 and 32, 1 and 33, 1 and 34, 1 and 35, 1 and 36, 1 and 37, 1 and 38, 1 and 39, 2 and 3, 2 and 4, 2 and 5, 2 and 6, 2 and 7, 2 and 8, 2 and 9, 2 and 10, 2 and 11, 2 and 12, 2 and 13, 2 and 14, 2 and 15, 2 and 16, 2 and 17, 2 and 18, 2 and 19, 2 and 20, 2 and 21, 2 and 22, 2 and 23, 2 and 24, 2 and 25, 2 and 26, 2 and 27, 2 and 28, 2 and 29, 2 and 30, 2 and 31, 2 and 32, 2 and 33, 2 and 34, 2 and 35, 2 and 36, 2 and 37, 2 and 38, 2 and 39, 3 and 4, 3 and 5, 3 and 6, 3 and 7, 3 and 8, 3 and 9, 3 and 10, 3 and 11, 3 and 12, 3 and 13, 3 and 14, 3 and 15, 3 and 16, 3 and 17, 3 and 18, 3 and 19, 3 and 20, 3 and 21, 3 and 22, 3 and 23, 3 and 24, 3 and 25, 3 and 26, 3 and 27, 3 and 28, 3 and 29, 3 and 30, 3 and 31, 3 and 32, 3 and 33, 3 and 34, 3 and 35, 3 and 36, 3 and 37, 3 and 38, 3 and 39, 4 and 5, 4 and 6, 4 and 7, 4 and 8, 4 and 9, 4 and 10, 4 and 11, 4 and 12, 4 and 13, 4 and 14, 4 and 15, 4 and 16, 4 and 17, 4 and 18, 4 and 19, 4 and 20, 4 and 21, 4 and 22, 4 and 23, 4 and 24, 4 and 25, 4 and 26, 4 and 27, 4 and 28, 4 and 29, 4 and 30, 4 and 31, 4 and 32, 4 and 33, 4 and 34, 4 and 35, 4 and 36, 4 and 37, 4 and 38, 4 and 39, 5 and 6, 5 and 7, 5 and 8, 5 and 9, 5 and 10, 5 and 11, 5 and 12, 5 and 13, 5 and 14, 5 and 15, 5 and 16, 5 and 17, 5 and 18, 5 and 19, 5 and 20, 5 and 21, 5 and 22, 5 and 23, 5 and 24, 5 and 25, 5 and 26, 5 and 27, 5 and 28, 5 and 29, 5 and 30, 5 and 31, 5 and 32, 5 and 33, 5 and 34, 5 and 35, 5 and 36, 5 and 37, 5 and 38, 5 and 39, 6 and 7, 6 and 8, 6 and 9, 6 and 10, 6 and 11, 6 and 12, 6 and 13, 6 and 14, 6 and 15, 6 and 16, 6 and 17, 6 and 18, 6 and 19, 6 and 20, 6 and 21, 6 and 22, 6 and 23, 6 and 24, 6 and 25, 6 and 26, 6 and 27, 6 and 28, 6 and 29, 6 and 30, 6 and 31, 6 and 32, 6 and 33, 6 and 34, 6 and 35, 6 and 36, 6 and 37, 6 and 38, 6 and 39, 7 and 8, 7 and 9, 7 and 10, 7 and 11, 7 and 12, 7 and 13, 7 and 14, 7 and 15, 7 and 16, 7 and 17, 7 and 18, 7 and 19, 7 and 20, 7 and 21, 7 and 22, 7 and 23, 7 and 24, 7 and 25, 7 and 26, 7 and 27, 7 and 28, 7 and 29, 7 and 30, 7 and 31, 7 and 32, 7 and 33, 7 and 34, 7 and 35, 7 and 36, 7 and 37, 7 and 38, 7 and 39, 8 and 9, 8 and 10, 8 and 11, 8 and 12, 8 and 13, 8 and 14, 8 and 15, 8 and 16, 8 and 17, 8 and 18, 8 and 19, 8 and 20, 8 and 21, 8 and 22, 8 and 23, 8 and 24, 8 and 25, 8 and 26, 8 and 27, 8 and 28, 8 and 29, 8 and 30, 8 and 31, 8 and 32, 8 and 33, 8 and 34, 8 and 35, 8 and 36, 8 and 37, 8 and 38, 8 and 39, 9 and 10, 9 and 11, 9 and 12, 9 and 13, 9 and 14, 9 and 15, 9 and 16, 9 and 17, 9 and 18, 9 and 19, 9 and 20, 9 and 21, 9 and 22, 9 and 23, 9 and 24, 9 and 25, 9 and 26, 9 and 27, 9 and 28, 9 and 29, 9 and 30, 9 and 31, 9 and 32, 9 and 33, 9 and 34, 9 and 35, 9 and 36, 9 and 37, 9 and 38, 9 and 39, 10 and 11, 10 and 12, 10 and 13, 10 and 14, 10 and 15, 10 and 16, 10 and 17, 10 and 18, 10 and 19, 10 and 20, 10 and 21, 10 and 22, 10 and 23, 10 and 24, 10 and 25, 10 and 26, 10 and 27, 10 and 28, 10 and 29, 10 and 30, 10 and 31, 10 and 32, 10 and 33, 10 and 34, 10 and 35, 10 and 36, 10 and 37, 10 and 38, 10 and 39, 11 and 12, 11 and 13, 11 and 14, 11 and 15, 11 and 16, 11 and 17, 11 and 18, 11 and 19, 11 and 20, 11 and 21, 11 and 22, 11 and 23, 11 and 24, 11 and 25, 11 and 26, 11 and 27, 11 and 28, 11 and 29, 11 and 30, 11 and 31, 11 and 32, 11 and 33, 11 and 34, 11 and 35, 11 and 36, 11 and 37, 11 and 38, 11 and 39, 12 and 13, 12 and 14, 12 and 15, 12 and 16, 12 and 17, 12 and 18, 12 and 19, 12 and 20, 12 and 21, 12 and 22, 12 and 23, 12 and 24, 12 and 25, 12 and 26, 12 and 27, 12 and 28, 12 and 29, 12 and 30, 12 and 31, 12 and 32, 12 and 33, 12 and 34, 12 and 35, 12 and 36, 12 and 37, 12 and 38, 12 and 39, 13 and 14, 13 and 15, 13 and 16, 13 and 17, 13 and 18, 13 and 19, 13 and 20, 13 and 21, 13 and 22, 13 and 23, 13 and 24, 13 and 25, 13 and 26, 13 and 27, 13 and 28, 13 and 29, 13 and 30, 13 and 31, 13 and 32, 13 and 33, 13 and 34, 13 and 35, 13 and 36, 13 and 37, 13 and 38, 13 and 39, 14 and 15, 14 and 16, 14 and 17, 14 and 18, 14 and 19, 14 and 20, 14 and 21, 14 and 22, 14 and 23, 14 and 24, 14 and 25, 14 and 26, 14 and 27, 14 and 28, 14 and 29, 14 and 30, 14 and 31, 14 and 32, 14 and 33, 14 and 34, 14 and 35, 14 and 36, 14 and 37, 14 and 38, 14 and 39, 15 and 16, 15 and 17, 15 and 18, 15 and 19, 15 and 20, 15 and 21, 15 and 22, 15 and 23, 15 and 24, 15 and 25, 15 and 26, 15 and 27, 15 and 28, 15 and 29, 15 and 30, 15 and 31, 15 and 32, 15 and 33, 15 and 34, 15 and 35, 15 and 36, 15 and 37, 15 and 38, 15 and 39, 16 and 17, 16 and 18, 16 and 19, 16 and 20, 16 and 21, 16 and 22, 16 and 23, 16 and 24, 16 and 25, 16 and 26, 16 and 27, 16 and 28, 16 and 29, 16 and 30, 16 and 31, 16 and 32, 16 and 33, 16 and 34, 16 and 35, 16 and 36, 16 and 37, 16 and 38, 16 and 39, 17 and 18, 17 and 19, 17 and 20, 17 and 21, 17 and 22, 17 and 23, 17 and 24, 17 and 25, 17 and 26, 17 and 27, 17 and 28, 17 and 29, 17 and 30, 17 and 31, 17 and 32, 17 and 33, 17 and 34, 17 and 35, 17 and 36, 17 and 37, 17 and 38, 17 and 39, 18 and 19, 18 and 20, 18 and 21, 18 and 22, 18 and 23, 18 and 24, 18 and 25, 18 and 26, 18 and 27, 18 and 28, 18 and 29, 18 and 30, 18 and 31, 18 and 32, 18 and 33, 18 and 34, 18 and 35, 18 and 36, 18 and 37, 18 and 38, 18 and 39, 19 and 20, 19 and 21, 19 and 22, 19 and 23, 19 and 24, 19 and 25, 19 and 26, 19 and 27, 19 and 28, 19 and 29, 19 and 30, 19 and 31, 19 and 32, 19 and 33, 19 and 34, 19 and 35, 19 and 36, 19 and 37, 19 and 38, 19 and 39, 20 and 21, 20 and 22, 20 and 23, 20 and 24, 20 and 25, 20 and 26, 20 and 27, 20 and 28, 20 and 29, 20 and 30, 20 and 31, 20 and 32, 20 and 33, 20 and 34, 20 and 35, 20 and 36, 20 and 37, 20 and 38, 20 and 39, 21 and 22, 21 and 23, 21 and 24, 21 and 25, 21 and 26, 21 and 27, 21 and 28, 21 and 29, 21 and 30, 21 and 31, 21 and 32, 21 and 33, 21 and 34, 21 and 35, 21 and 36, 21 and 37, 21 and 38, 21 and 39, 22 and 23, 22 and 24, 22 and 25, 22 and 26, 22 and 27, 22 and 28, 22 and 29, 22 and 30, 22 and 31, 22 and 32, 22 and 33, 22 and 34, 22 and 35, 22 and 36, 22 and 37, 22 and 38, 22 and 39, 23 and 24, 23 and 25, 23 and 26, 23 and 27, 23 and 28, 23 and 29, 23 and 30, 23 and 31, 23 and 32, 23 and 33, 23 and 34, 23 and 35, 23 and 36, 23 and 37, 23 and 28, 23 and 39, 24 and 25, 24 and 26, 24 and 27, 24 and 28, 24 and 29, 24 and 30, 24 and 31, 24 and 32, 24 and 33, 24 and 34, 24 and 35, 24 and 36, 24 and 37, 24 and 38, 24 and 39, 25 and 26, 25 and 27, 25 and 28, 25 and 29, 25 and 30, 25 and 31, 25 and 32, 25 and 33, 25 and 34, 25 and 35, 25 and 36, 25 and 37, 25 and 38, 25 and 39, 26 and 27, 26 and 28, 26 and 29, 26 and 30, 26 and 31, 26 and 32, 26 and 33, 26 and 34, 26 and 35, 26 and 36, 26 and 37, 26 and 38, 26 and 39, 27 and 28, 27 and 29, 27 and 30, 27 and 31, 27 and 32, 27 and 33, 27 and 34, 27 and 35, 27 and 36, 27 and 37, 27 and 38, 27 and 39, 28 and 29, 28 and 30, 28 and 31, 28 and 32, 28 and 33, 28 and 34, 28 and 35, 28 and 36, 28 and 37, 28 and 38, 28 and 39, 29 and 30, 29 and 31, 29 and 32, 29 and 33, 29 and 34, 29 and 35, 29 and 36, 29 and 37, 29 and 38, 29 and 39, 30 and 31, 30 and 32, 30 and 33, 30 and 34, 30 and 35, 30 and 36, 30 and 37, 30 and 38, 30 and 39, 31 and 32, 31 and 33, 31 and 34, 31 and 35, 31 and 36, 31 and 37, 31 and 38, 31 and 39, 32 and 33, 32 and 34, 32 and 35, 32 and 36, 32 and 37, 32 and 38, 32 and 39, 33 and 34, 33 and 35, 33 and 36, 33 and 37, 33 and 38, 33 and 39, 34 and 35, 34 and 36, 34 and 37, 34 and 38, 34 and 39, 35 and 36, 35 and 37, 35 and 38, 35 and 39, 36 and 37, 36 and 38, 36 and 39, 37 and 38, 37 and 39 or 38 and 39.

In an embodiment, the combination comprises or consists essentially of the peptide compound 20 and the peptide compound 1. In another embodiment, the combination comprises or consists essentially of the peptide compound 20 and the peptide compound 10. In a further embodiment, the combination comprises or consists essentially of the peptide compound 20 and the peptide compound 19. In yet another embodiment, the combination comprises or consists essentially of the peptide compound 1 and the peptide compound 11. In still another embodiment, the combination comprises or consists essentially of the peptide compound 1 and the peptide compound 18. In yet another embodiment, the combination comprises or consists essentially of the peptide compound 11 and the peptide compound 18. In yet a further embodiment, the combination comprises or consists essentially of the peptide compound 20 and the peptide compound 18. In yet a further embodiment, the combination comprises or consists essentially of the peptide compound 20 and the peptide compound 3. In yet a further embodiment, the combination comprises or consists essentially of the peptide compound 1 and the peptide compound 19. In yet a further embodiment, the combination comprises or consists essentially of the peptide compound 1 and the peptide compound 13. In yet a further embodiment, the combination comprises or consists essentially of the peptide compound 10 and the peptide compound 19. In yet a further embodiment, the combination comprises or consists essentially of the peptide compound 10 and the peptide compound 3. In yet a further embodiment, the combination comprises or consists essentially of the peptide compound 19 and the peptide compound 3. In yet a further embodiment, the combination comprises or consists essentially of the peptide compound 18 and the peptide compound 3. In yet a further embodiment, the combination comprises or consists essentially of the peptide compound 1 and the peptide compound 10. In yet a further embodiment, the combination comprises or consists essentially of the peptide compound 10 and the peptide compound 18. In the combination of the present disclosure, the term "consists essentially of" refers to a feature of the combination, namely that it does not include additional peptide compounds but could include other therapeutic agents or non-medicinal ingredients.

Therapeutic Uses of the Peptide Compounds and Combinations

The peptide compounds and combinations described herein can be used for the treatment hypogonadism or conditions associated with hypoganadism. Hypogonadism is understood as diminished functional activity of the gonads (e.g., the testes and ovaries) resulting in diminished sex hormone (e.g., testosterone, estradiol, biosynthesis progesterone, DHEA, anti-Müllerian hormone, activin and inhibin). Hypogonadism can be primary (e.g., associated with a decreased androgen production by Leydig's cells), secondary (e.g., inadequate gonadotropin-releasing hormone or luteinizing hormone signaling) or tertiary (e.g. associated with both a decreased androgen production and an inadequate gonadotropin-releasing hormone or luteinizing hormone signaling). Hypogonadism can also be an acquired conditions caused by exposure to a stress or trauma (e.g., surgery, exposure to toxic chemicals such as explosives and chemotherapy, exposure to therapeutic drugs or biologicals, post-traumatic stress syndrome, etc.). Hypogonadism can be compensated by increased levels of the luteinizing hormone. Hypogonadism can be a late onset hypogonadism and be associated with both central and gonadal deficiency. In some embodiments, hypogonadism can be caused by a trauma. Low androgen (e.g., testosterone) levels can be referred to as hypoandrogenism and low estrogen (e.g., estradiol) can be referred to as hypoestrogenism. Conditions associated with hypogonadism include, but are not limited to infertility (due to defective or insufficient spermatogenesis or ovulation), aging, decreased libido, sexual dysfunction, altered mood, fatigue, decreased lean body mass, decreased bone mineral density, increased visceral fat, wasting (metabolic, associated with exposure to chemotherapy, associated with the presence of cancer, associated with the presence of an infection such as, for example, an HIV infection) and metabolic syndrome. In some embodiments, conditions associated with hypogonadism are those listed in the OMIM database and include, without limitation, genetic mutations or conditions associated with HYPOGONADISM WITH LOW-GRADE MENTAL DEFICIENCY AND MICROCEPHALY (OMIM: 241000), CEREBELLAR ATAXIA AND HYPERGONADOTROPIC HYPOGONADISM (OMIM: 605672), MUSCULAR DYSTROPHY, CONGENITAL, WITH INFANTILE CATARACT AND HYPOGONADISM (OMIM: 254000), HYPOGONADISM-CATARACT SYNDROME (OMIM: 240950), HYPOGONADISM, MALE, WITH MENTAL RETARDATION AND SKELETAL ANOMALIES (OMIM: 307500), HYPOGONADISM, MALE HYPOGONADISM AND TESTICULAR ATROPHY, INCLUDED (OMIM: 241100), RETINITIS PIGMENTOSA, DEAFNESS, MENTAL RETARDATION, AND HYPOGONADISM (OMIM: 268020), DEAFNESS-HYPOGONADISM SYNDROME (OMIM: 304350), MULTICORE MYOPATHY WITH MENTAL RETARDATION, SHORT STATURE, AND HYPOGONADOTROPIC HYPOGONADISM (OMIM: 253320), HYPERGONADOTROPIC HYPOGONADISM AND PARTIAL ALOPECIA (OMIM: 241090), ALOPECIA-MENTAL RETARDATION SYNDROME WITH CONVULSIONS AND HYPERGONADOTROPIC HYPOGONADISM (OMIM: 601217), JOHNSON NEUROECTODERMAL SYNDROME (OMIM: 147770), HYPOGONADOTROPIC HYPOGONADISM 9 WITH OR WITHOUT ANOSMIA; HH9 Cytogenetic locations: 9q34.3 (OMIM: 614838), HYPOGONADOTROPIC HYPOGONADISM 6 WITH OR WITHOUT ANOSMIA; HH6 Cytogenetic locations: 10q24.32 (OMIM: 612702), ICHTHYOSIS AND MALE HYPOGONADISM RUD SYNDROME, INCLUDED (OMIM: 308200), HYPOGONADOTROPIC HYPOGONADISM 5 WITH OR WITHOUT ANOSMIA; HH5 Cytogenetic locations: 8q12.2 (OMIM: 612370), HYPOGONADOTROPIC HYPOGONADISM 19 WITH OR WITHOUT ANOSMIA; HH19 Cytogenetic locations: 12q21.33 (OMIM: 615269), HYPOGONADOTROPIC HYPOGONADISM 17 WITH OR WITHOUT ANOSMIA; HH17 Cytogenetic locations: 5q31.3 (OMIM: 615266), HYPOGONADOTROPIC HYPOGONADISM 20 WITH OR WITHOUT ANOSMIA; HH20 Cytogenetic locations: 8p21.3 (OMIM: 615270), HYPOGONADOTROPIC HYPOGONADISM 4 WITH OR WITHOUT ANOSMIA; HH4 Cytogenetic locations: 3p13 (OMIM: 610628), HYPOGONADOTROPIC HYPOGONADISM 21 WITH OR WITHOUT ANOSMIA; HH21 Cytogenetic locations: 20p12.1 (OMIM: 615271), HYPOGONADOTROPIC HYPOGONADISM 10 WITH OR WITHOUT ANOSMIA; HH10 Cytogenetic locations: 12q13.3 (OMIM: 614839), CARDIOMYOPATHY, DILATED, WITH HYPERGONADOTROPIC HYPOGONADISM (OMIM: 212112), HYPOGONADOTROPIC HYPOGONADISM 11 WITH OR WITHOUT ANOSMIA; HH11 Cytogenetic locations: 4q24 (OMIM: 614840), HYPOGONADOTROPIC HYPOGONADISM 3 WITH OR WITHOUT ANOSMIA; HH3 Cytogenetic locations: 20p12.3 (OMIM: 244200), SCHOLTE SYNDROME; SHLTS (OMIM: 300977), HYPOGONADOTROPIC HYPOGONADISM 18 WITH OR WITHOUT ANOSMIA; HH18 Cytogenetic locations: 3p14.3 (OMIM: 615267), HYPOGONADOTROPIC HYPOGONADISM 13 WITH OR WITHOUT ANOSMIA; HH13 Cytogenetic locations: 1q32.1 (OMIM: 614842), HYPOGONADOTROPIC HYPOGONADISM 7 WITH OR WITHOUT ANOSMIA; HH7 Cytogenetic locations: 4q13.2 (OMIM: 146110), MOYAMOYA DISEASE 4 WITH SHORT STATURE, HYPERGONADOTROPIC HYPOGONADISM, AND FACIAL DYSMORPHISM; MYMY4 Cytogenetic locations: Xq28 (OMIM: 300845), LEUKODYSTROPHY, HYPOMYELINATING, 7, WITH OR WITHOUT OLIGODONTIA AND/OR HYPOGONADOTROPIC HYPOGONADISM; HLD7 Cytogenetic locations: 10q22.3 (OMIM: 607694), WOODHOUSE-SAKATI SYNDROME Cytogenetic locations: 2q31.1 (OMIM: 241080), HYPOGONADOTROPIC HYPOGONADISM 14 WITH OR WITHOUT ANOSMIA; HH14 Cytogenetic locations: 10q26.12 (OMIM: 614858), GORDON HOLMES SYNDROME; GDHS Cytogenetic locations: 7p22.1 (OMIM: 212840), LEUKODYSTROPHY, HYPOMYELINATING, 8, WITH OR WITHOUT OLIGODONTIA AND/OR HYPOGONADOTROPIC HYPOGONADISM; HLD8 Cytogenetic locations: 12q23.3 (OMIM: 614381), HYPOGONADOTROPIC HYPOGONADISM 12 WITH OR WITHOUT ANOSMIA; HH12 Cytogenetic locations: 8p21.2 (OMIM: 614841), MARTSOLF SYNDROME Cytogenetic locations: 1q41 (OMIM: 212720), BOUCHER-NEUHAUSER SYNDROME; BNHS Cytogenetic locations: 19p13.2 (OMIM: 215470), HYPOGONADOTROPIC HYPOGONADISM 15 WITH OR WITHOUT ANOSMIA; HH15 Cytogenetic locations: 2q14.3 (OMIM: 614880), HYPOGONADOTROPIC HYPOGONADISM 22 WITH OR WITHOUT ANOSMIA; HH22 Cytogenetic locations: 7q31.32 (OMIM: 616030), HYPOGONADOTROPIC HYPOGONADISM 1 WITH OR WITHOUT ANOSMIA; HH1 Cytogenetic locations: Xp22.31 (OMIM: 308700), HYPOGONADOTROPIC HYPOGONADISM 24 WITHOUT ANOSMIA; HH24 Cytogenetic locations: 11p14.1 (OMIM: 229070), BOSMA ARHINIA MICROPHTHALMIA SYNDROME; BAMS Cytogenetic locations: 18p11.32 (OMIM: 603457), LEYDIG CELL HYPOPLASIA, TYPE I and LEYDIG CELL HYPOPLASIA, TYPE II, INCLUDED Cytogenetic locations: 2p16.3 (OMIM: 238320), HYPOGONADOTROPIC HYPOGONADISM 16 WITH OR WITHOUT ANOSMIA; HH16 Cytogenetic locations: 7q21.11 (OMIM: 614897), MENTAL RETARDATION, X-LINKED, SYNDROMIC, CABEZAS TYPE; MRXSC Cytogenetic locations: Xq24 (OMIM: 300354), HYPOGONADOTROPIC HYPOGONADISM 23 WITHOUT ANOSMIA; HH23 Cytogenetic locations: 19q13.33 (OMIM: 228300), HYPOGONADOTROPIC HYPOGONADISM 8 WITH OR WITHOUT ANOSMIA; HH8 Cytogenetic locations: 19p13.3 (OMIM: 614837), ADRENAL HYPOPLASIA, CONGENITAL; AHC Cytogenetic locations: Xp21.2 (OMIM: 300200), PITUITARY HORMONE DEFICIENCY, COMBINED, 2; CPHD2 Cytogenetic locations: 5q35.3 (OMIM: 262600), HYPOGONADOTROPIC HYPOGONADISM 2 WITH OR WITHOUT ANOSMIA; HH2 Cytogenetic locations: 8p11.23 (OMIM: 147950), Na+/K+ TRANSPORTING ATPase-INTERACTING 2; NKAIN2 TCBA1/SUSP1 FUSION GENE, INCLUDED Cytogenetic locations: 6q22.31 (OMIM: 609758), MEHMO SYNDROME; MEHMO Cytogenetic locations: 1 pter-p36.13, Xp22.11 (OMIM: 300148), HISTIOCYTOSIS-LYMPHADENOPATHY PLUS SYNDROME Cytogenetic locations: 1 pter-p36.13, 10q22.1 (OMIM: 602782), WAARDENBURG SYNDROME, TYPE 2E; WS2E Cytogenetic locations: 22q13.1 (OMIM: 611584), BRACHYTELEPHALANGY WITH CHARACTERISTIC FACIES AND KALLMANN SYNDROME (OMIM: 113480), TESTES, RUDIMENTARY (OMIM: 273150), MENTAL RETARDATION SYNDROME, BELGIAN TYPE (OMIM: 249599), SPASTIC PARAPARESIS AND DEAFNESS (OMIM: 312910), TACHYKININ RECEPTOR 3; TACR3 Cytogenetic locations: 4q24 (OMIM: 162332), NMDA RECEPTOR SYNAPTONUCLEAR SIGNALING AND NEURONAL MIGRATION FACTOR; NSMF Cytogenetic locations: 9q34.3 (OMIM: 608137), TACHYKININ 3; TAC3 Cytogenetic locations: 12q13.3 (OMIM: 162330), POLYMERASE III, RNA, SUBUNIT B; POLR3B Cytogenetic locations: 12q23.3 (OMIM: 614366), KISS1 RECEPTOR; KISS1R Cytogenetic locations: 19p13.3 (OMIM: 604161), POLYMERASE III, RNA, SUBUNIT A; POLR3A Cytogenetic locations: 10q22.3 (OMIM: 614258), SPROUTY, DROSOPHILA, HOMOLOG OF, 4; SPRY4 Cytogenetic locations: 5q31.3 (OMIM: 607984), WD REPEAT-CONTAINING PROTEIN 11; WDR11 Cytogenetic locations: 10q26.12 (OMIM: 606417), INTERLEUKIN 17 RECEPTOR D; IL17RD Cytogenetic locations: 3p14.3 (OMIM: 606807), FIBRONECTIN-LIKE DOMAIN-CONTAINING LEUCINE-RICH TRANSMEMBRANE PROTEIN 3; FLRT3 Cytogenetic locations: 20p12.1 (OMIM: 604808), GONADOTROPIN-RELEASING HORMONE RECEPTOR; GNRHR Cytogenetic locations: 4a13.2 (OMIM: 138850), PROKINETICIN 2; PROK2 Cytogenetic locations: 3p13 (OMIM: 607002), DUAL-SPECIFICITY PHOSPHATASE 6; DUSP6 Cytogenetic locations: 12q21.33 (OMIM: 602748), CONE-ROD DYSTROPHY 1; CORD1 Cytogenetic locations: 18q21.1-q21.3 (OMIM: 600624), FIBROBLAST GROWTH FACTOR 17; FGF17 Cytogenetic locations: 8p21.3 (OMIM: 603725), FEZ FAMILY ZINC FINGER PROTEIN 1; FEZF1 Cytogenetic locations: 7q31.32 (OMIM: 613301), HEPARAN SULFATE 6-O-SULFOTRANSFERASE 1; HS6ST1 Cytogenetic locations: 2q14.3 (OMIM: 604846), KAL1 GENE; KAL1 Cytogenetic locations: Xp22.31 (OMIM: 300836), DEAFNESS, CONDUCTIVE, WITH MALFORMED EXTERNAL EAR (OMIM: 221300), FOLLICLE-STIMULATING HORMONE, BETA POLYPEPTIDE; FSHB Cytogenetic locations: 11p14.1 (OMIM: 136530), HEMOCHROMATOSIS, TYPE 2B; HFE2B Cytogenetic locations: 19q13.12 (OMIM: 613313), FIBROBLAST GROWTH FACTOR RECEPTOR 1; FGFR1 FGFR1/BCR FUSION GENE, INCLUDED Cytogenetic locations: 8p11.23 (OMIM: 136350), LUTEINIZING HOR- MONE, BETA POLYPEPTIDE; LHB Cytogenetic locations: 19q13.33 (OMIM: 152780), PROKINETICIN RECEPTOR 2; PROKR2 Cytogenetic locations: 20p12.3 (OMIM: 607123), KISS1 METASTASIS SUPPRESSOR; KISS1 Cytogenetic locations: 1q32.1 (OMIM: 603286), GONADOTROPIN-RELEASING HORMONE 1; GNRH1 PROLACTIN RELEASE-INHIBITING FACTOR, INCLUDED; PIF, INCLUDED Cytogenetic locations: 8p21.2 (OMIM: 152760), COLOBOMA-OBESITY-HYPOGENITALISM-MENTAL RETARDATION SYNDROME (OMIM: 601794), BARDET-BIEDL SYNDROME 19; BBS19 Cytogenetic locations: 22q12.3 (OMIM: 615996), CHROMODOMAIN HELICASE DNA-BINDING PROTEIN 7; CHD7 Cytogenetic locations: 8q12.2 (OMIM: 608892), KALLMANN SYNDROME WITH SPASTIC PARAPLEGIA (OMIM: 308750), LUTEINIZING HORMONE/CHORIOGONADOTROPIN RECEPTOR; LHCGR Cytogenetic locations: 2p16.3 (OMIM: 152790), SEMAPHORIN 3A; SEMA3A Cytogenetic locations: 7q21.11 (OMIM: 603961), WILSON-TURNER X-LINKED MENTAL RETARDATION SYNDROME; WTS Cytogenetic locations: Xq12 (OMIM: 309585), FIBROBLAST GROWTH FACTOR 8; FGF8 Cytogenetic locations: 10q24.32 (OMIM: 600483), BARDET-BIEDL SYNDROME 11; BBS11 Cytogenetic locations: 9q33.1 (OMIM: 615988), BARDET-BIEDL SYNDROME 20; BBS20 Cytogenetic locations: 9p21.2 (OMIM: 617119), MICROCEPHALY WITH CHEMOTACTIC DEFECT AND TRANSIENT HYPOGAMMAGLOBULINEMIA (OMIM: 251240), RICHARDS-RUNDLE SYNDROME; RRNS (OMIM: 245100), TETRAMELIC DEFICIENCIES, ECTODERMAL DYSPLASIA, DEFORMED EARS, AND OTHER ABNORMALITIES (OMIM: 273400), HEMOCHROMATOSIS, TYPE 2A; HFE2A HEMOCHROMATOSIS, TYPE 2, INCLUDED; HFE2, INCLUDED Cytogenetic locations: 1q21.1 (OMIM: 602390), MANDIBULAR HYPOPLASIA, DEAFNESS, PROGEROID FEATURES, AND LIPODYSTROPHY SYNDROME; MDPL Cytogenetic locations: 19q13.33 (OMIM: 615381), SPINOCEREBELLAR ATAXIA, AUTOSOMAL RECESSIVE 16; SCAR16 Cytogenetic locations: 16p13.3 (OMIM: 615768), PROGRESSIVE EXTERNAL OPHTHALMOPLEGIA WITH MITOCHONDRIAL DNA DELETIONS, AUTOSOMAL DOMINANT 1; PEOA1 Cytogenetic locations: 15q26.1 (OMIM: 157640), LEUKOENCEPHALOPATHY WITH DYSTONIA AND MOTOR NEUROPATHY; LKDMN Cytogenetic locations: 1p32.3 (OMIM: 613724), BARDET-BIEDL SYNDROME 8; BBS8 Cytogenetic locations: 14q31.3 (OMIM: 615985), BJORNSTAD SYNDROME; BJS Cytogenetic locations: 2q35 (OMIM: 262000), MARINESCO-SJOGREN SYNDROME; MSS Cytogenetic locations: 5q31.2 (OMIM: 248800), ANDROGEN INSENSITIVITY, PARTIAL; PAIS Cytogenetic locations: Xq12 (OMIM: 312300), ICHTHYOSIS, X-LINKED; XLI ICHTHYOSIS, X-LINKED, COMPLICATED, INCLUDED Cytogenetic locations: Xp22.31 (OMIM: 308100), BARDET-BIEDL SYNDROME 5; BBS5 Cytogenetic locations: 2q31.1 (OMIM: 615983), ACROMESOMELIC DYSPLASIA, DEMIRHAN TYPE; AMDD Cytogenetic locations: 4q22.3 (OMIM: 609441), NEPHROTIC SYNDROME 14; NPHS14 Cytogenetic locations: 10q22.1 (OMIM: 617575), MENTAL RETARDATION-HYPOTONIC FACIES SYNDROME, X-LINKED, 1; MRXHF1 Cytogenetic locations: Xq21.1 (OMIM: 309580), CORNELIA DE LANGE SYNDROME 5; CDLS5 Cytogenetic locations: Xq13.1 (OMIM: 300882), 114. #612079-ALOPECIA, NEUROLOGIC DEFECTS, AND ENDOCRINOPATHY SYNDROME; ANES Cytogenetic locations: 7q32.1 (OMIM: 612079), RING FINGER PROTEIN 216; RNF216 Cytogenetic locations: 7p22.1 (OMIM: 609948), LEPTIN DEFICIENCY OR DYSFUNCTION; LEPD Cytogenetic locations: 7q32.1 (OMIM: 614962), BARDET-BIEDL SYNDROME 17; BBS17 Cytogenetic locations: 3p21.31 (OMIM: 615994), OLIVER-MCFARLANE SYNDROME; OMCS Cytogenetic locations: 19p13.2 (OMIM: 275400), MOEBIUS SYNDROME; MBS Cytogenetic locations: 13q12.2-q13 (OMIM: 157900), BARDET-BIEDL SYNDROME 12; BBS12 Cytogenetic locations: 4q27 (OMIM: 615989), MICROPHTHALMIA, SYNDROMIC 3; MCOPS3 OPTIC NERVE HYPOPLASIA AND ABNORMALITIES OF THE CENTRAL NERVOUS SYSTEM, INCLUDED Cytogenetic locations: 3q26.33 (OMIM: 206900), CHROMOSOME Xq27.3-q28 DUPLICATION SYNDROME Cytogenetic locations: Xq27.3-q28 (OMIM: 300869), ALSTROM SYNDROME; ALMS Cytogenetic locations: 2p13.1 (OMIM: 203800), GALACTOSEMIA GALACTOSEMIA, DUARTE VARIANT, INCLUDED Cytogenetic locations: 9p13.3 (OMIM: 230400), COMBINED OXIDATIVE PHOSPHORYLATION DEFICIENCY 34; COXPD34 Cytogenetic locations: 17q25.1 (OMIM: 617872), BARDET-BIEDL SYNDROME 1; BBS1 Cytogenetic locations: 1p35.2, 1 pter-p36.13, 3q11.2 (OMIM: 209900), CONGENITAL CATARACTS, FACIAL DYSMORPHISM, AND NEUROPATHY; CCFDN Cytogenetic locations: 18q23 (OMIM: 604168), ANEMIA, HYPOCHROMIC MICROCYTIC, WITH IRON OVERLOAD 2; AHMIO2 Cytogenetic locations: 2q14.2 (OMIM: 615234), PRADER-WILLI SYNDROME; PWS PRADER-WILLI SYNDROME CHROMOSOME REGION, INCLUDED; PWCR, INCLUDED Cytogenetic locations: 1 pter-p36.13, 15q11.2 (OMIM: 176270), HEMOCHROMATOSIS, TYPE 1; HFE1 Cytogenetic locations: 1 pter-p36.13, 20p12.3 (OMIM: 235200), SENIOR-LOKEN SYNDROME 9; SLSN9 Cytogenetic locations: 2q37.3 (OMIM: 616629), MITOCHONDRIAL DNA DEPLETION SYNDROME 11; MTDPS11 Cytogenetic locations: 20p11.23 (OMIM: 615084), ALPHA-METHYLACYL-CoA RACEMASE DEFICIENCY; AMACRD Cytogenetic locations: 5p13.2 (OMIM: 614307), SIFRIM-HITZ-WEISS SYNDROME; SIHIWES Cytogenetic locations: 12p13.31 (OMIM: 617159), CONGENITAL DISORDER OF GLYCOSYLATION, TYPE Ik; CDG1K Cytogenetic locations: 16p13.3 (OMIM: 608540), CONGENITAL DISORDER OF GLYCOSYLATION, TYPE It; CDG1T Cytogenetic locations: 1p31.3 (OMIM: 614921), POLYENDOCRINE-POLYNEUROPATHY SYNDROME; PEPNS Cytogenetic locations: 15q21.2 (OMIM: 616113), PROPROTEIN CONVERTASE 1/3 DEFICIENCY Cytogenetic locations: 5q15 (OMIM: 600955), BARDET-BIEDL SYNDROME 2; BBS2 Cytogenetic locations: 16q13 (OMIM: 615981), MACS SYNDROME Cytogenetic locations: 20p11.23 (OMIM: 613075), MITOCHONDRIAL DNA DEPLETION SYNDROME 7 (HEPATOCEREBRAL TYPE); MTDPS7 Cytogenetic locations: 10q24.31 (OMIM: 271245), MICROCEPHALY, EPILEPSY, AND DIABETES SYNDROME; MEDS Cytogenetic locations: 18q21.1 (OMIM: 614231), CULLER-JONES SYNDROME; CJS Cytogenetic locations: 2q14.2 (OMIM: 615849), SCHAAF-YANG SYNDROME; SHFYNG Cytogenetic locations: 15q11.2 (OMIM: 615547), HYPOTONIA-CYSTINURIA SYNDROME HOMOZYGOUS 2p21 DELETION SYNDROME, INCLUDED Cytogenetic locations: 2p21 (OMIM: 606407), AUTOIMMUNE POLYENDOCRINE SYNDROME, TYPE I, WITH OR WITHOUT REVERSIBLE METAPHYSEAL DYSPLASIA; APS1 AUTOIMMUNE POLYENDOCRINOPATHY SYNDROME, TYPE I, AUTOSOMAL DOMINANT, INCLUDED Cytogenetic locations: 21q22.3 (OMIM: 240300), ROTHMUND-THOMSON SYNDROME; RTS Cytogenetic locations: 8q24.3 (OMIM: 268400), PRIMROSE SYNDROME; PRIMS Cytogenetic locations: 3q13.31 (OMIM: 259050), CHROMOSOME 2p16.1-p15 DELETION SYNDROME Cytogenetic locations: 2p16.1-p15 (OMIM: 612513), WITTEVEEN-KOLK SYNDROME; WITKOS CHROMOSOME 15q24 DELETION SYNDROME, INCLUDED Cytogenetic locations: 15q24.2 (OMIM: 613406), MYOTONIC DYSTROPHY 2; DM2 Cytogenetic locations: 3q21.3 (OMIM: 602668), FANCONI ANEMIA, COMPLEMENTATION GROUP A; FANCA FANCONI ANEMIA, ESTREN-DAMESHEK VARIANT, INCLUDED Cytogenetic locations: 16q24.3 (OMIM: 227650), CONGENITAL DISORDER OF GLYCOSYLATION, TYPE Ia; CDG1A Cytogenetic locations: 16p13.2 (OMIM: 212065), MYOTONIC DYSTROPHY 1; DM1 Cytogenetic locations: 19q13.32 (OMIM: 160900), DEAFNESS, CONGENITAL, WITH TOTAL ALBINISM (OMIM: 220900), HEMOCHROMATOSIS, TYPE 3; HFE3 Cytogenetic locations: 7q22.1 (OMIM: 604250), CAMURATI-ENGELMANN DISEASE, TYPE 2 (OMIM: 606631), BARDET-BIEDL SYNDROME 10; BBS10 Cytogenetic locations: 12q21.2 (OMIM: 615987), BARDET-BIEDL SYNDROME 16; BBS16 Cytogenetic locations: 1q43-q44 (OMIM: 615993), PERRAULT SYNDROME 5; PRLTS5 Cytogenetic locations: 10q24.31 (OMIM: 616138), FANCONI ANEMIA, COMPLEMENTATION GROUP E; FANCE Cytogenetic locations: 6p21.31 (OMIM: 600901), BARDET-BIEDL SYNDROME 4; BBS4 Cytogenetic locations: 15q24.1 (OMIM: 615982), WAARDENBURG SYNDROME, TYPE 4C; WS4C Cytogenetic locations: 22q13.1 (OMIM: 613266), PSEUDOHYPOPARATHYROIDISM, TYPE IC; PHP1C Cytogenetic locations: 20q13.32 (OMIM: 612462), XERODERMA PIGMENTOSUM, COMPLEMENTATION GROUP B; XPB XERODERMA PIGMENTOSUM B/COCKAYNE SYNDROME, INCLUDED Cytogenetic locations: 2q14.3 (OMIM: 610651), FANCONI ANEMIA, COMPLEMENTATION GROUP D2; FANCD2 Cytogenetic locations: 3p25.3 (OMIM: 227646), MIRAGE SYNDROME; MIRAGE Cytogenetic locations: 7q21.2 (OMIM: 617053), FANCONI ANEMIA, COMPLEMENTATION GROUP C; FANCC Cytogenetic locations: 9q22.32 (OMIM: 227645), ACRODYSOSTOSIS 1 WITH OR WITHOUT HORMONE RESISTANCE; ACRDYS1 Cytogenetic locations: 17q24.2 (OMIM: 101800), ECTRODACTYLY, ECTODERMAL DYSPLASIA, AND CLEFT LIP/PALATE SYNDROME 1; EEC1 Cytogenetic locations: 7q11.2-q21.3 (OMIM: 129900), ECTRODACTYLY, ECTODERMAL DYSPLASIA, AND CLEFT LIP/PALATE SYNDROME 3; EEC3 Cytogenetic locations: 3q28 (OMIM: 604292), CHONDRODYSPLASIA PUNCTATA 1, X-LINKED RECESSIVE; CDPX1 Cytogenetic locations: Xp22.33 (OMIM: 302950), PROGRESSIVE EXTERNAL OPHTHALMOPLEGIA WITH MITOCHONDRIAL DNA DELETIONS, AUTOSOMAL DOMINANT 3; PEOA3 Cytogenetic locations: 10q24.31 (OMIM: 609286), COCKAYNE SYNDROME A; CSA Cytogenetic locations: 5q12.1 (OMIM: 216400), WERNER SYNDROME; WRN Cytogenetic locations: 8p12 (OMIM: 277700), PSEUDOHYPOPARATHYROIDISM, TYPE IA; PHP1A Cytogenetic locations: 20q13.32 (OMIM: 103580), ATAXIA-TELANGIECTASIA; AT AT, COMPLEMENTATION GROUP A, INCLUDED; ATA, INCLUDED Cytogenetic locations: 11q22.3 (OMIM: 208900), NOONAN SYNDROME 1; NS1 PTERYGIUM COLLI SYNDROME, INCLUDED Cytogenetic locations: 12q24.13 (OMIM: 163950), OTU DOMAIN-CONTAINING PROTEIN 4; OTUD4 Cytogenetic locations: 4q31.21 (OMIM: 611744), DDB1- AND CUL4-ASSOCIATED FACTOR 17; DCAF17 Cytogenetic locations: 2q31.1 (OMIM: 612515), NUCLEAR RECEPTOR SUBFAMILY 0, GROUP B, MEMBER 1; NR0B1 Cytogenetic locations: Xp21.2 (OMIM: 300473), CULLIN 4B; CUL4B Cytogenetic locations: Xq24 (OMIM: 300304), PATATIN-LIKE PHOSPHOLIPASE DOMAIN-CONTAINING PROTEIN 6; PNPLA6 Cytogenetic locations: 19p13.2 (OMIM: 603197), SRY-BOX 2; SOX2 Cytogenetic locations: 3q26.33 (OMIM: 184429), PROP PAIRED-LIKE HOMEOBOX 1; PROP1 Cytogenetic locations: 5q35.3 (OMIM: 601538), SEMAPHORIN 3E; SEMA3E Cytogenetic locations: 7q21.11 (OMIM: 608166), OVARIAN DYSGENESIS, HYPERGONADOTROPIC, WITH SHORT STATURE AND RECURRENT METABOLIC ACIDOSIS (OMIM: 605756), DMX-LIKE 2; DMXL2 Cytogenetic locations: 15q21.2 (OMIM: 612186), X-RAY REPAIR, COMPLEMENTING DEFECTIVE, IN CHINESE HAMSTER, 4; XRCC4 Cytogenetic locations: 5q14.2 (OMIM: 194363), SOLUTE CARRIER FAMILY 29 (NUCLEOSIDE TRANSPORTER), MEMBER 3: SLC29A3 Cytogenetic locations: 10q22.1 (OMIM: 612373), LAMIN A/C; LMNA LAMIN A, INCLUDED Cytogenetic locations: 1q22 (OMIM: 150330), CRANIOSYNOSTOSIS-MENTAL RETARDATION SYNDROME OF LIN AND GETTIG (OMIM: 218649), ANOSMIA, ISOLATED CONGENITAL; ANIC Cytogenetic locations: 18p11.23-q12.2 (OMIM: 107200), BIEMOND SYNDROME II (OMIM: 210350), HYPERZINCEMIA WITH FUNCTIONAL ZINC DEPLETION (OMIM: 601979), CHROMOSOME Xp21 DELETION SYNDROME Cytogenetic locations: Xp21 (OMIM: 300679), COILED-COIL DOMAIN-CONTAINING PROTEIN 141; CCDC141 Cytogenetic locations: 2q31.2 (OMIM: 616031), LAURENCE-MOON SYNDROME; LNMS Cytogenetic locations: 19p13.2 (OMIM: 245800), OVARIAN DYSGENESIS 5; ODG5 Cytogenetic locations: 9q34.3 (OMIM: 617690), LEUKODYSTROPHY, HYPOMYELINATING, 11; HLD11 Cytogenetic locations: 6p21.1 (OMIM: 616494), SMALL NUCLEOLAR RNA, C/D BOX, 116-1; SNORD116-1 Cytogenetic locations: 15q11.2 (OMIM: 605436), MENTAL RETARDATION, X-LINKED, SYNDROMIC 7; MRXS7 Cytogenetic locations: Xp11.3-q22 (OMIM: 300218), PINEAL HYPERPLASIA, INSULIN-RESISTANT DIABETES MELLITUS, AND SOMATIC ABNORMALITIES Cytogenetic locations: 19p13.2 (OMIM: 262190), CHARGE SYNDROME Cytogenetic locations: 1 pter-p36.13, 7q21.11 (OMIM: 214800), ROIFMAN SYNDROME; RFMN Cytogenetic locations: 2q14.2 (OMIM: 616651 POLO-LIKE KINASE 4; PLK4 Cytogenetic locations: 4q28.1 (OMIM: 605031), AROMATASE EXCESS SYNDROME; AEXS GYNECOMASTIA, FAMILIAL, DUE TO INCREASED AROMATASE ACTIVITY, INCLUDED Cytogenetic locations: 15q21.2 (OMIM: 139300), BORJESON-FORSSMAN-LEHMANN SYNDROME; BFLS Cytogenetic locations: Xq26.2 (OMIM: 301900), HISTONE DEACETYLASE 8; HDAC8 Cytogenetic locations: Xq13.1 (OMIM: 300269), ROBINOW SYNDROME, AUTOSOMAL DOMINANT 1; DRS1 Cytogenetic locations: 3p14.3 (OMIM: 180700), STIP1 HOMOLOGOUS AND U BOX-CONTAINING PROTEIN 1; STUB1 Cytogenetic locations: 16p13.3

(OMIM: 607207), MICROCEPHALY 1, PRIMARY, AUTOSOMAL RECESSIVE; MCPH1 Cytogenetic locations: 8p23.1 (OMIM: 251200), AROMATASE DEFICIENCY Cytogenetic locations: 15q21.2 (OMIM: 613546), METAPHYSEAL UNDERMODELING, SPONDYLAR DYSPLASIA, AND OVERGROWTH (OMIM: 608811), COENZYME Q10 DEFICIENCY, PRIMARY, 1; COQ10D1 Cytogenetic locations: 4q21.22-q21.23 (OMIM: 607426), RETINOPATHY, PIGMENTARY, AND MENTAL RETARDATION (OMIM: 268050), STRUCTURAL MAINTENANCE OF CHROMOSOMES FLEXIBLE HINGE DOMAIN-CONTAINING PROTEIN 1; SMCHD1 Cytogenetic locations: 18p11.32 (OMIM: 614982), CYTOCHROME P450, FAMILY 19, SUBFAMILY A, POLYPEPTIDE 1; CYP19A1 CYP19A1/CGNL1 FUSION GENE, INCLUDED Cytogenetic locations: 15q21.2 (OMIM: 107910), N-MYRISTOYLTRANSFERASE 2; NMT2 Cytogenetic locations: 10p13 (OMIM: 603801), POLYMERASE, DNA, GAMMA; POLG Cytogenetic locations: 15q26.1 (OMIM: 174763), LEPTIN; LEP Cytogenetic locations: 7q32.1 (OMIM: 164160), CINGULIN-LIKE 1; CGNL1 CGNL1/CYP19A1 FUSION GENE, INCLUDED Cytogenetic locations: 15q21.3 (OMIM: 607856), BKM DNA BKMA2, INCLUDED Cytogenetic locations: 6q21 (OMIM: 109780), LEPTIN RECEPTOR DEFICIENCY Cytogenetic locations: 1p31.3 (OMIM: 614963), BARDET-BIEDL SYNDROME 7; BBS7 Cytogenetic locations: 4q27 (OMIM: 615984), TORTICOLLIS, KELOIDS, CRYPTORCHIDISM, AND RENAL DYSPLASIA; TKCR Cytogenetic locations: Xq28 (OMIM: 314300), TAX1-BINDING PROTEIN 3; TAX1BP3 Cytogenetic locations: 17p13.2 (OMIM: 616484), IMMUNOGLOBULIN SUPERFAMILY, MEMBER 10; IGSF10 Cytogenetic locations: 3q25.1 (OMIM: 617351), SHORT STATURE, MICROCEPHALY, AND ENDOCRINE DYSFUNCTION; SSMED Cytogenetic locations: 5q14.2 (OMIM: 616541), PERRAULT SYNDROME 3; PRLTS3 Cytogenetic locations: 19p13.3 (OMIM: 614129), HYPERPROLACTINEMIA; HPRL Cytogenetic locations: 5p13.2 (OMIM: 615555), CHROMOSOME 17q21.31 DUPLICATION SYNDROME Cytogenetic locations: 17q21.31 (OMIM: 613533), PREMATURE OVARIAN FAILURE 10; POF10 MENOPAUSE, NATURAL, AGE AT, QUANTITATIVE TRAIT LOCUS 3, INCLUDED; MENOQ3, INCLUDED Cytogenetic locations: 20p12.3 (OMIM: 612885), BRCA1/BRCA2-CONTAINING COMPLEX, SUBUNIT 3; BRCC3 Cytogenetic locations: Xq28 (OMIM: 300617), LARGE TUMOR SUPPRESSOR, DROSOPHILA, HOMOLOG OF, 1; LATS1 Cytogenetic locations: 6q25.1 (OMIM: 603473), WARBURG MICRO SYNDROME 4; WARBM4 Cytogenetic locations: 20p13 (OMIM: 615663), MATURE T-CELL PROLIFERATION 1; MTCP1 Cytogenetic locations: Xq28 (OMIM: 300116), 46,XX SEX REVERSAL 1; SRXX1 46,XX TRUE HERMAPHRODITISM, SRY-POSITIVE, INCLUDED Cytogenetic locations: Yp11.2 (OMIM: 400045), CRYPTORCHIDISM, UNILATERAL OR BILATERAL Cytogenetic locations: 19p13.11 (OMIM: 219050), DOUBLESEX- AND MAB3-RELATED TRANSCRIPTION FACTOR 2; DMRT2 Cytogenetic locations: 9p24.3 (OMIM: 604935), ZINC FINGER PROTEIN, X-LINKED; ZFX Cytogenetic locations: Xp22.11 (OMIM: 314980), TRICHOTHIODYSTROPHY 4, NONPHOTOSENSITIVE; TTD4 Cytogenetic locations: 7p14.1 (OMIM: 234050), TEASHIRT ZINC FINGER HOMEOBOX 1; TSHZ1 Cytogenetic locations: 18q22.3 (OMIM: 614427), LIMB-MAMMARY SYNDROME; LMS Cytogenetic locations: 3q28 (OMIM: 603543), OVARIAN DYSGENESIS 4; ODG4 Cytogenetic locations: 6q22.31 (OMIM: 616185), TRANSFERRIN RECEPTOR 2; TFR2 Cytogenetic locations: 7q22.1 (OMIM: 604720), 247. EPILEPTIC ENCEPHALOPATHY, EARLY INFANTILE, 28; EIEE28 Cytogenetic locations: 16q23.1-q23.2 (OMIM: 616211), WARBURG MICRO SYNDROME 3; WARBM3 Cytogenetic locations: 10p12.1 (OMIM: 614222), HARTSFIELD SYNDROME; HRTFDS Cytogenetic locations: 8p11.23 (OMIM: 615465), 250. %252350-MOYAMOYA DISEASE 1; MYMY1 Cytogenetic locations: 3p26-p24.2 (OMIM: 252350), HEMOJUVELIN; HJV Cytogenetic locations: 1q21.1 (OMIM: 608374), FANCONI ANEMIA, COMPLEMENTATION GROUP B; FANCB Cytogenetic locations: Xp22.2 (OMIM: 300514), INTRAUTERINE GROWTH RETARDATION, METAPHYSEAL DYSPLASIA, ADRENAL HYPOPLASIA CONGENITA, AND GENITAL ANOMALIES Cytogenetic locations: 11p15.4 (OMIM: 614732), RAB3 GTPase-ACTIVATING PROTEIN, NON-CATALYTIC SUBUNIT; RAB3GAP2 Cytogenetic locations: 1q41 (OMIM: 609275), CARPENTER SYNDROME 1; CRPT1 Cytogenetic locations: 6p12.1-p11.2 (OMIM: 201000), PHOSPHOGLYCERATE DEHYDROGENASE DEFICIENCY; PHGDHD Cytogenetic locations: 1p12 (OMIM: 601815), CASEINOLYTIC MITOCHONDRIAL MATRIX PEPTIDASE PROTEOLYTIC SUBUNIT; CLPP Cytogenetic locations: 19p13.3 (OMIM: 601119), 46,XY SEX REVERSAL 4; SRXY4 Cytogenetic locations: 9p24.3 (OMIM: 154230), LEUCINE ZIPPER TRANSCRIPTION FACTOR-LIKE 1; LZTFL1 Cytogenetic locations: 3p21.31 (OMIM: 606568), PONTOCEREBELLAR HYPOPLASIA, TYPE 7; PCH7 Cytogenetic locations: 1p34.1 (OMIM: 614969), SPERMATOGENIC FAILURE 1; SPGF1 (OMIM: 258150), SIL1, S. CEREVISIAE, HOMOLOG OF; SIL1 Cytogenetic locations: 5q31.2 (OMIM: 608005), 3MC SYNDROME 1; 3MC1 Cytogenetic locations: 3q27.3 (OMIM: 257920), LIPEDEMA (OMIM: 614103), INHIBIN, BETA B; INHBB ACTIVIN BETA-B, INCLUDED Cytogenetic locations: 2q14.2 (OMIM: 147390), DNA METHYLTRANSFERASE 3-LIKE PROTEIN; DNMT3L Cytogenetic locations: 21q22.3 (OMIM: 606588), NECDIN; NDN Cytogenetic locations: 15q11.2 (OMIM: 602117), HYPOPARATHYROIDISM-RETARDATION-DYSMORPHISM SYNDROME; HRDS Cytogenetic locations: 1q42.3 (OMIM: 241410), OPTIC ATROPHY WITH OR WITHOUT DEAFNESS, OPHTHALMOPLEGIA, MYOPATHY, ATAXIA, AND NEUROPATHY Cytogenetic locations: 3q29 (OMIM: 125250), 46,XX SEX REVERSAL 4; SRXX4 Cytogenetic locations: 9q33.3 (OMIM: 617480), MULIBREY NANISM Cytogenetic locations: 17q22 (OMIM: 253250), MICROPHTHALMIA, SYNDROMIC 6; MCOPS6 Cytogenetic locations: 14q22.2 (OMIM: 607932), PHD FINGER PROTEIN 6; PHF6 Cytogenetic locations: Xq26.2 (OMIM: 300414), PROPROTEIN CONVERTASE, SUBTILISIN/KEXIN-TYPE, 1; PCSK1 Cytogenetic locations: 5q15 (OMIM: 162150), SPHEROCYTOSIS, TYPE 1; SPH1 Cytogenetic locations: 8p11.21 (OMIM: 182900), GAPO SYNDROME Cytogenetic locations: 2p13.3 (OMIM: 230740), INHIBIN, BETA A; INHBA ACTIVIN A, INCLUDED Cytogenetic locations: 7p14.1 (OMIM: 147290), SRY-BOX 10; SOX10 Cytogenetic locations: 22q13.1 (OMIM: 602229), PROGRESSIVE EXTERNAL OPHTHALMOPLEGIA WITH MITOCHONDRIAL DNA DELETIONS, AUTOSOMAL RECESSIVE 1; PEOB1 Cytogenetic locations: 15q26.1 (OMIM: 258450), LIPASE, HORMONE-SENSITIVE; LIPE Cytogenetic locations: 19q13.2 (OMIM: 151750), MINICHROMOSOME MAIN- TENANCE COMPLEX COMPONENT 8; MCM8 Cytogenetic locations: 20p12.3 (OMIM: 608187), FANCM GENE; FANCM Cytogenetic locations: 14q21.2 (OMIM: 609644), MULTIPLE PTERYGIUM SYNDROME, ESCOBAR VARIANT; EVMPS Cytogenetic locations: 2q37.1 (OMIM: 265000), WARBURG MICRO SYNDROME 1; WARBM1 Cytogenetic locations: 2q21.3 (OMIM: 600118), TRICHO-RHINOPHALANGEAL SYNDROME, TYPE I; TRPS1 Cytogenetic locations: 8q23.3 (OMIM: 190350), MICRO-CEPHALIC OSTEODYSPLASTIC PRIMORDIAL DWARFISM, TYPE I; MOPD1 Cytogenetic locations: 2q14.2 (OMIM: 210710), FOLLICLE-STIMULATING HORMONE RECEPTOR; FSHR Cytogenetic locations: 2p16.3 (OMIM: 136435), MAGE-LIKE 2; MAGEL2 Cytogenetic locations: 15q11.2 (OMIM: 605283), NORRIE DISEASE; ND Cytogenetic locations: Xp11.3 (OMIM: 310600), LIGASE IV, DNA, ATP-DEPENDENT; LIG4 Cytogenetic locations: 13q33.3 (OMIM: 601837), SUPEROXIDE DISMUTASE 2; SOD2 Cytogenetic locations: 6q25.3 (OMIM: 147460), HUTCHINSON-GILFORD PROGERIA SYNDROME; HGPS PROGERIA SYNDROME, CHILDHOOD-ONSET, INCLUDED (OMIM: 176670), PITUITARY HORMONE DEFICIENCY, COMBINED, 1; CPHD1 Cytogenetic locations: 3p11.2 (OMIM: 613038), ALMS1 GENE; ALMS1 Cytogenetic locations: 2p13.1 (OMIM: 606844), TRICHOTHIODYSTROPHY 1, PHOTOSENSITIVE; TTD1 Cytogenetic locations: 19q13.32 (OMIM: 601675), OBESITY LEANNESS, INCLUDED Cytogenetic locations: 5q13.2, 1 pter-p36.13, 4q31.1, 1 pter-p36.13, 3p25.2, 1 pter-p36.13, 3p25.3, 1 pter-p36.13, 1p36.11, 1 pter-p36.13, 2p23.3, 1 pter-p36.13, 18q21.32, 1 pter-p36.13, 16q22.1 (OMIM: 601665), LINEAR SKIN DEFECTS WITH MULTIPLE CONGENITAL ANOMALIES 1; LSDMCA1 Cytogenetic locations: Xp22.2 (OMIM: 309801), GALANIN; GAL Cytogenetic locations: 11q13.2 (OMIM: 137035), JACOBSEN SYNDROME; JBS Cytogenetic locations: 11q23 (OMIM: 147791), WW DOMAIN-CONTAINING OXIDOREDUCTASE; WWOX FRAGILE SITE 16q23.2, INCLUDED; FRA16D, INCLUDED Cytogenetic locations: 16q23.1-q23.2 (OMIM: 605131), FANCG GENE; FANCG Cytogenetic locations: 9p13.3 (OMIM: 602956), STEROID SULFATASE; STS STEROID SULFATASE, ISOZYME S, INCLUDED Cytogenetic locations: Xp22.31 (OMIM: 300747), HEPCIDIN ANTIMICROBIAL PEPTIDE; HAMP Cytogenetic locations: 19q13.12 (OMIM: 606464), LEPTIN RECEPTOR; LEPR Cytogenetic locations: 1p31.3 (OMIM: 601007), KEARNS-SAYRE SYNDROME; KSS (OMIM: 530000), CYSTINOSIS, NEPHROPATHIC; CTNS CYSTINOSIS, INFANTILE NEPHROPATHIC, INCLUDED Cytogenetic locations: 17p13.2 (OMIM: 219800), WOLFRAM SYNDROME 1; WFS1 Cytogenetic locations: 4p16.1 (OMIM: 222300), EXCISION REPAIR, COMPLEMENTING DEFECTIVE, IN CHINESE HAMSTER, 5; ERCC5 Cytogenetic locations: 13q33.1 (OMIM: 133530), HIRSCHSPRUNG DISEASE, SUSCEPTIBILITY TO, 1; HSCR1 HIRSCHSPRUNG DISEASE, PROTECTION AGAINST, INCLUDED Cytogenetic locations: 10q11.21 (OMIM: 142623), ANDROGEN RECEPTOR; AR Cytogenetic locations: Xq12 (OMIM: 313700), SPINOCEREBELLAR ATAXIA 6; SCA6 Cytogenetic locations: 19p13.13 (OMIM: 183086), 312. #106210—ANIRIDIA 1; AN1 CATARACT, CONGENITAL, WITH LATE-ONSET CORNEAL DYSTROPHY, INCLUDED Cytogenetic locations: 11p13 (OMIM: 106210), FANCA GENE; FANCA Cytogenetic locations: 16q24.3 (OMIM: 607139), NUCLEAR RECEPTOR SUBFAMILY 5, GROUP A, MEMBER 1; NR5A1 Cytogenetic locations: 9q33.3 (OMIM: 184757), MELANOCORTIN 4 RECEPTOR; MC4R Cytogenetic locations: 18q21.32 (OMIM: 155541), TUMOR PROTEIN p63; TP63 Cytogenetic locations: 3q28 (OMIM: 603273), ADRENOLEUKODYSTROPHY; ALD ADRENOMYELONEUROPATHY, INCLUDED; AMN, INCLUDED Cytogenetic locations: Xq28 (OMIM: 300100), CEREBELLAR ATAXIA AND ECTODERMAL DYSPLASIA (OMIM: 212835), NESCIENT HELIX LOOP HELIX 2; NHLH2 Cytogenetic locations: 1p13.1 (OMIM: 162361), SPERMATOGENESIS- AND OOGENESIS-SPECIFIC BASIC HELIX-LOOP-HELIX PROTEIN 1; SOHLH1 Cytogenetic locations: 9q34.3 (OMIM: 610224), PSEUDOVAGINAL PERINEOSCROTAL HYPOSPADIAS; PPSH MICROPENIS, INCLUDED Cytogenetic locations: 2p23.1 (OMIM: 264600), ADRENAL HYPERPLASIA, CONGENITAL, DUE TO 17-ALPHA-HYDROXYLASE DEFICIENCY 17, 20-@LYASE DEFICIENCY, ISOLATED, INCLUDED Cytogenetic locations: 10q24.32 (OMIM: 202110), EUKARYOTIC TRANSLATION INITIATION FACTOR 2, SUBUNIT 3; EIF2S3 Cytogenetic locations: Xp22.11 (OMIM: 300161), SPHINGOSINE-1-PHOSPHATE LYASE 1; SGPL1 Cytogenetic locations: 10q22.1 (OMIM: 603729), 17-@BETA HYDROXYSTEROID DEHYDROGENASE III DEFICIENCY POLYCYSTIC OVARIAN DISEASE DUE TO 17-KETOSTEROID REDUCTASE DEFICIENCY, INCLUDED Cytogenetic locations: 9q22.32 (OMIM: 264300), PREMATURE OVARIAN FAILURE 1; POF1 Cytogenetic locations: Xq27.3 (OMIM: 311360), 46,XY SEX REVERSAL 1; SRXY1 46,XY TRUE HERMAPHRODITISM, SRY-RELATED, INCLUDED Cytogenetic locations: Yp11.2 (OMIM: 400044), MCCUNE-ALBRIGHT SYNDROME; MAS POLYOSTOTIC FIBROUS DYSPLASIA, INCLUDED; PFD, INCLUDED; POFD, INCLUDED Cytogenetic locations: 20q13.32 (OMIM: 174800) and/or ATR-X GENE; ATRX Cytogenetic locations: Xq21.1 (OMIM: 300032).

In the therapeutic applications of the present disclosure, administration can be in vitro (by contacting a peptide compound or a combination of peptide compounds to a cell in culture) or in vivo (by administering a peptide compound or a combination of peptide compounds to a subject comprising the cell). The subject can be a mammal and, in a further embodiment, a male. In an embodiment, the male is at least 30 years old or, in a further embodiment, at least 50 years old. Testosterone production in the males declines after the age of 30 years old and there is annual decline of 1-2% in total testosterone levels. Thus, testosterone replacement therapy (in this case induction of endogenous T production) could be applicable at any time when testosterone decline begins and/or the symptoms associated with testosterone decline (low libido and erection, low lean mass, reduced energy, central adiposity, lack of coping with stressors, etc. are indicative of testosterone decline). These symptoms are more prominent with aging and are more commonly seen in men over 50 where the cardiovascular disease, metabolic syndrome and depression are added in the list of the phenotypes associated with testosterone decline. Moreover, even at ages younger than 30 years old, the use of the therapeutic agent described herein could assist in cases of male infertility due to hypogonadism.

In the therapeutic applications described herein, the treated cell can be from or located in a testis and, in a further embodiment, the treated cell can be a Leydig cell. In another embodiment, the cell can be from or located in an ovary, an adrenal gland and/or a brain.

The therapeutic applications described herein can be used for the prevention, treatment and/or alleviation of symptoms of a condition associated with a decline in a steroid level. One exemplary condition associated to a decline in a steroid level is hypogonadism. Such conditions include, but are not limited to infertility, subfertility, aging, decreased libido, sexual dysfunction, altered mood, fatigue, decreased lean body mass, decreased bone mineral density, increased visceral fat, wasting or metabolic syndrome.

Alternatively or in combination, the therapeutic applications described herein can be used for the prevention, treatment and/or alleviation of symptoms associated with a condition associated to a decline in steroid levels, for example, a decline in neurosteroid levels. Such conditions include, but are not limited to anxiety disorders and depression, such as, for example, post-traumatic stress disorder.

Alternatively or in combination, the therapeutic applications described herein can be used for the prevention, treatment and/or alleviation of symptoms associated with a condition associated to a decline in steroid levels. Such conditions include, but are not limited to, depression, organ failure, cardiac muscle stiffness, low energy, abnormal hematocrit, sepsis, and coping with stressors.

In the context of the present disclosure, the peptide compounds or combinations are provided in a pharmaceutically or therapeutically effective amount to a subject (such as a mammal, including a human). The expressions "pharmaceutically effective amount" and "therapeutically effective amount" collectively refer to an amount (dose) effective in mediating a therapeutic benefit to a subject (for example prevention, treatment and/or alleviation of symptoms of hypogonadism). It is also to be understood herein that a "pharmaceutically effective amount" may be interpreted as an amount giving a desired therapeutic effect, either taken in one dose or in any dosage or route, taken alone or in combination with other therapeutic agents.

A therapeutically effective amount or dosage of the peptide compound of the present disclosure may range from about 0.001 to 1 000 µg/kg body weight, with other ranges of the invention including about 0.001 to 900 µg/kg body weight, about 0.001 to 800 µg/kg body weight, about 0.001 to 700 µg/kg body weight, about 0.001 to 600 µg/kg body weight, about 0.001 to 500 µg/kg body weight, about 0.001 to 450 µg/kg body weight, about 0.001 to 400 µg/kg body weight, about 0.001 to 350 µg/kg body weight, about 0.001 to 300 µg/kg body weight, about 0.001 to 250 µg/kg body weight, about 0.001 to 200 µg/kg body weight, about 0.001 to 150 µg/kg body weight, about 0.001 to 100 µg/kg body weight, about 0.001 to 90 µg/kg body weight, about 0.001 to 80 µg/kg body weight, about 0.001 to 70 µg/kg body weight, about 0.001 to 60 µg/kg body weight, about 0.001 to 50 µg/kg body weight, about 0.001 to 40 µg/kg body weight, about 0.001 to 30 µg/kg body weight, about 0.001 to 20 µg/kg body weight, about 0.001 to 10 µg/kg body weight, about 0.01 to 900 µg/kg body weight, about 0.01 to 800 µg/kg body weight, about 0.01 to 700 µg/kg body weight, about 0.01 to 600 µg/kg body weight, about 0.01 to 500 µg/kg body weight, about 0.01 to 450 µg/kg body weight, about 0.01 to 400 µg/kg body weight, about 0.01 to 350 µg/kg body weight, about 0.01 to 300 µg/kg body weight, about 0.01 to 250 µg/kg body weight, about 0.01 to 200 µg/kg body weight, about 0.01 to 150 µg/kg body weight, about 0.01 to 100 µg/kg body weight, about 0.01 to 90 µg/kg body weight, about 0.01 to 80 µg/kg body weight, about 0.01 to 70 µg/kg body weight, about 0.01 to 60 µg/kg body weight, about 0.01 to 50 µg/kg body weight, about 0.01 to 40 µg/kg body weight, about 0.01 to 30 µg/kg body weight, about 0.01 to 20 µg/kg body weight, about 0.01 to 10 µg/kg body weight, about 0.1 to 900 µg/kg body weight, about 0.1 to 800 µg/kg body weight, about 0.1 to 700 µg/kg body weight, about 0.1 to 600 µg/kg body weight, about 0.1 to 500 µg/kg body weight, about 0.1 to 450 µg/kg body weight, about 0.1 to 400 µg/kg body weight, about 0.1 to 350 µg/kg body weight, about 0.1 to 300 µg/kg body weight, about 0.1 to 250 µg/kg body weight, about 0.1 to 200 µg/kg body weight, about 0.1 to 150 µg/kg body weight, about 0.1 to 100 µg/kg body weight, about 0.1 to 90 µg/kg body weight, about 0.1 to 80 µg/kg body weight, about 0.1 to 70 µg/kg body weight, about 0.1 to 60 µg/kg body weight, about 0.1 to 50 µg/kg body weight, about 0.1 to 40 µg/kg body weight, about 0.1 to 30 µg/kg body weight, about 0.1 to 20 µg/kg body weight, about 0.1 to 10 µg/kg body weight, about 1 to 900 µg/kg body weight, about 1 to 800 µg/kg body weight, about 1 to 700 µg/kg body weight, about 1 to 600 µg/kg body weight, about 1 to 500 µg/kg body weight, about 1 to 450 µg/kg body weight, about 1 to 400 µg/kg body weight, about 1 to 350 µg/kg body weight, about 1 to 300 µg/kg body weight, about 1 to 250 µg/kg body weight, about 1 to 200 µg/kg body weight, about 1 to 150 µg/kg body weight, about 1 to 100 µg/kg body weight, about 1 to 90 µg/kg body weight, about 1 to 80 µg/kg body weight, about 1 to 70 µg/kg body weight, about 1 to 60 µg/kg body weight, about 1 to 50 µg/kg body weight, about 1 to 40 µg/kg body weight, about 1 to 30 µg/kg body weight, about 1 to 20 µg/kg body weight or about 1 to 10 µg/kg body weight.

When more than one peptide compounds is used, the therapeutic effective amount of the total weight of the peptides compounds may range from about 0.001 to 1 000 µg/kg body weight, with other ranges of the invention including about 0.001 to 900 µg/kg body weight, about 0.001 to 800 µg/kg body weight, about 0.001 to 700 µg/kg body weight, about 0.001 to 600 µg/kg body weight, about 0.001 to 500 µg/kg body weight, about 0.001 to 450 µg/kg body weight, about 0.001 to 400 µg/kg body weight, about 0.001 to 350 µg/kg body weight, about 0.001 to 300 µg/kg body weight, about 0.001 to 250 µg/kg body weight, about 0.001 to 200 µg/kg body weight, about 0.001 to 150 µg/kg body weight, about 0.001 to 100 µg/kg body weight, about 0.001 to 90 µg/kg body weight, about 0.001 to 80 µg/kg body weight, about 0.001 to 70 µg/kg body weight, about 0.001 to 60 µg/kg body weight, about 0.001 to 50 µg/kg body weight, about 0.001 to 40 µg/kg body weight, about 0.001 to 30 µg/kg body weight, about 0.001 to 20 µg/kg body weight, about 0.001 to 10 µg/kg body weight, about 0.01 to 900 µg/kg body weight, about 0.01 to 800 µg/kg body weight, about 0.01 to 700 µg/kg body weight, about 0.01 to 600 µg/kg body weight, about 0.01 to 500 µg/kg body weight, about 0.01 to 450 µg/kg body weight, about 0.01 to 400 µg/kg body weight, about 0.01 to 350 µg/kg body weight, about 0.01 to 300 µg/kg body weight, about 0.01 to 250 µg/kg body weight, about 0.01 to 200 µg/kg body weight, about 0.01 to 150 µg/kg body weight, about 0.01 to 100 µg/kg body weight, about 0.01 to 90 µg/kg body weight, about 0.01 to 80 µg/kg body weight, about 0.01 to 70 µg/kg body weight, about 0.01 to 60 µg/kg body weight, about 0.01 to 50 µg/kg body weight, about 0.01 to 40 µg/kg body weight, about 0.01 to 30 µg/kg body weight, about 0.01 to 20 µg/kg body weight, about 0.01 to 10 µg/kg body weight, about 0.1 to 900 µg/kg body weight, about 0.1 to 800 µg/kg body weight, about 0.1 to 700 µg/kg body weight, about 0.1 to 600 µg/kg body weight, about 0.1 to 500 µg/kg body weight, about 0.1 to 450 µg/kg body weight, about 0.1 to 400 µg/kg body weight, about 0.1 to 350 µg/kg body weight, about 0.1 to 300 µg/kg body weight, about 0.1 to 250 µg/kg body weight, about 0.1 to 200 µg/kg body weight, about 0.1 to 150 µg/kg body weight, about 0.1 to 100 µg/kg body weight, about 0.1 to 90 µg/kg body weight, about 0.1 to 80 µg/kg body weight, about 0.1 to 70 µg/kg body weight, about 0.1 to 60 µg/kg body weight, about 0.1 to 50 µg/kg body weight, about 0.1 to 40 µg/kg body weight, about 0.1 to 30 µg/kg body weight, about 0.1 to 20 µg/kg body weight, about 0.1 to 10 µg/kg body weight, about 1 to 900 µg/kg body weight, about 1 to 800 µg/kg body weight, about 1 to 700 µg/kg body weight, about 1 to 600 µg/kg body weight, about 1 to 500 µg/kg body weight, about 1 to 450 µg/kg body weight, about 1 to 400 µg/kg body weight, about 1 to 350 µg/kg body weight, about 1 to 300 µg/kg body weight, about 1 to 250 µg/kg body weight, about 1 to 200 µg/kg body weight, about 1 to 150 µg/kg body weight, about 1 to 100 µg/kg body weight, about 1 to 90 µg/kg body weight, about 1 to 80 µg/kg body weight, about 1 to 70 µg/kg body weight, about 1 to 60 µg/kg body weight, about 1 to 50 µg/kg body weight, about 1 to 40 µg/kg body weight, about 1 to 30 µg/kg body weight, about 1 to 20 µg/kg body weight or about 1 to 10 µg/kg body weight.

In some embodiments, the peptide compounds or the combinations of the present disclosure are provided as pharmaceutical compositions comprising a carrier. In accordance with the present invention, a "carrier" or "pharmaceutical carrier" is a pharmaceutically acceptable solvent, suspending agent or any other pharmacologically inert vehicle for delivering one or more peptide compounds to a subject. The carrier is typically liquid or solid. A pharmaceutical carrier is generally selected to provide for the desired bulk, consistency, etc., when combined with components of a given pharmaceutical composition, in view of the intended administration mode. Typical pharmaceutical carriers include, but are not limited to binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Peptide compounds of the present disclosure may be administered with a pharmaceutically-acceptable diluent, carrier, or excipient, in one or more unit dosage form. Conventional pharmaceutical practice may be employed to provide suitable formulations or compositions to administer such compositions to subjects. Although oral administration is preferred, any appropriate route of administration may be employed, for example, intravenous, parenteral, subcutaneous, intramuscular, intracranial, intraorbital, ophthalmic, intraventricular, intracapsular, intraspinal, intrathecal, epidural, intracisternal, intraperitoneal, intranasal, transdermal or aerosol administration. Formulations may be in the form of liquid solutions or suspension, tablets, capsules, powders for reconstitution, etc.

Methods well known in the art for making formulations are found in, for example, Remington: The Science and Practice of Pharmacy, (19th ed.) ed. A. R. Gennaro A R., 1995, Mack Publishing Company, Easton, PA. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, (e.g., lactose) or may be aqueous solutions containing, for example, polyoxyethylene-9-lauryl ether, glycocholate and deoxycholate, or may be oily solutions for administration in the form of nasal drops, or as a gel.

The peptides compounds, combinations and pharmaceutical compositions of the present disclosure are used to prevent, treat or alleviation the symptoms of a condition associated with hypogonadism. The expression "prevention, treatment or alleviation of symptoms" refer to the ability of the peptide compounds, the combinations and the pharmaceutical compositions to limit the development, progression and/or symptomology of hypogonadism. Broadly, the prevention, treatment and/or alleviation of symptoms encompass the reduction of symptoms associated with hypogonadism, such as, for example, infertility (due to defective or insufficient spermatogenesis or ovulation), aging, decreased libido, sexual dysfunction, altered mood, fatigue, decreased lean body mass, decreased bone mineral density, increased visceral fat, wasting and/or metabolic syndrome.

The peptide compounds and combinations of the present disclosure may be administered once, twice, thrice or more than once a day to achieve the desired therapeutic endpoint. Since the maximal effect of the peptide compounds of the present disclosure occur between 2 to 3 hours post-administration, the peptide compounds of the present disclosure can be administered once, twice, thrice or even four times a day. In some embodiments, the peptide compounds of the present disclosure are administered once a day. In some additional embodiments, the peptide compounds of the present disclosure are administered twice a day. In some further embodiments, the peptide compounds of the present disclosure are administered thrice a day. In some yet additional embodiments, the peptide compounds of the present disclosure are administered four times a day. In some additional embodiments, the peptide compounds or the combinations can be administered in the evening or at night. Alternatively of in combination, the peptide compounds can be administered in the morning.

The present invention will be more readily understood by referring to the following examples which are given to illustrate the invention rather than to limit its scope.

Example I—Testosterone Inducing Peptides

Peptides. Peptides were obtained from CanPeptide (Montreal, Quebec) with >95% purity. All peptides were dissolved in molecular grade, sterile double distilled water to obtain a 1 mM stock solution and stored at −20° C. Peptides used for oral screenings were prepared from 1 mM peptide stock and diluted in sterile tap water in a total volume of 1 mL. Peptides used for pharmacokinetic experiments were diluted at 10 mg/ml using sterile tap water. Some of the peptides were chemically modified after synthesis. The following table summarizes the peptides that have been tested:

TABLE 3

Description of the peptides and the peptide derivatives synthesized in this Example. The symbol "d" in the amino acid core refers to the use of a D-enantiomer of the residue following the symbol. The symbol "Ac" used throughout the specification refers to an acetyl cap. The symbol "NH$_2$" used throughout the specification refers to an amide cap. The symbol "miniPEG" used throughout the specification refers to the presence of mini PEGylated chain (NH$_2$—CH$_2$—CH$_2$—O—CH$_2$—CH$_2$—O—CH$_2$—CO—C$_{26}$H$_{49}$N$_9$O$_{10}$ (647.80 Da)).

| # | Amino acid modification | Amino acid core | SEQ ID NO: of amino acid core | Carboxy modification |
|---|---|---|---|---|
| 1 | None | KVSQ | 1 | None |
| 2 | Acetyl cap | KVSQ | 1 | NH$_2$ capped glutamine |
| 3 | None | RVTQ | 2 | None |
| 4 | None | RVTQdS | 13 | NH$_2$ capped serine |
| 5 | None | RVTQdS | 13 | NH$_2$ capped serine |
| 6 | Acetyl cap | RVTQdS | 13 | None |
| 7 | Mini PEG | RVTQdS | 13 | NH$_2$ capped serine |
| 8 | None | SRVTQ | 17 | None |
| 9 | None | dSRVTQdS | 23 | None |
| 10 | None | RdVTQ | 3 | None |
| 11 | Acetyl cap | RdVTQ | 3 | NH$_2$ capped glutamine |
| 12 | None | RdVdTQ | 22 | None |
| 13 | Mini PEG | RVTQ | 2 | None |
| 14 | None | RVSQ | 5 | None |
| 15 | Acetyl cap | RVSQ | 5 | NH$_2$ capped glutamine |
| 16 | None | RVdSQ | 7 | None |
| 17 | None | RdVSQ | 6 | None |
| 18 | None | RITQ | 8 | None |
| 19 | Acetyl cap | RlTQdS | 15 | NH$_2$ capped serine |
| 20 | Acetyl cap | RdITQ | 9 | NH$_2$ capped glutamine |
| 21 | Mini PEG | RITQ | 8 | NH$_2$ capped glutamine |
| 22 | None | RITQ | 8 | NH$_2$ capped glutamine |
| 23 | None | RdITQ | 9 | None |
| 24 | None | KITQ | 10 | None |
| 25 | Acetyl cap | KITQ | 10 | NH$_2$ capped glutamine |
| 26 | None | KITQ | 10 | NH$_2$ capped glutamine |
| 27 | Acetyl cap | KdITQ | 11 | NH$_2$ capped glutamine |
| 28 | None | RISQ | 16 | None |
| 29 | Acetyl cap | RISQ | 16 | NH$_2$ capped glutamine |
| 30 | None | RLTQ | 18 | None |
| 31 | Acetyl cap | RLTQ | 18 | NH$_2$ capped glutamine |
| 32 | None | KISQ | 19 | None |
| 33 | Acetyl cap | KISQ | 19 | NH$_2$ capped glutamine |
| 34 | Acetyl cap | KdlSQ | 20 | NH$_2$ capped glutamine |
| 35 | None | RVTE | 21 | None |

TABLE 3-continued

Description of the peptides and the peptide derivatives synthesized in this Example. The symbol "d" in the amino acid core refers to the use of a D-enantiomer of the residue following the symbol. The symbol "Ac" used throughout the specification refers to an acetyl cap. The symbol "NH$_2$" used throughout the specification refers to an amide cap. The symbol "miniPEG" used throughout the specification refers to the presence of mini PEGylated chain (NH$_2$–CH$_2$–CH$_2$–O–CH$_2$–CH$_2$–O–CH$_2$–CO–C$_{26}$H$_{49}$N$_9$O$_{10}$ (647.80 Da)).

| # | Amino acid modification | Amino acid core | SEQ ID NO: of amino acid core | Carboxy modification |
|---|---|---|---|---|
| 36 | Acetyl cap | RVTE | 21 | NH$_2$ capped glutamine |
| 37 | None | KVTQ | | None |
| 38 | Acetyl cap | KVTQ | | NH$_2$ capped glutamine |
| 39 | Acetyl cap | RITQ | | NH$_2$ capped glutamine |

Osmotic pumps. Model 2006 osmotic pumps, infusing 0.15 µL/hr, were purchased from Alzet (Cupertino, CA). The peptide concentration loaded into the pumps was adjusted to deliver the doses indicated in each figure. The pump infusion rates varied by production lot and were adjusted accordingly. Pumps were loaded 24 hrs prior to surgical implantation under sterile conditions and were kept at 37° C. in PBS.

Animal handling, blood collections, surgical procedures, and oral administration of peptides. Brown-Norway rats aged 22-28, 36-42, or 50-56 days-old were purchased from Charles River Laboratories (Senneville, Quebec) and aged until needed. Rats were kept on a 12 L/12 D day cycle with lights on at 7 AM and access to food and water ad libitum.

For all experiments, plasma samples were obtained via percutaneous jugular puncture and collected in EDTA KE/1.3 tubes (Sarstedt, Numbrecht, Germany, Cat #5072511). Blood collection time points are indicated in each figure legend. Samples were centrifuged at 1 300 RCF for 10 min, and the plasma was stored in 2 mL Wheaton glass vials (Fisher Scientific, Hampton, NH, Cat #03 337 21A) and kept at −20° C. until needed.

Brown-Norway rats aged ~29 day-old were implanted with osmotic infusion pumps in the interscapular region under general anesthesia with isoflurane following antisepsis using iodine. The surgical wound was closed with two to three staples that were removed a week after the surgery. Subcutaneous carprofen (Zoetis, Parsippany, NJ) was given before the surgical procedure and in the following two days for pain management.

For all oral experiments, administration via gavage began between 8:30-8:50 am with a 3-minute delay between each rat. Animals used for pharmacokinetic studies were fasted for 4 hrs before starting gavage at 1 pm with a 3-minute delay between each rat.

Animals were handled according to protocols approved by the McGill University Animal Care and Use Committee, which included standard operation procedures for repetitive jugular collections.

Plasma steroid measurements. Testosterone levels were measured using Cayman (Ann Arbor, MI) EIA kit Cat #582701, and corticosterone levels were measured using Cayman EIA kit Cat #501320. All samples were measured in duplicate according to the manufacturer's instructions. Samples were diluted until the average control levels fitted the middle of the standard curve. The number of animals used for each experiment is noted in the corresponding figure legend.

Peptide stability in plasma, oral pharmacokinetics, and quantification. For peptide stability experiments, plasma from Brown-Norway rats age 90-140 days was collected and stored at −20° C. until further use. The plasma was thawed, spun at 12 000 RPM for 10 min, and kept at 4° C. 4 µM of the various peptides were incubated with 100 µL of plasma that was warmed at 37° C. for 10 min before use. After 1, 15, 30, 60, 90 or 120 minutes, the plasma/peptide samples were crashed with 300 µL of 100% methanol, spun at 14 000 RPM for 10 min, and the supernatant collected. The methanol in the supernatant was evaporated and the samples were re-extracted. The final pellet was solubilized in 5 µL methanol followed by the addition of 100 µL of sterile double distilled water. The extracted samples were transferred to plastic tubes and placed in the autoloader of the mass spectrometer.

For oral pharmacokinetic experiments, jugular blood samples were collected following a single oral dose of 10 mg peptide in 1 ml of vehicle after 5, 15, 30, 45, 60, 90, and 120 minutes. Protein inhibitor cocktail (ROCHE, cOmplete protein inhibitors, Cat #11697498001), which was added into the EDTA collection tubes, was used for KVSQ and RVTQ peptides. Plasma was immediately extracted, and 100 µL of plasma were crashed with 300 µL of 100% methanol, spun at 14 000 RPM for 10 min, and the supernatant harvested. Re-extraction of the precipitant and solubilization of the pellet were as described above.

The analytical instrumentation consisted of a Thermo-Scientific ISQ Quantiva Triple Quadrupole Mass Spectrometer (QQQ), incorporating a heated electrospray ionization (HESI) source, and a Thermo-Scientific UltiMate™ 3000 UHPLC system (including, UltiMate™ 3000 RS autosampler). Analytical conditions were developed using a reference standard in a solution containing 5 µM of the corresponding peptide. The chromatography was resolved by isocratic elution of a binary solvent system incorporating (A) 0.1% Formic Acid (aq) and (B) ACN+0.1% FA and using an Agilent Eclipse Plus™ C18 analytical column (100 mm×2.1 mm ID, 1.8 µm particle). A 5 µL injection volume and solvent flow rate of 150 µL/min were used. The MS/MS acquisition time was 7 min and total run time was 8.3 min/injection. The triple Quadrupole MS/MS instrumentation conditions were as follows: the HESI source voltage was 3200 V, the sheath gas 30 L/min, auxiliary gas 20 L/min, sweep gas 2.0 L/min, the ion transfer temperature was 350° C., the vaporizer temperature was 350° C., the CID gas 1.5 (mTorr) and the dwell time was 100 msec. The Q1 Resolution (FWHM) was 0.4 (unitless) and the Q3 resolution (FWHM) was 0.7 (unitless). The instrument ran in a selected reaction monitoring (SRM), positive ion detection mode at various collision energies (CE) for the following mass transitions:

Ac-RITQdS-NH2: p84 (m/z 645→m/z 295, m/z 396)
RdVTQ: p72 (m/z 503→m/z 211).
Ac-RdITQ-NH2: p87 (m/z 558→m/z 391, m/z 267)
RVTQ: p64 (m/z 503→m/z 211; m/z 503→m/z 357 and m/z 503→m/z 256)
KVSQ: p95 (m/z 461→m/z 129) and (m/z 461→m/z 234)

Statistical analysis. GraphPad Prism 7.04 (GraphPad Software, La Jolla, CA) and Excel 2006 (Microsoft Corporation, Redmond, WA) were used to generate graphs, heatmap, curve fitting, and statistical analysis. ANOVA or a one-tail t-test was used to determine significant changes. The number of animals used per experiment is noted in each of the corresponding figure legends. Data are shown as mean±standard deviation unless otherwise specified in the figure legend.

Subcutaneous Infusion of RVTQ and its Evolutionary-Related Sequences Increase Circulating Testosterone Levels Brown-Norway rats were implanted with subcutaneous infusion pumps at ~29 days old. Blood samples collected when the rats were ~56 days old, and those receiving a peptide concentration of 377 ng/kg/day showed a significant increase in testosterone levels (FIG. 1A).

The UniProt database and Clustal Omega were used to search for sequence variants of the N163-166 core found in nature. We identified RVSQ, RITQ, and KITQ (underline denotes the amino acid changes) as variations of the core sequence found mainly in fish and worms (FIG. 1B). The sequence alignment also showed that the N-terminus amino acid flanking the N163-166 core was occupied by a serine or asparagine while the amino acid flanking the C-terminus was a serine, which was conserved in all the analyzed sequences. Moreover, all the amino acid changes identified were substituted for structurally similar amino acids.

To test whether these RVTQ-related sequences increased testosterone levels, ~27-day old Brown-Norway rats were implanted with subcutaneous infusion pumps delivering the three evolutionary variants RVSQ, RITQ, and KITQ. FIG. 1C shows that samples collected at age 54 days, where the dose of KITQ reached ~370 ng/kg/day, had a significant increase in circulating testosterone levels. Samples collected 11 days after, at age 65 days when the concentration delivered was ~330 ng/kg/day, also showed a significant increase in RITQ. These results show that the core RVTQ is permissible to modifications and may allow for modulation of the target site.

Oral Delivery of Small Molecule Peptides Increases Testosterone Levels

To ascertain whether RVTQ or its modified derivatives can be delivered orally, an animal model was developed where various modifications can be screened efficiently and identify those that were orally active. Six derivatives of RVTQ were tested in Brown-Norway rats age 60 to 123 days old, which were gavaged in the morning, followed by jugular blood sample collection 3 hrs later. RVTQ was used as control and tested modifications that included the addition of a flanking D-serine, amide cap at the carboxy terminus and the addition of miniPEG or an acetyl cap at the N-terminus. The modifications were tested at random with doses ranging from 160 to 1 200 µg/kg. FIG. 2A shows that, RVTQdS-NH$_2$ (SEQ ID NO: 6) composed of the core RVTQ (SEQ ID NO: 2) sequence plus D-serine and an amide cap at the carboxy terminus, administered at ~580 µg/kg, was the combination of dose and modification that significantly increased testosterone levels. While RVTQdS-NH$_2$ (SEQ ID NO: 6) increased testosterone levels, the naked RVTQ (SEQ ID NO: 2) sequence did not show an effect at the 3 hrs sampling time.

Figure 2B:
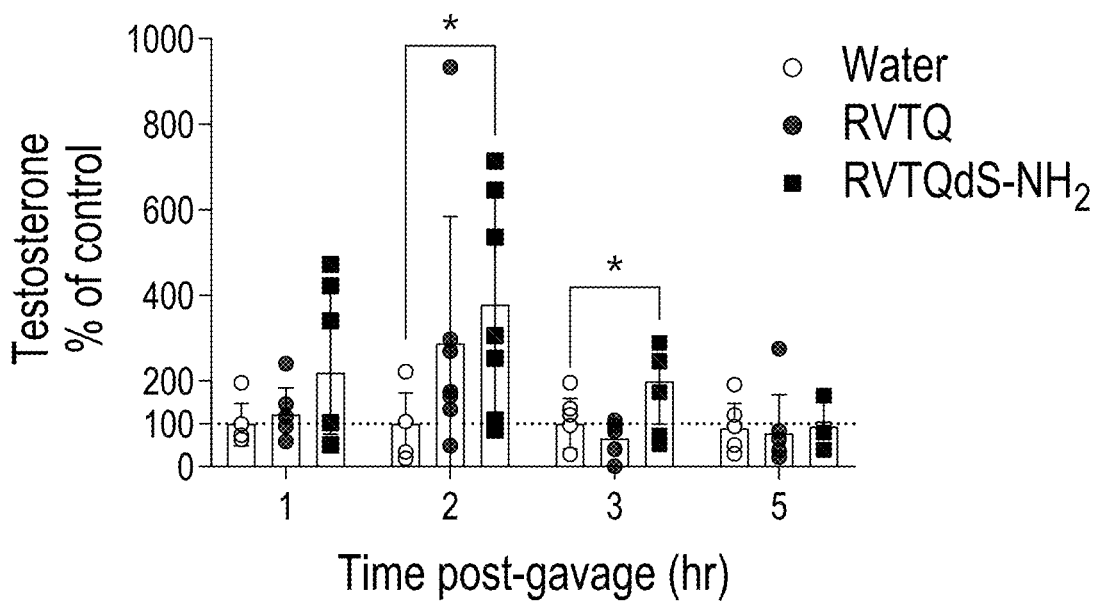

It was then ascertained the best sampling time to identify significant increases in testosterone after oral administration. Rats were treated in two rounds with ~580 µg/kg of RVTQ or RVTQdS-NH$_2$ and collected blood samples at 1 and 3 hrs or 2 and 5 hrs (FIG. 2B). The pooled data showed a time-dependent increase in testosterone levels that were significant at 2 and 3 hrs post-treatment. The data also showed that rats treated with RVTQdS-NH$_2$ showed the best significant increase in testosterone levels after 2 hr. Based on these data, the dose and collection time points of further screenings were adjusted to ~550 µg/kg and 2 hrs, respectively.

Oral Treatment with Modified Derivatives of RVTQ and Evolutionary-Related Core Sequences Increases Circulating Testosterone Levels To identify other sequence/modifications with oral activity, a series of peptides composed of changes to the core RVTQ sequence and its evolutionary relatives were designed. Additionally, the core sequences that included R>K changes in the first amino acid, V>I or L changes in the second position, T>S substitution in the third position, and Q>E in the fourth position were tested. This resulted in 10 core peptide sequences. The core sequences were further modified to include the addition of miniPEG or acetyl group to the N-terminus, use of D-amino acids, and capping of the C-terminus with an amide group.

Figure 3G:
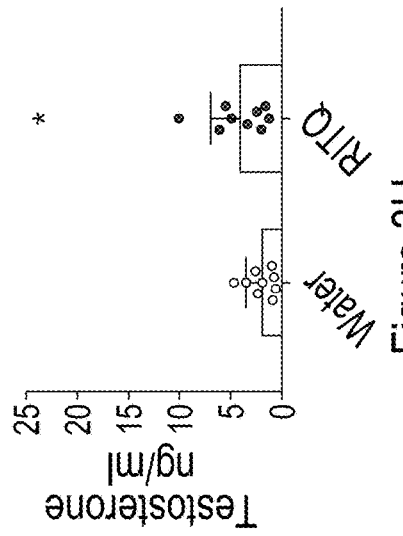
Figure 3H:
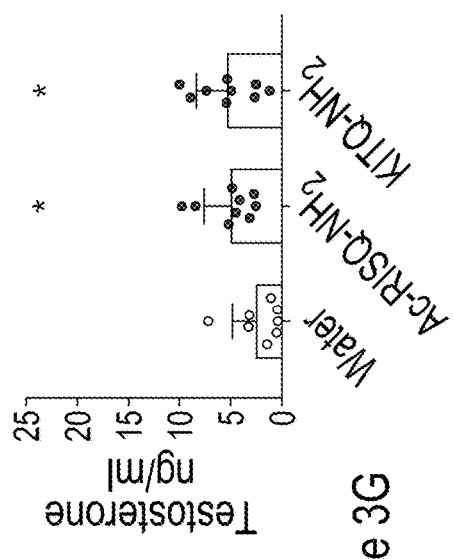
Figure 3I:
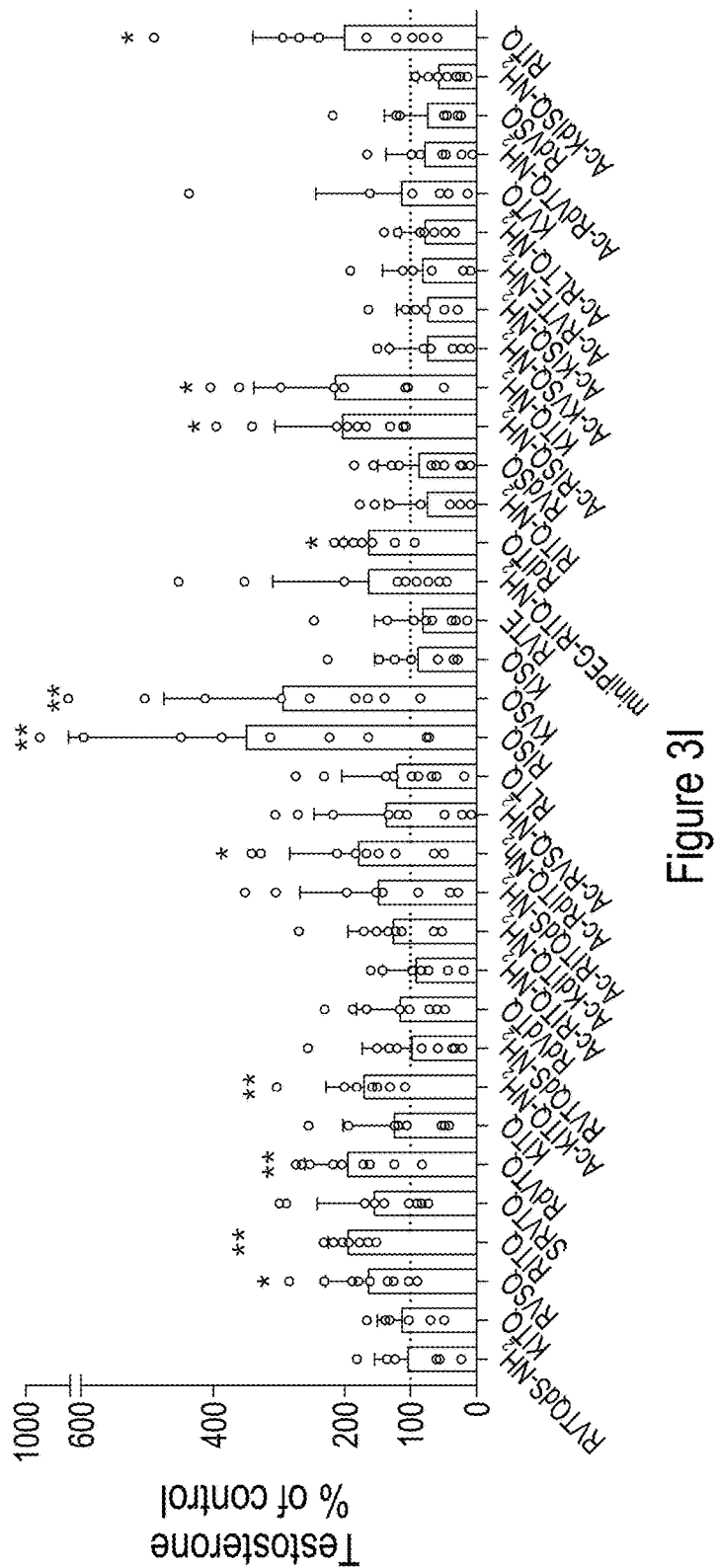
Figure 10:
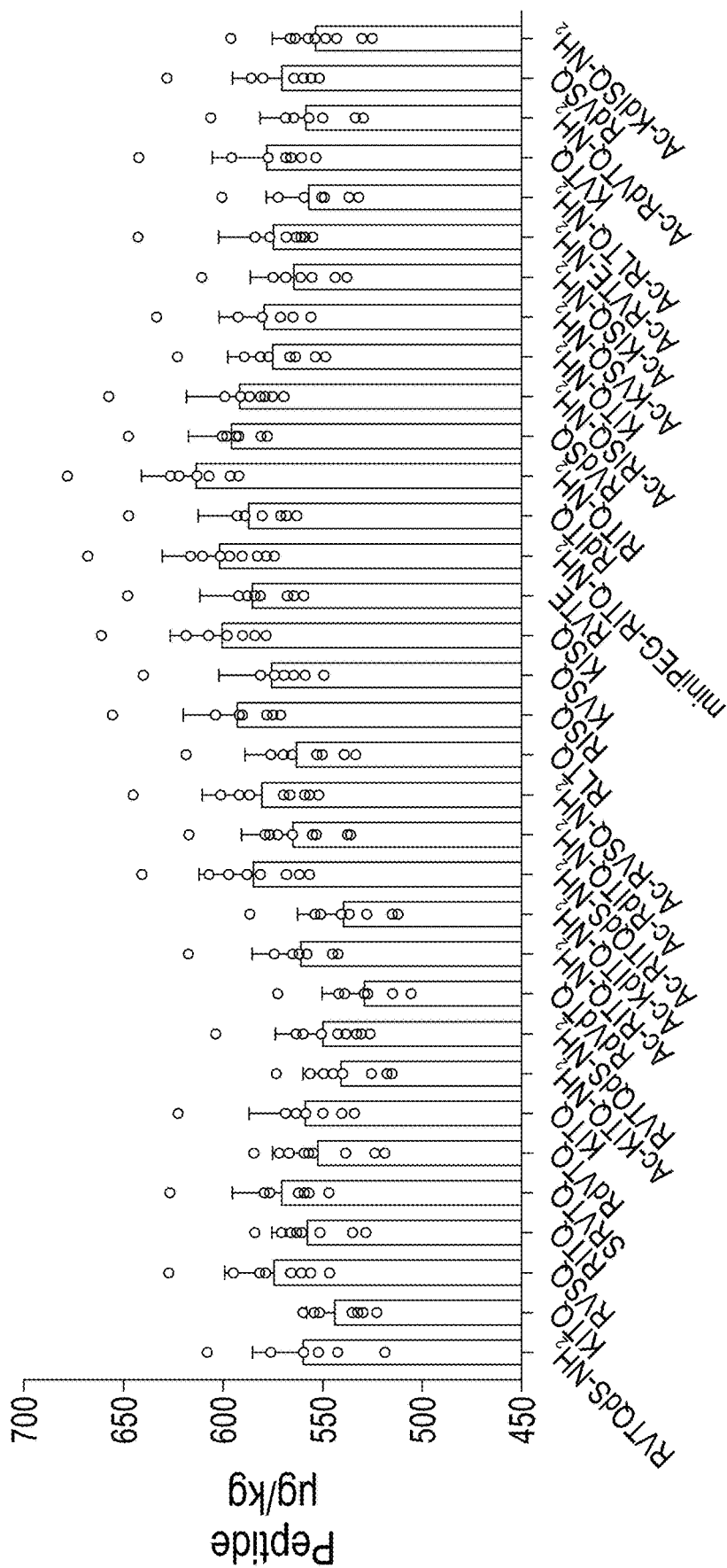
FIG. 10 shows the doses used during the oral screening experiment for each peptide tested.
Figure 11I:
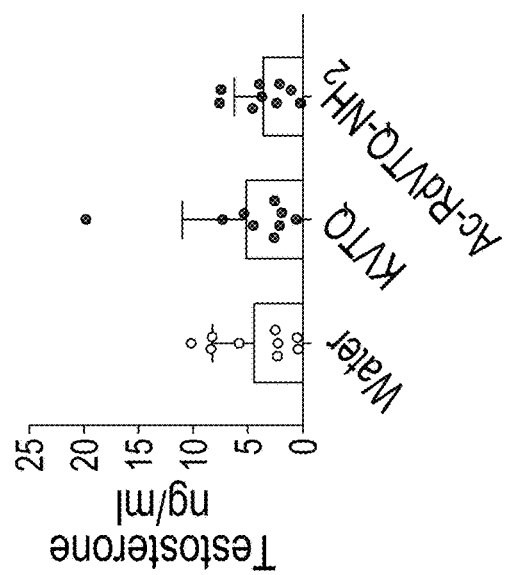
Figure 11H:
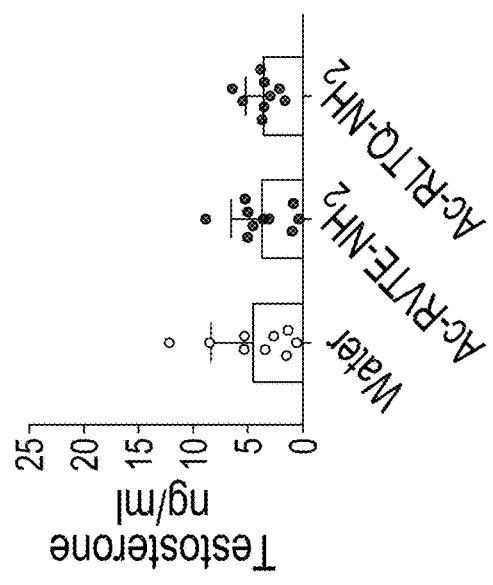
Figure 11J:
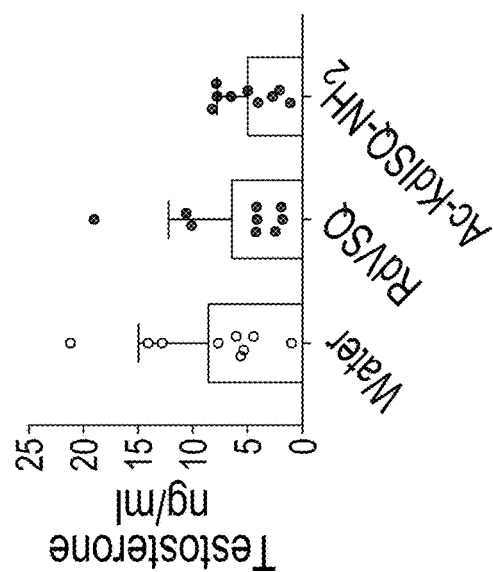
Figure 11G:
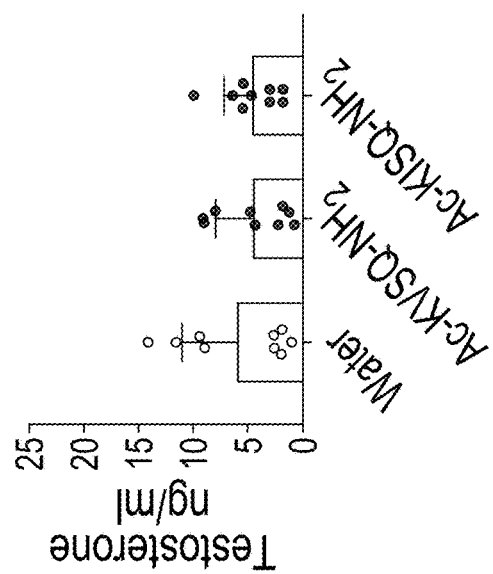
Figure 12I:
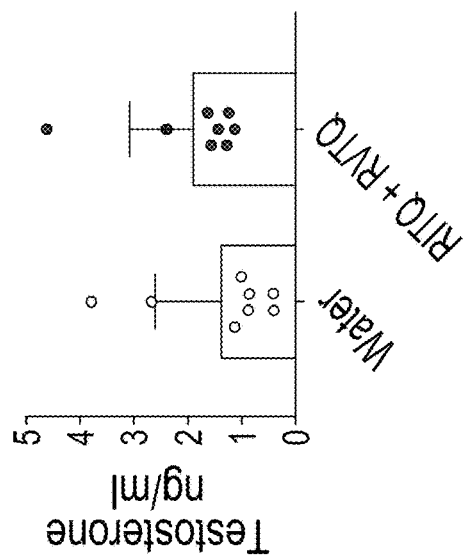
Figure 12H:
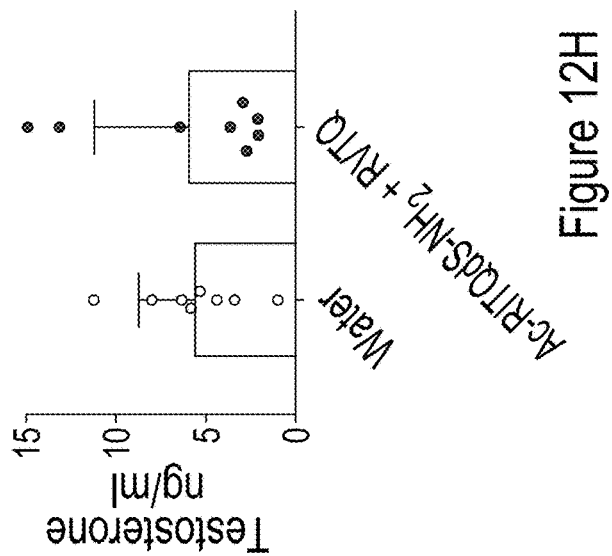
Figure 12G:
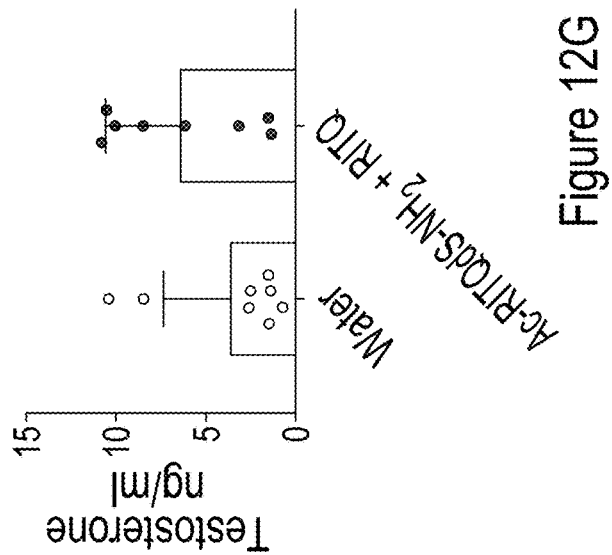

Brown-Norway rats age 60 to 136 days, which were gavaged twice per week with the various peptides were used. Each test was composed of three groups, a control and two peptide combinations, with a total of 34 peptides screened. The various peptides were gavaged with doses that ranged from 550 to 620 µg/kg, followed by blood sampling at two hrs (FIG. 10). The screening identified 11 core/peptide modifications that increased testosterone levels (FIGS. 3A-G), with the remaining showing no change or non-significant decreases (FIGS. 11A-K). It was confirmed that the animals still responded to the oral peptides by using RITQ, in the last test where significant increases in testosterone were observed (FIG. 3H). FIG. 3I summarizes data where the peptide treatment data were normalized to their respective control testosterone levels and presented in the ordered tested.

Dose-Response Studies and Low Dosing

Figure 4A:
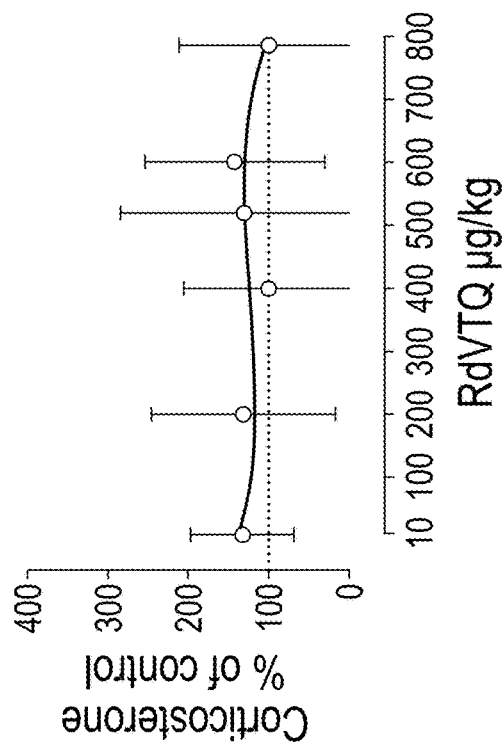
FIGS. 4A to 4D show a biphasic response in some peptides.
Figure 4B:
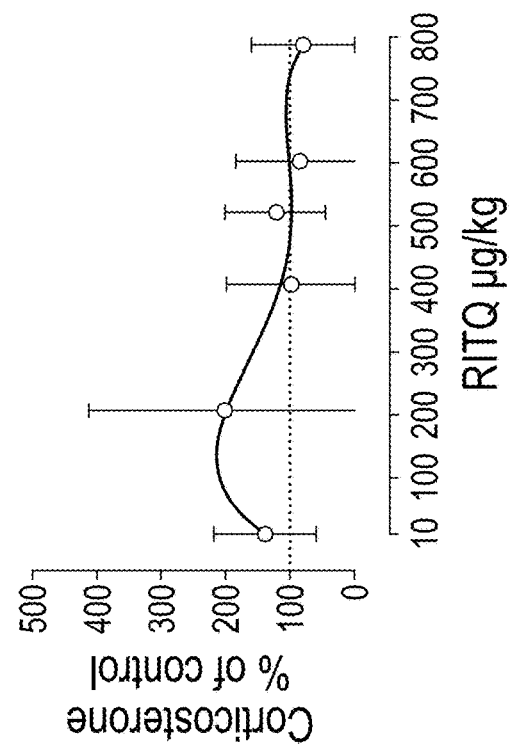
Figure 4C:
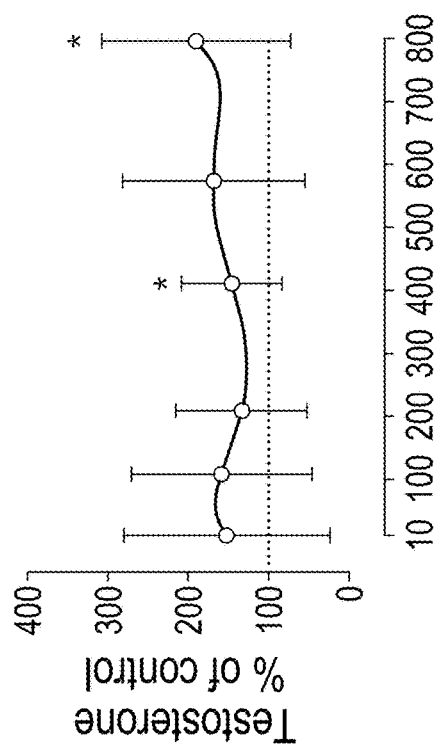
Figure 4D:
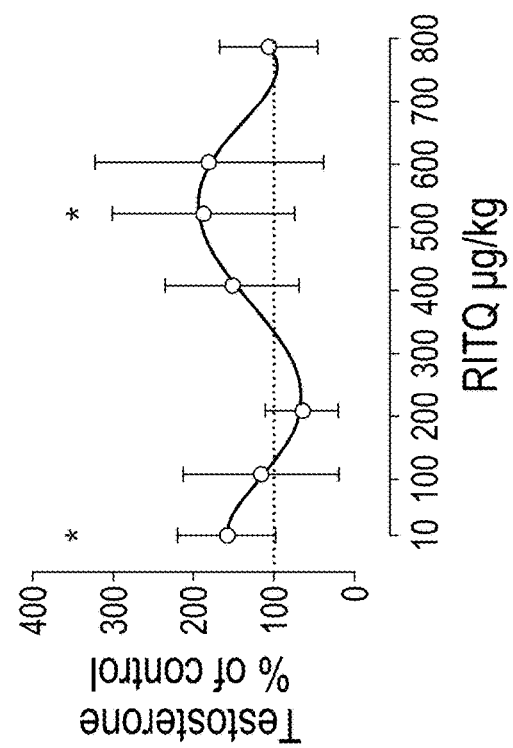

To gain further insights into the dose-response profiles of the peptides identified, we tested RdVTQ and RITQ in rats gavaged each day with increasing concentrations from age 88 to 138 days. The results showed that RdVTQ had significant increases at ~400 µg/kg and 800 µg/kg doses (FIG. 4A). While RITQ showed a biphasic profile for testosterone, characterized by a significant increase at the low dose of 10 µg/kg, a non-significant decrease at ~220 µg/kg, and a significant increase at ~520 µg/kg (FIG. 4C), no corresponding significant changes in corticosterone levels were observed (FIGS. 4B & D).

Figure 5:
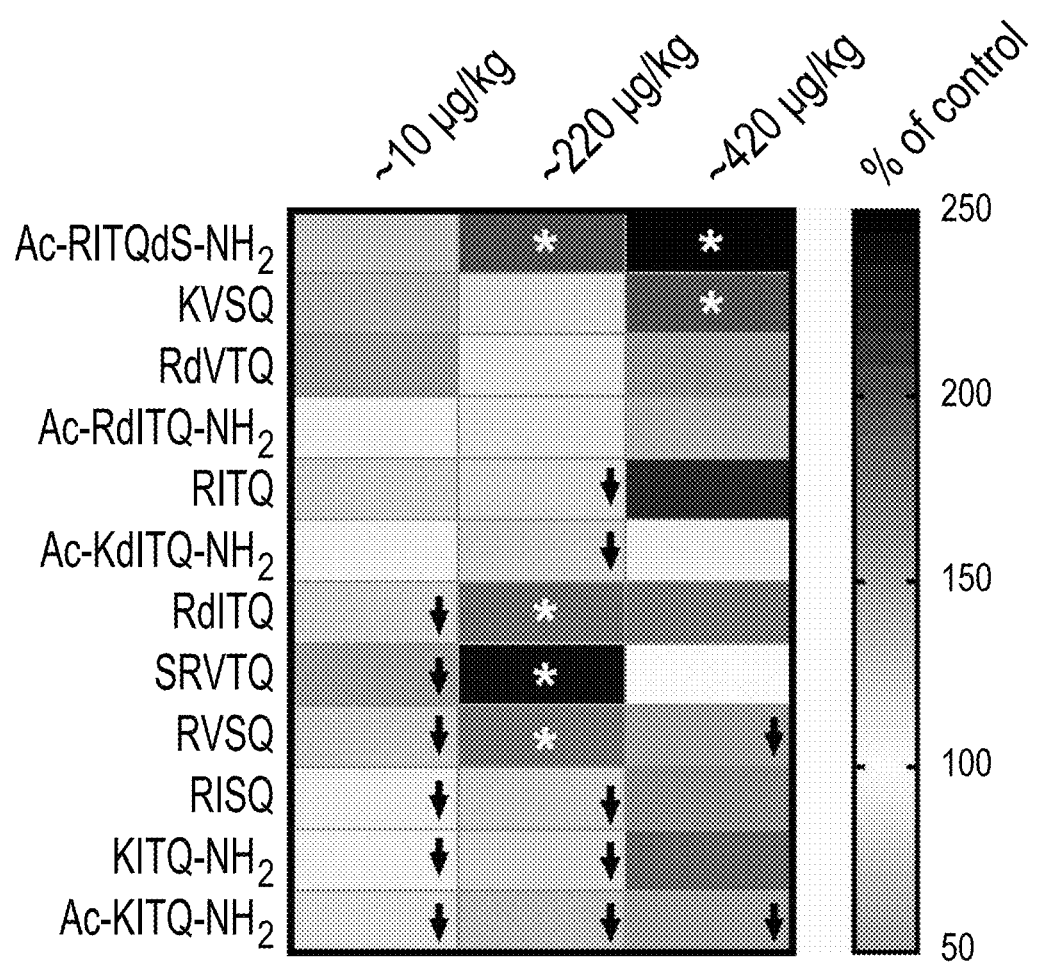
FIG. 5 shows the identification of oral peptides with robust profiles. Heat map depicting the mean percent plasma testosterone levels with respect to control levels in rats 2 hrs after treatment with the various peptides and concentrations. Rats treated with ~10 and 220 µg peptide/kg had N=7 and N=6 for ~420 µg peptide/kg. Age of Brown-Norway rats during experiment was 82-131 days-old; *p<0.05.

The previous dose-response experiment with RITQ indicated that the mechanism of action driving the steroidogenic effects might be subjected to biphasic responses. To ascertain whether the 11 orally-active candidates exhibited a biphasic response around the 220 µg/kg dose, an experiment composed of four groups of rats aged 82-131 days was set up. This oral assay tested the steroidogenic effects of 13 peptides dosed at ~10, 220, or 420 µg/kg after two hrs. The results showed that Ac-RITQdS-NH$_2$, KVSQ, RdVTQ, and Ac-RdITQ-NH$_2$ increased average testosterone levels, with some doses showing significance (FIG. 5). Several other peptides were identified where testosterone levels decreased at the 10, 220 or 420 µg/kg doses (down arrows). In addition, these results identified peptide candidates that increased testosterone levels around 420 µg/kg and at the low dose of 10 µg/kg, although not significantly.

Figure 6G:
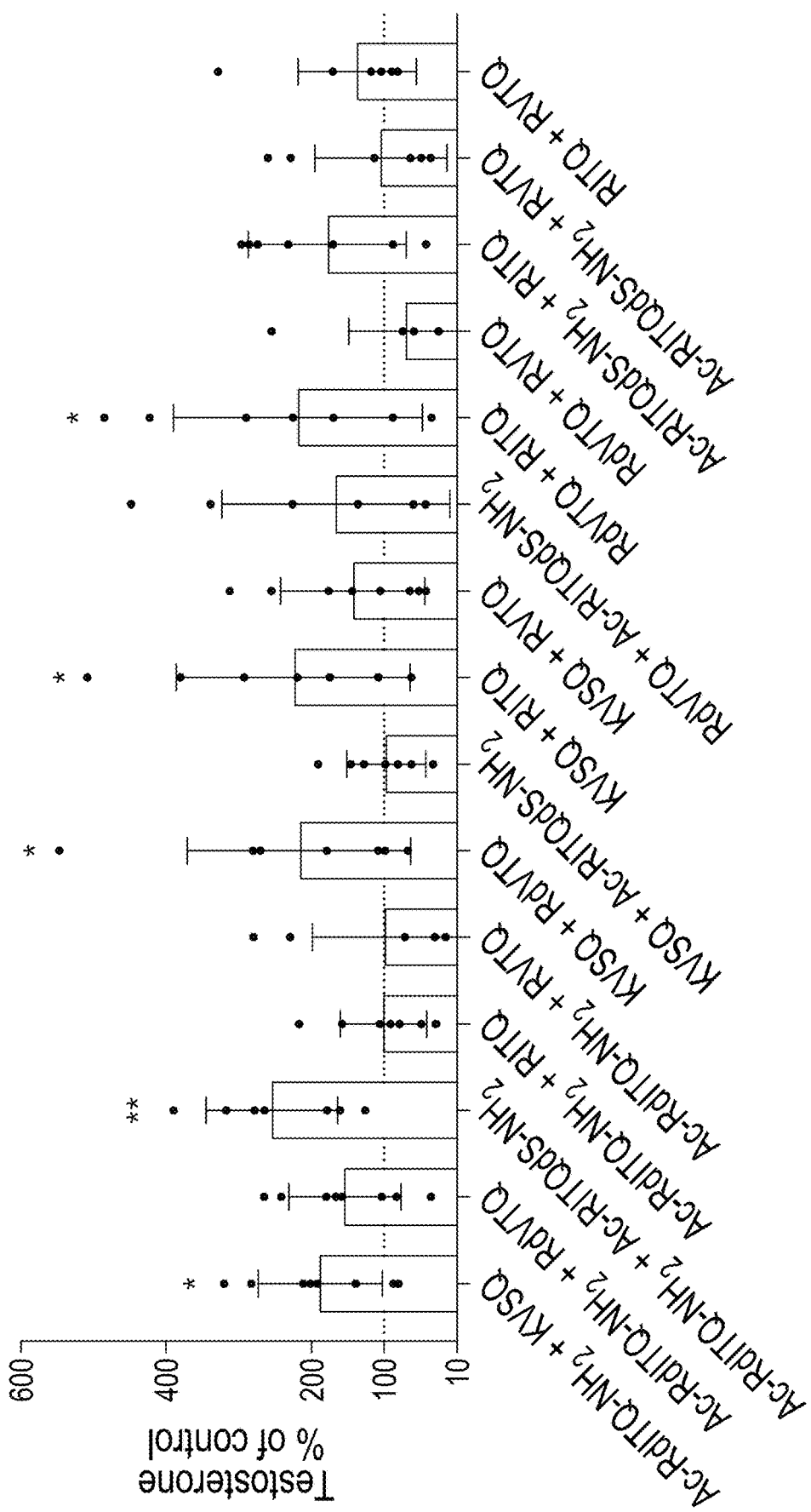

Mix of Two Peptides at Low-Doses Increase Plasma Testosterone Levels after Oral Administration The previous results showed that some of the peptides that increased circulating testosterone levels at ~420 µg/kg had a biphasic profile characterized by repression of testosterone levels around the 220 µg/kg dose. The results also showed that the 10 µg/kg dose increased, although not significantly, average testosterone levels of 6 peptides (FIG. 5). It was hypothesized that a mix of two peptides may result in significant increases in testosterone levels, thereby avoiding potential negative effects observed in some of the peptides. To test this hypothesis, Brown-Norway rats aged 91-134 days old were treated with the possible 15 permutations generated from the mix of 6 candidate peptides dosed at 10 µg/kg each. The results show that 5 dual-peptide combinations showed significant increases in testosterone levels (FIGS. 6A, C-F) with the rest showing no changes in testosterone levels (FIGS. 12A-I). FIG. 6G summarizes the peptide treatment data normalized to their respective control testosterone levels and presented in the ordered tested.

Modification to the Core Peptide Increase the Half-Life in Serum

Figure 7:
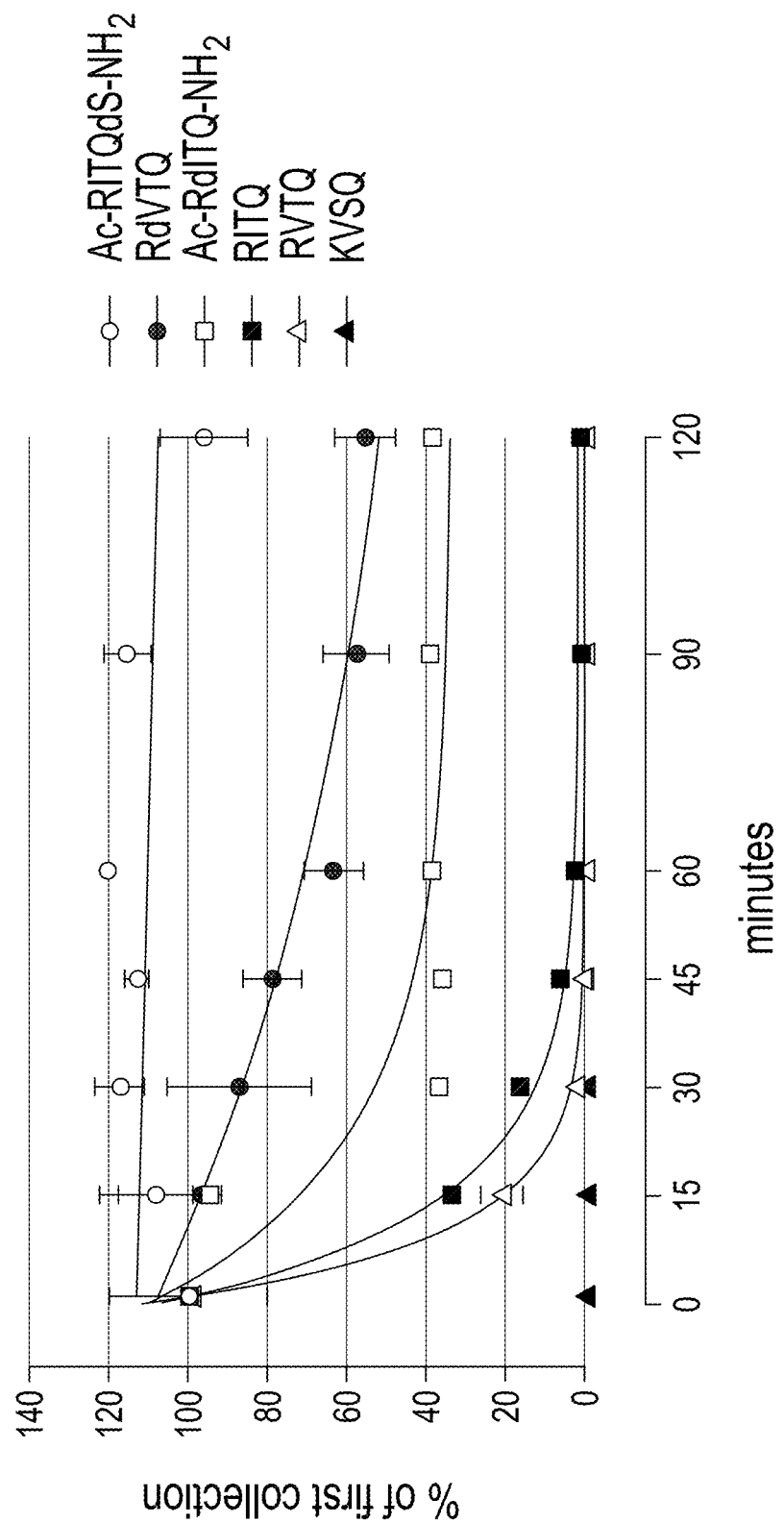
FIG. 7 shows that modifications to the peptide cores increase plasma stability. Results are shown as the % of peptide levels with respect to the first time point (1 min). N=3; results shown as mean±SEM.

To ascertain the stability of the leading candidate peptides in plasma, 4 µM of all peptides, except for KVSQ where we incubated with 12.5 µM, were incubated in 100 µL of plasma. The results showed that the half-life of the various peptides was as follows Ac-RITQdS-NH$_2$>RdVTQ>Ac-RdITQ-NH$_2$>RITQ>RVTQ>KVSQ (FIG. 7). As expected, peptide modification with end-capping or the introduction of D-amino acids had the longest half-life, while peptides that included K exhibited the fastest degradation.

Figure 8A:
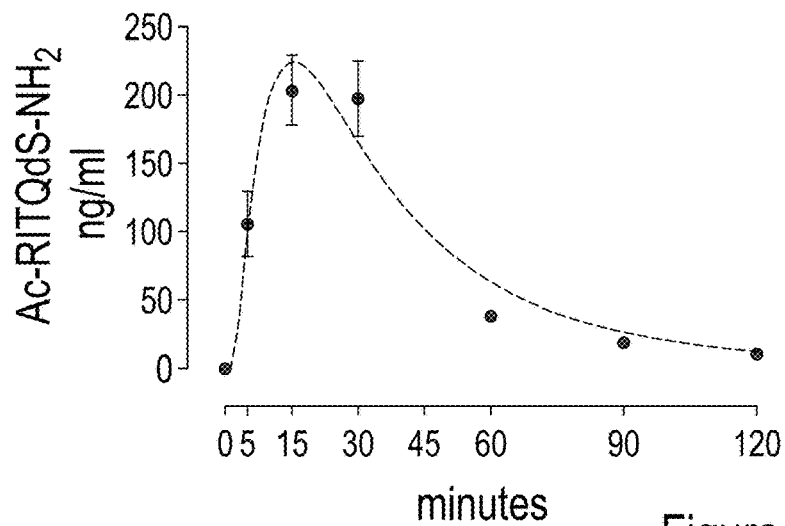
FIGS. 8A to 8C show the pharmacokinetics after single oral dose of selected peptides.
Figure 8B:
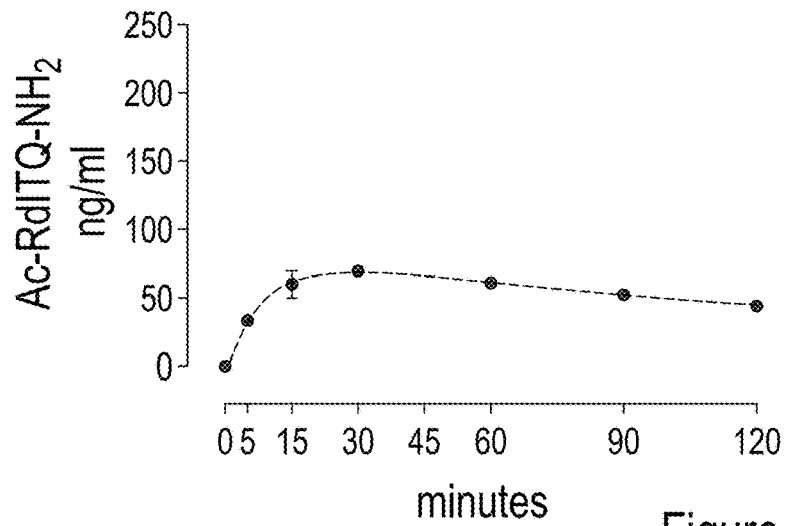
Figure 8C:
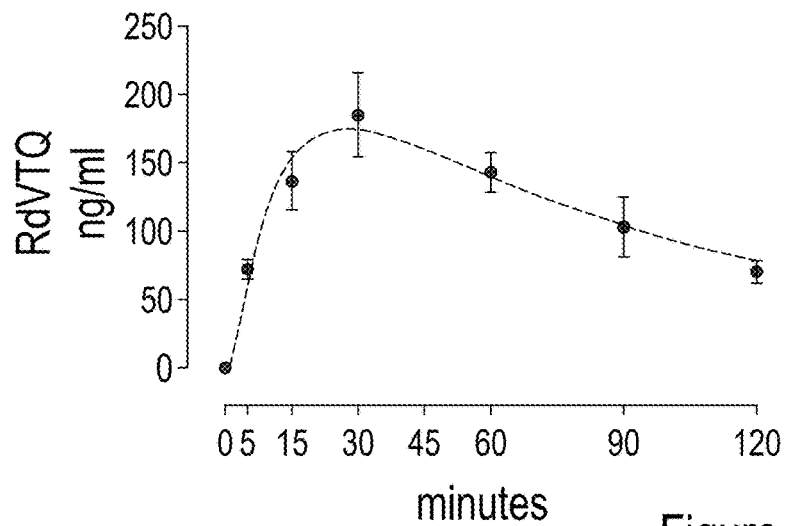
Figure 9A:
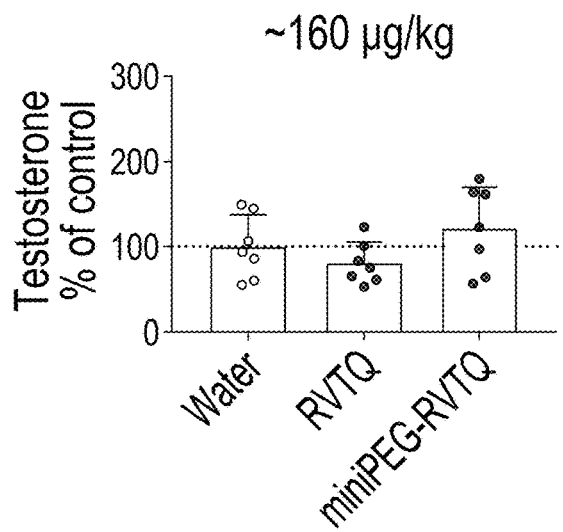
FIGS. 9A to 9E show the modifications to the RVTQ (SEQ ID NO: 2) core that did not increase plasma testosterone levels after oral administration. Results are shown as the plasma testosterone levels in Brown-Norway rats 3 hrs after gavage with water, RVTQ (SEQ ID NO: 2) or the various core modifications.
Figure 9B:
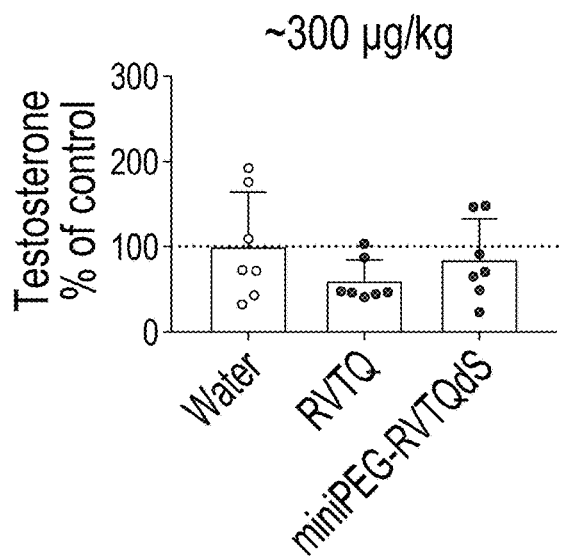
Figure 9C:
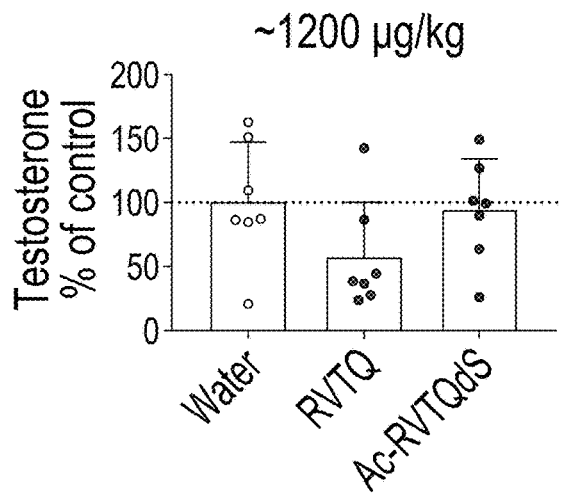
Figure 9D:
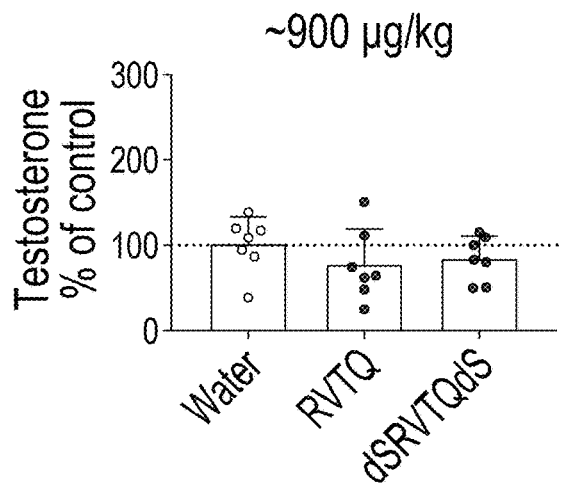
Figure 9E:
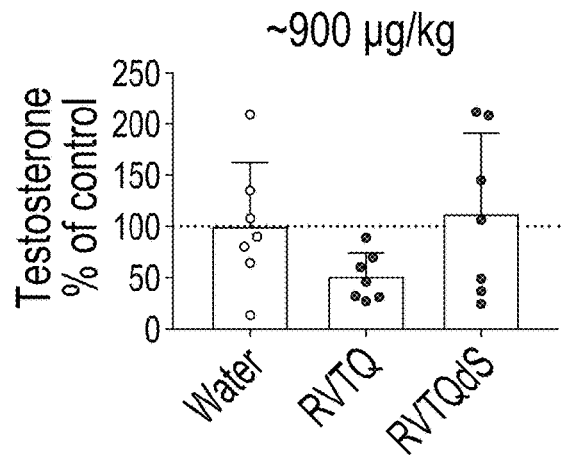

The pharmacokinetic characterization of Ac-RITQdS-NH$_2$, RdVTQ, Ac-RdITQ-NH$_2$, RVTQ, and KVSQ was further analyzed in vivo. The results show that most of the peptides reach peak concentrations in the blood within 15 to 30 minutes ranging from 70 to 230 ng/ml (FIGS. 8A-C). The naked RVTQ and KVSQ cores were not detected (data not shown).

It was first shown that subcutaneous delivery of RVTQ (N163-166) was active in Brown-Norway rats. We found a significant ~two-fold increase in plasma testosterone levels in ~54 day-old Brown-Norway rats. We then used an evolutionary approach to study whether substitutions with related amino acids to the RVTQ core retained steroidogenic activity. Sequence analysis of all VDAC1 entries found in the UniProt portal identified RITQ, KITQ, and RVSQ as core-variations. These substitutions were of structurally related amino acids. The data showed that infusion of RITQ and KITQ significantly increased testosterone levels, indicating that changes to the protein core were feasible. Interestingly, in our first round of measurements, RITQ showed a non-significant increase that became significant during our second round of measurements. The suppression of the peptide activity by the HPG axis is a unique "safety feature" that may prevent prolonged periods of supraphysiological testosterone levels.

Small molecule derivatives of the RVTQ core were designed by introducing modifications known to increase the half-life of proteins. It was sought to increase the half-life because rapid peptide degradation is the main challenge for the use of peptides as oral therapeutics. To screen for oral candidates, an animal model was developed where Brown-Norway rats were gavaged with the various RVTQ core modifications followed by percutaneous jugular blood sampling. The native RVTQ sequence was used as a control and administered the modified core derivatives using arbitrary doses. Blood collection was also arbitrarily set at three hours post-gavage to account for the absorption of the peptide and the time Leydig cells take to increase androgen production. The data showed that addition of a D-serine and capping of the carboxy terminus with NH$_2$ resulted in a significant increase in testosterone levels. This finding was confirmed in two follow up experiments that characterized the best sampling time point, which was stablished at 2 hrs post-gavage with ~580 µg/kg of RVTQdS-NH$_2$. The data indicated that RVTQdS-NH$_2$ was rapidly absorbed and that the peptide reached, in sufficient quantities, the Leydig cells to efficiently increase steroidogenesis. Moreover, these findings were substantial since an increase in steroid levels during a 2 to 3 hrs window is likely to escape HPG repression and allow for multiple dosing. This peptide's kinetics also favor the development of a dose-regimen that mimics the physiological peaks in testosterone production found at specific times of the day. Additionally, the oral route offers the best penitent compliance and permits dosing flexibility.

Brown-Norway rats were then used to test various peptides and established blood collections at 2 hrs post-gavage with peptide dosing that ranged from an average of 530 to 620 µg/kg. This screening included molecules with amino acid modifications to the RVTQ core where the R was substituted with K, V was substituted with I or L, T was substituted with S, and Q was substituted with E. These amino acid modifications generated 10 core sequences that, when combined with D-amino acids, capping of the peptide ends, and use of mini-PEG, generated 34 candidate small molecules. This screening identified 11 small molecules that significantly increased testosterone levels. To confirm that the effects were still present at the end of our screening, we treated the rats at the end of the experiment with RITQ, the first molecule identified, and observed significant increases in testosterone. Moreover, this screening started when the rats were ~60 days-old; however, the data showed that ~80-90 day-old rats were a better starting point, since younger rats exhibit higher testosterone levels that may mask the peptide effect. It was surprising to note by the range of amino acid changes and protein modifications that increased testosterone levels, which included the unmodified cores RITQ, KVSQ, RISQ, KITQ, RVSQ, and SRVTQ (underlined letters denote amino acid changes from the original RVTQ (SEQ ID NO: 2) core). In general, modifications to V were the most permissive except for L where the additional carbon may have resulted in steric interference. The data also suggested that Q was essential since any substitution abolished peptide activity. This agreed with the initial evolutionary-guided analysis showing conservation of Q among all the sequences processed (FIG. 1B). Several other peptides were identified that showed a non-significant trend to increase testosterone levels and hypothesized that some of these peptides might be active if the dosing was adjusted. Moreover, several other peptides were identified with a non-significant trend to decrease testosterone levels that might indicate a dose-dependent repression state.

Dose-response experiments were carried using RdVTQ, which showed the best performance, and RITQ that showed the second-best statistical significance. The results indicated that RdVTQ increased the average testosterone levels at all doses tested, reaching significance at doses above 400 µg/kg.

RITQ showed a biphasic response with testosterone levels significantly rising at 10 and 510 µg/kg and a non-significant decrease ~210 µg/kg. Interestingly, RdVTQ also showed a trend to increase at the low ~10 µg/kg dose, followed by a slight decline in testosterone levels. It is important to note that testosterone levels were taken 2 hrs after gavage and that integration of the area under the curve for each rat during the 3 hrs when testosterone levels increase is likely to show significant increases. Together, the results suggested that the intracellular mechanism triggered by the administration of the peptides may have self-regulatory states resulting in the biphasic effect shown. These dose-response experiments also showed that the tested small molecules did not affect adrenal steroidogenesis since corticosterone levels did not significantly change.

Identification of the peptides that robustly increased testosterone levels across the doses where the biphasic effect of RITQ was identified was then pursued. The testing conditions were improved by using rats older than 80 days, collecting blood samples 2 hrs after gavage, and dosing at ~10, 220, and 420 µg peptide/day. Eleven (11) molecules that significantly increased testosterone, including Ac-RITQdS-NH$_2$, the first peptide excluded from the inclusion criteria but that showed a trend to increase testosterone levels were tested. This screening identified Ac-RITQdS-NH$_2$, KVSQ, RdVTQ, and Ac-RdITQ-NH$_2$ as those peptides that consistently increased testosterone levels across the doses tested. Several other peptides were identified that showed a decrease in steroid levels at ~220 µg/kg, which included RITQ, in agreement with the first observation of the biphasic effect. In summary, this third screening identified 4 peptides with robust profiles and, in addition, the data showed that dosing at ~10 µg/kg increased, although not significantly, the average testosterone levels of Ac-RITQdS-NH$_2$, RdVTQ, Ac-RdITQ-NH$_2$, RITQ, KVSQ, and Ac-KdITQ-NH$_2$.

It was then sought to improve the efficiency of selected peptides to decrease dosage used while increasing safety margins. A combination of two of the 6 peptides, which due to their modifications may have different pharmacokinetic profiles, was tested to determine if they could act together to exhibit significant effects. The peptides Ac-RITQdS-NH$_2$, KVSQ, RdVTQ, Ac-RdITQ-NH$_2$, RITQ, and the original RVTQ core tetrapeptide were specifically selected. Permutation of these 6 small molecules, composed of 3 native and 3 modified cores, resulted in 15 possible 2-peptide combinations that were tested. The testing conditions were set as follows: Brown-Norway rats age >90 days old, blood collection 2 hrs after gavage, and used 10 µg/kg each of the 2 peptides tested. The results identified 5 combinations that significantly increased testosterone levels. This finding was significant since it improved dosing 55-fold from our first and second screenings set at ~550 µg/kg. The very low doses used in the oral 2-peptide mixes are likely to avoid side effects, be cleared rapidly, facilitate repetitive dosing, and decrease manufacturing costs.

The pharmacokinetic profile of 6 leading peptides was characterized in plasma and in vivo. The data showed that Ac-RITQdS-NH$_2$ was the most stable peptide, followed by RdVTQ and Ac-RdITQ-NH$_2$. The unmodified core tetrapeptides RITQ and RVTQ showed a rapid time-dependent degradation. Data for KVSQ, for which the input peptide was 4-times greater than all other peptides tested, indicated that presence of lysine significantly increased peptide degradation in the in vitro assay. The pharmacokinetic profile of these drugs was characterized in vivo. The data showed that most peptides reached peak concentrations 15-30 min post-gavage with Ac-RITQdS-NH$_2$ being the fastest absorbed in ~15 min. These data, which showed rapid abortion of the peptides, is in agreement with the finding that testosterone levels reached peak induction levels at 2 hrs. Moreover, the rapid degradation of KVSQ in the in vitro and in vivo assays is surprising since this tetrapeptide seems to activate steroidogenesis consistently. The bioactivity and rapid degradation of KVSQ suggest that only few molecules are needed to activate the molecular target and elicit effects.

Example II—TV159-172 Derivatives Modulate Testosterone Levels

Peptides. Peptides were obtained from CanPeptide (Montreal, Quebec) with >95% purity. All peptides were dissolved in molecular grade double distilled water to obtain a 1 mM stock solution and stored at −20° C.

Animal handling, serum, plasma, and intratesticular sample collection. Brown-Norway rats aged 36-42 days old were purchased from Charles River and aged until ~60 days old. Rats were kept on a 12 L/12 D day cycle with lights on at 7 AM and had access to food and water ad libitum.

Jugular samples were collected via percutaneous puncture and samples were collected in EDTA coated tubes (plasma) and centrifuged at 1,300 RCF for 10 min and stored in 2 mL Wheaton glass vials (Fisher Scientific, Hampton, NH, Cat #03 337 21A) and kept at −20° C. Animals were handled according to protocols approved by the McGill University Animal Care and Use Committee, which included standard operating procedures for the amount and frequency of blood sample collections.

Hormone measurements. Testosterone levels were measured using Cayman (Ann Arbor, MI) EIA kit Cat #582701 and corticosterone levels were measured using Cayman EIA kit Cat #501320. Plasma fluid samples were diluted until controls fitted the middle of the standard curve used.

Osmotic pumps. Alzet 2006 osmotic pumps were purchased from Alzet (Cupertino, CA) with an infusion rate of 0.15 µL/hr. The peptide concentration loaded into the pumps accounted for weight gain at the time of collection and was adjusted to deliver the doses indicated in each figure. The pump infusion rates varied by production lot and were adjusted accordingly. Pumps were loaded under sterile conditions 24 hr before surgical implantation and were kept at 37° C. in PBS until their use.

Surgical procedures. Infusion pumps were implanted in the interscapular region under general anesthesia following antisepsis using iodine. The surgical wound was closed with staples that were removed a week after the surgery. Carprofen (Zoetis, Parsippany, NJ) was given before the surgical procedure and for two days after for pain management.

Statistical analysis. GraphPad Prism 7.03 (GraphPad Software, La Jolla, CA) and Excel 2006 (Microsoft Corporation, Redmond, WA) were used to generate graphs, linear regressions, and statistical analysis. ANOVA or a one tail t-test was used to determine significant changes. The number of animals used per experiment is given in each of the corresponding figure legends. Data are shown as means±standard deviation unless otherwise specified in the figure legend.

Shorter Derivatives of TV159-172 are Bioactive in Inducing Steroid Formation

Figure 13B:
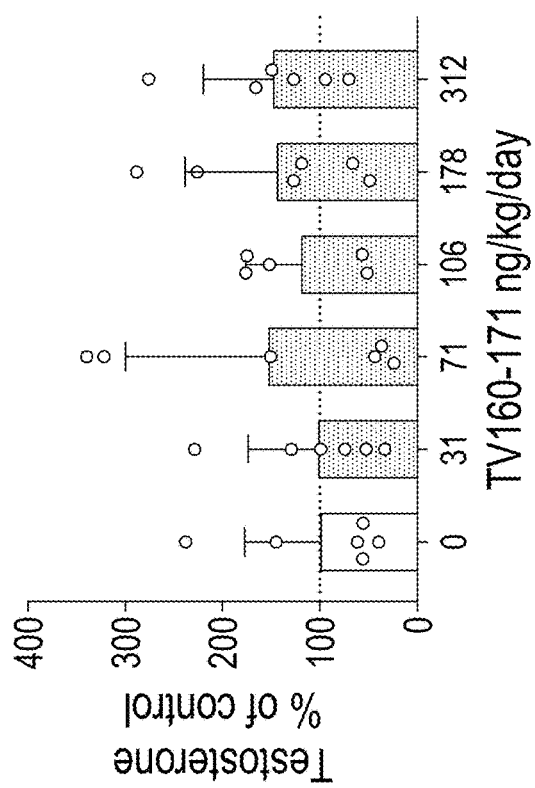
FIGS. 13A to 13J show that various deletions of TV159-172 retain androgenic activity.
Figure 13D:
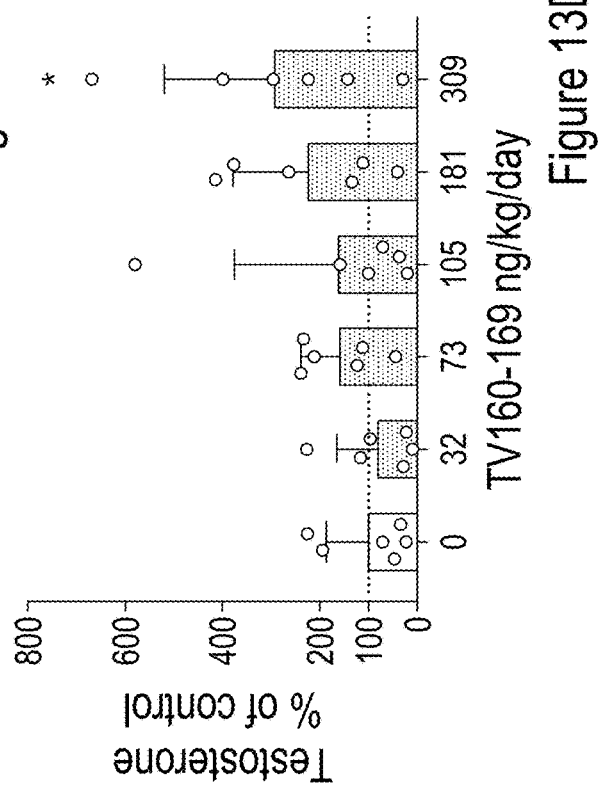
Figure 13A:
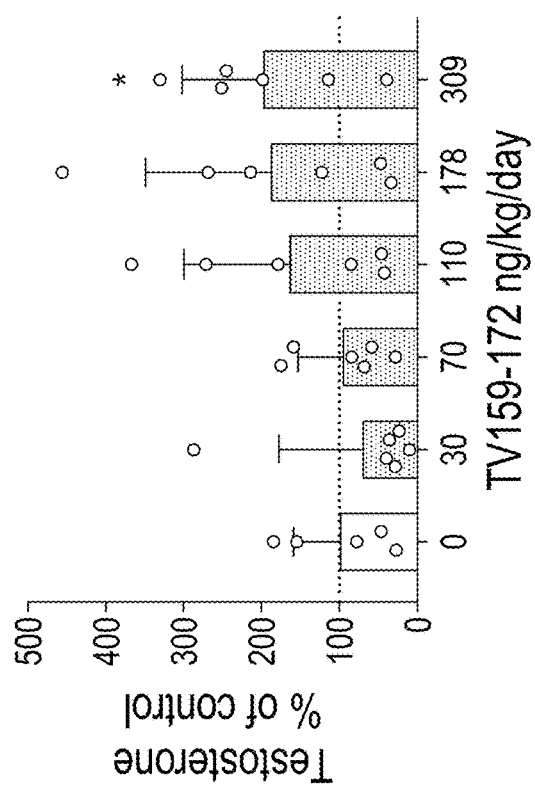
Figure 13C:
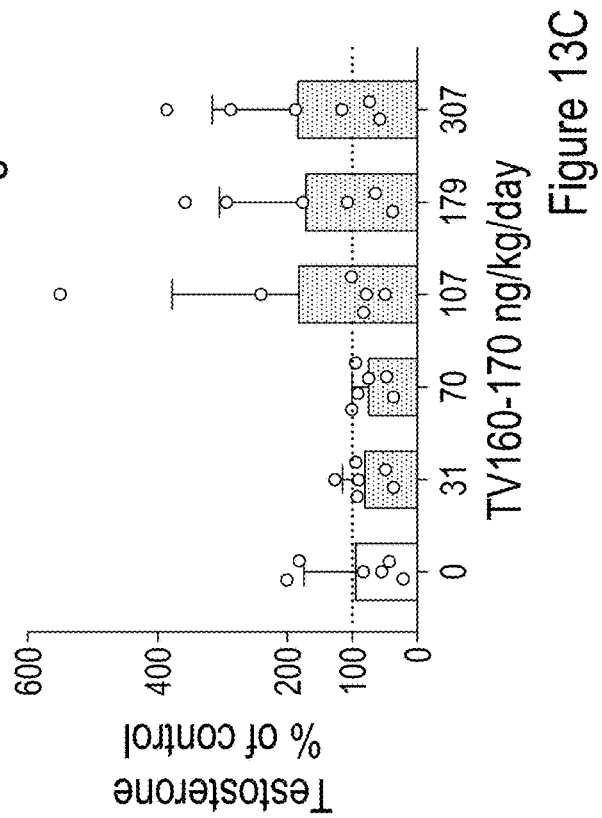
Figure 13F:
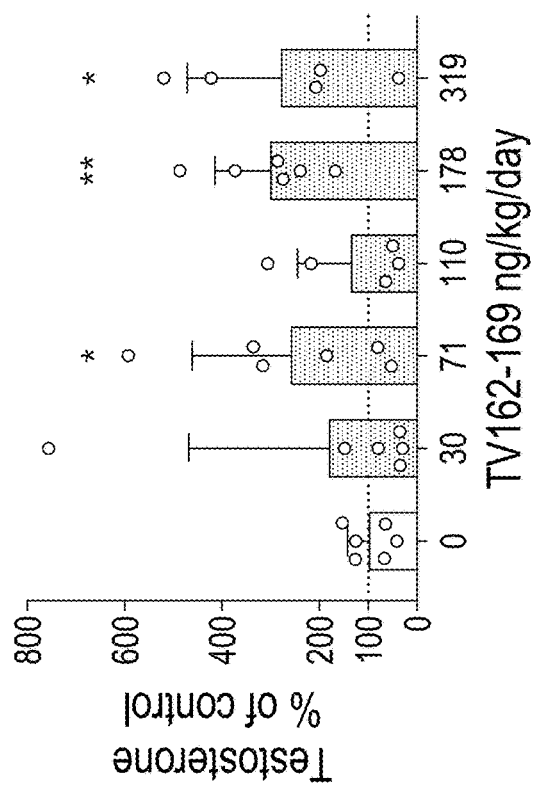
Figure 13H:
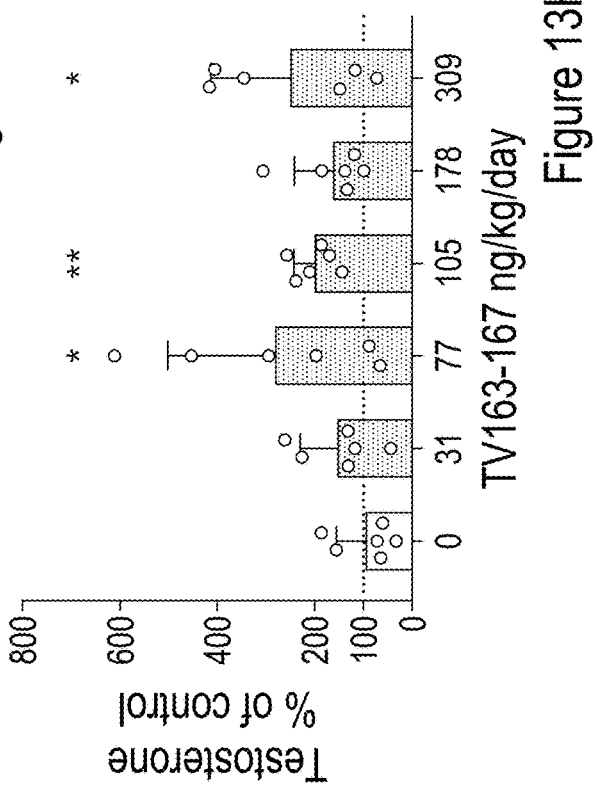
Figure 13E:
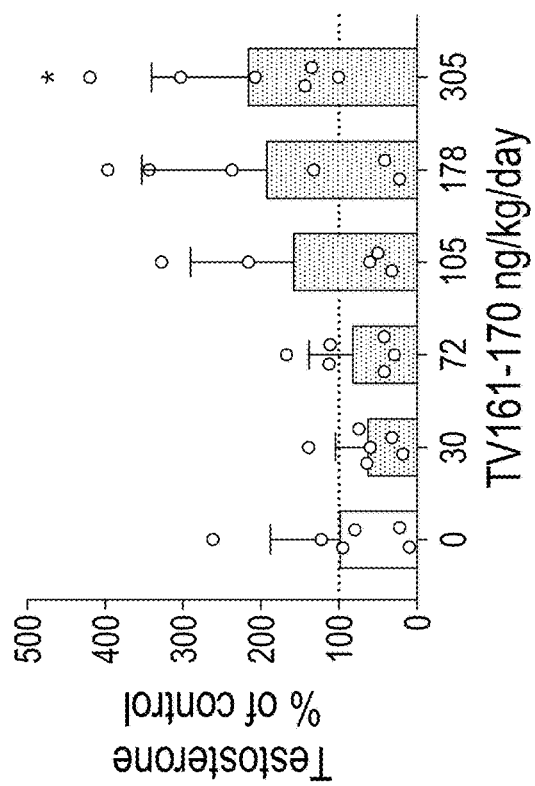
Figure 13G:
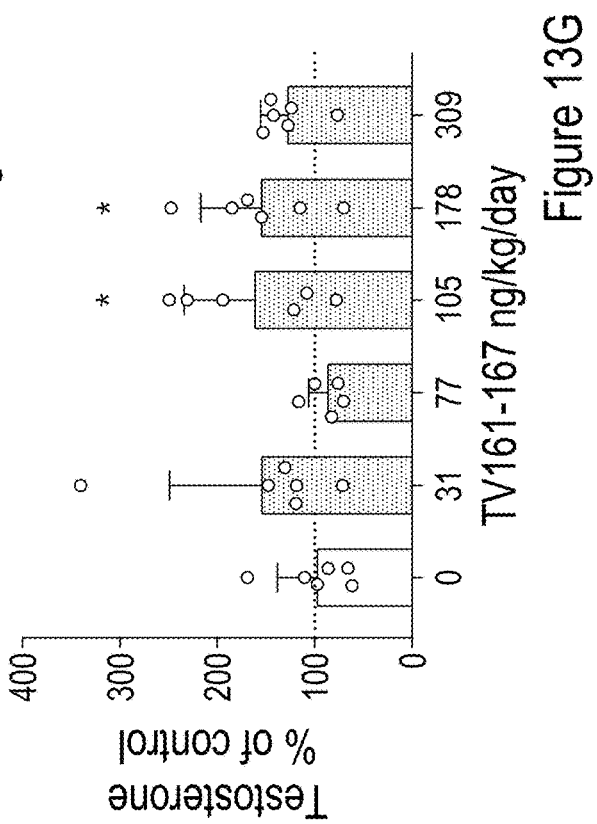
Figure 13J:
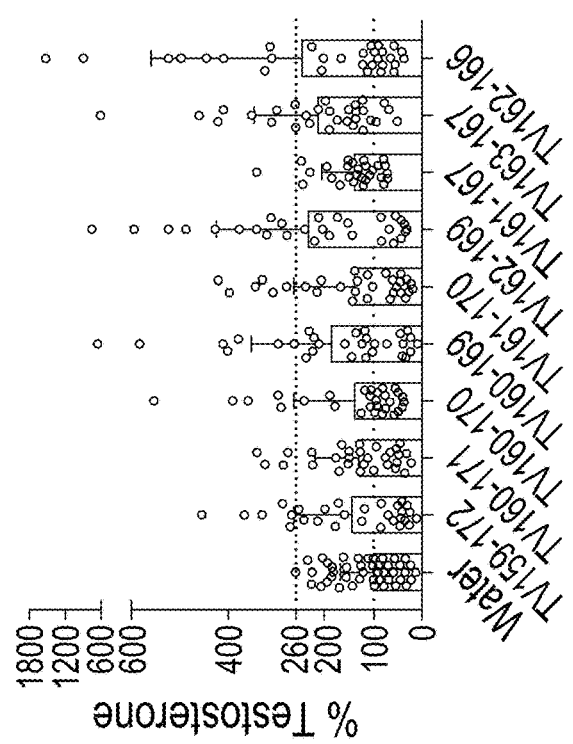
Figure 13I:
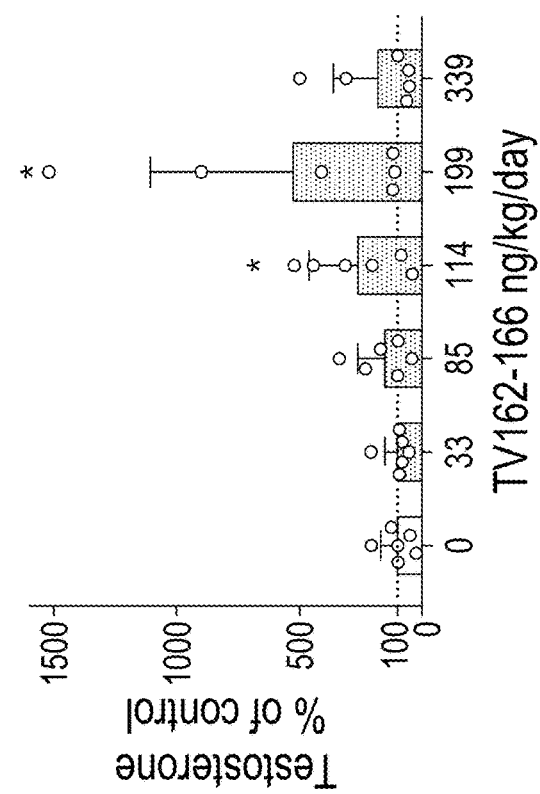
Figure 14I:
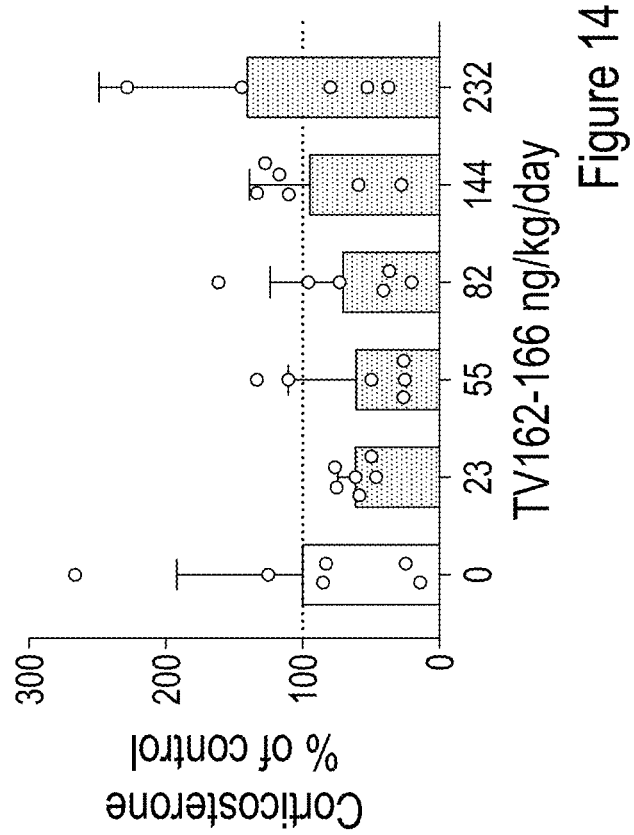

Various experimental groups of Brown-Norway rats were implanted with subcutaneous pumps delivering increasing doses of TV-peptides for 42 days. Progressive single amino acid deletions was conducted from the N- and C-terminus until arriving at the shortest, TV163-167 and TV162-166, peptides that contained 5 amino acids from the original 14 amino acid VDAC1-derived sequence contained in TV159-172. Testosterone measurements in blood plasma collected 1 week after implantation showed significant increases in testosterone levels in TV156-172, TV160-169, TV161-170, TV162-169, TV161-167, TV162-166 (FIGS. 13A-13I). Pooling of all control data and from all rats treated with TV-peptides, independent of the dose, showed an increased dispersion in all the TV-peptides (FIG. 13J). The pooled results show that while the highest control reached 2.6 times those of the control average, rats receiving TV-peptides often had levels higher than 2.6-fold and, in some cases, upwards of 4 times those of control averages.

Plasma corticosterone levels collected around infusion day 40 were significantly increased by exposure to TV160-171, TV160-170, and TV162-169, but significantly decreased in response to TV161-167 treatment (FIGS. 14A-14I).

The Tetrapeptide N163-166 Increases Testosterone Levels

The deletion experiments showed that the shorter TV163-167 and TV162-166 peptides were steroidogenically active. FIG. 15A shows that TV163-167 and TV162-166 overlap at amino acids 163-166 whose RVTQ sequence corresponds to the weight of a small molecule of 503 Daltons. Brown-Norway rats were subcutaneously implanted with increasing concentrations of N163-166, where the N denotes the "naked" and TAT-less feature of this molecule. Testosterone and corticosterone levels were measured 7 and 40 days after implantation, respectively. The results obtained show that N163-166 significantly increased testosterone levels at 309 ng/kg/day (FIG. 15B). Corticosterone levels were not affected by the treatment inducing testosterone formation and decreased at the lower 23 ng/kg/day tetrapeptide N163-166 dose (FIG. 15C).

The identification of the minimal bioactive sequence in the identified TV peptides was sought, which are based on VDAC1 sequence. Brown-Norway rats were used to find the bioactive core in the TV159-172 sequence that retains steroid activity. The progressive deletions of the TV159-172 sequence showed that steroidogenic activity can be maintained with a short 5 amino acid sequence. The testosterone levels data induced by the various peptides were pooled, independent of the dose used, to identify the overall activity of the TV deletions. The pooled analysis of control rats composed of 60 samples yielded a rat with 2.6 times the pooled control average as the control rat with the highest testosterone levels. In contrast, all peptides tested had several rats with testosterone levels beyond the highest control rat, with some rats reaching upwards of 5-fold increase above the pooled control average. While the pooled results were not meant to be used for statistical analysis, they showed segregation of rats (i.e. TV160-169 and TV162-169) into low and high levels responders, suggesting that some rats reach testosterone levels that triggered modulation by HPG axis. Testosterone levels have circadian and seasonal changes, and the effect of these factors on TV peptide action remains to be studied. Together, the results show that shorter sequences derived from TV159-172 are active in stimulating Leydig cell testosterone biosynthesis.

Measurement of plasma corticosterone levels in the same Brown-Norway rats treated with the various peptides showed peptide-specific activity. The longer TV160-171, TV160-170, and TV162-169 peptides promoted significant increases in plasma corticosterone levels, while the shortest TV163-167 and TV162-166 showed no significant changes. Some corticosterone levels, like those seen in TV160-170, were higher than those seen in testosterone measurements and were upwards of 15 times those of the control average. These results suggested that some rats showed very high corticosterone levels because, unlike testosterone, corticosterone is not as tightly regulated. It is important to note that the percutaneous collection of the blood samples was not the optimal method to evaluate adrenal effects. This is because the collection process affects the stress levels and, consequentially, corticosterone release in these rats. Despite this, the effects observed in TV160-171 and TV160-170 show a dose-response effect. In summary, the data obtained suggest that the length of the TV159-172-derived sequences had differential effects on testicular vs adrenal-made steroids, with longer sequences favoring corticosterone production while shorter sequences targeting Leydig cell testosterone biosynthesis.

Since the shorter TV163-167 and TV162-166 peptides showed androgenic activity and diminished corticosterone induction, we wondered if the RVTQ sequence, which corresponds to shared amino acids 163-166, had steroidogenic effects. The results obtained using the same subcutaneous infusion model showed that N163-166 is bioactive. A significant increase in plasma testosterone but no changes in corticosterone levels at the highest dose tested, and a significant decrease in corticosterone levels at the lowest dose tested was observed.

In summary, N163-166 increased testosterone production while not affecting adrenal steroidogenesis. Subcutaneous infusion of TV- and N (naked)-peptides reached the Leydig cells, as indicated by testosterone production, with sufficient levels despite the various compartments crossed by the peptides. While subcutaneous infusion is feasible for therapeutic purposes, here, it was used as means to aid in the development of the original TV159-172 peptide. The finding that the core N163-166 is bioactive will significantly aid in the development of this molecule as a therapeutic and methods of therapeutic delivery to selectively increase androgen levels.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Aghazadeh, Y., et al., Induction of Androgen Formation in the Male by a TAT-VDAC1 Fusion Peptide Blocking 14-3-3varepsilon Protein Adaptor and Mitochondrial VDAC1 Interactions. Mol Ther, 2014. 22(10): p. 1779-91.

What is claimed is:

1. An isolated peptide consisting of formula I:

$$\text{A-Xaa}_1\text{-Xaa}_2\text{-Xaa}_3\text{-Xaa}_4\text{-Xaa}_5\text{-Xaa}_6\text{-Xaa}_7\text{-Xaa}_8\text{-B}$$ (I)

wherein:
A is present or absent and is a moiety improving the circulation half-life of the isolated peptide;
$Xaa_1$ is present or absent, when present $Xaa_1$ is a L- or D-amino acid residue;
$Xaa_2$ is present or absent, when present $Xaa_2$ is a L-serine or D-serine;
$Xaa_3$ is a L-lysine, a D-lysine, a L-arginine or a D-arginine;
$Xaa_4$ is a L-valine, a D-valine, a L-isoleucine, a D-isoleucine, a L-leucine, a D-leucine, a glycine, a D-alanine or a L-alanine;
$Xaa_5$ is a L-serine, a D-serine, a L-threonine or a D-threonine;
$Xaa_6$ is a L-glutamine, a D-glutamine, a L-glutamic acid or a D-glutamic acid;
$Xaa_7$ is present or absent, when present $Xaa_7$ is a L-serine or a D-serine;
$Xaa_8$ is present or absent, when present $Xaa_8$ is a L- or D-amino acid residue; and
B is present or absent and is a moiety improving the circulation half-life of the isolated peptide, wherein A and B are not a peptide.

2. The isolated peptide of claim 1 in which $Xaa_1$ is absent and/or $Xaa_2$ is absent.

3. The isolated peptide of claim 1, in which $Xaa_3$-$Xaa_4$-$Xaa_5$-$Xaa_6$-$Xaa_7$ has the amino acid sequence of SEQ ID NO: 1, 2, 3, 4, 5, 6, 7, 8, 9, 10, 11, 12, 13, 14, 15, 16, 18, 19, 20, 21, 22 or 23.

4. The isolated peptide of claim 1, in which $Xaa_2$-$Xaa_3$-$Xaa_4$-$Xaa_5$-$Xaa_6$-$Xaa_7$ has the amino acid sequence of SEQ ID NO: 16 or 23.

5. The isolated peptide of claim 1, in which $Xaa_3$ is L- or D-lysine.

6. The isolated peptide of claim 1, in which $Xaa_3$ is L- or D-arginine.

7. The isolated peptide of claim 1, in which $Xaa_4$ is L-valine or D-valine.

8. The isolated peptide of claim 1, in which $Xaa_4$ is L-isoleucine or D-isoleucine.

9. The isolated peptide of claim 1, in which $Xaa_4$ is L-leucine or D-leucine.

10. The isolated peptide of claim 1, in which $Xaa_5$ is L-serine or D-serine.

11. The isolated peptide of claim 1, in which $Xaa_5$ is L-threonine or D-threonine.

12. The isolated peptide of claim 1, in which $Xaa_6$ is L-glutamine or D-glutamine.

13. The isolated peptide of claim 1, in which $Xaa_6$ is L-glutamic acid or D-glutamic acid.

14. The isolated peptide of claim 1, in which $Xaa_7$ is absent.

15. The isolated peptide of claim 1, in which $Xaa_7$ is present.

16. The isolated peptide of claim 1, in which $Xaa_8$ is absent.

17. The isolated peptide of claim 1, wherein A is an acetyl cap or a polyethylene glycol.

18. The isolated peptide of claim 1, wherein B is an amide cap.

19. A peptide compound of formula II:

$$\text{A-Xaa}_1\text{-Xaa}_A\text{-Xaa}_B\text{-Xaa}_2\text{-Xaa}_3\text{-Xaa}_4\text{-Xaa}_5\text{-Xaa}_6\text{-Xaa}_7\text{-Xaa}_C\text{-Xaa}_D\text{-Xaa}_E\text{-Xaa}_8\text{-B}$$ (II)

wherein:
A is present or absent and is a moiety improving the circulation half-life of the peptide compound;
$Xaa_1$ is present or absent, when present $Xaa_1$ is a L- or D-amino acid residue;
$Xaa_A$ is present or absent, when present $Xaa_A$ is a L-serine or D-serine;
$Xaa_B$ is present or absent, when present $Xaa_B$ is a L-lysine or D-lysine;
$Xaa_2$ is present or absent, when present $Xaa_2$ is a L-serine or D-serine;
$Xaa_3$ is a L-lysine, a D-lysine, a L-arginine or a D-arginine;
$Xaa_4$ is a L-valine, a D-valine, a L-isoleucine, a D-isoleucine, a L-leucine, a D-leucine, a glycine, a D-alanine or a L-alanine;
$Xaa_5$ is a L-serine, a D-serine, a L-threonine or a D-threonine;
$Xaa_6$ is a L-glutamine, a D-glutamine, a L-glutamic acid or a D-glutamic acid;
$Xaa_7$ is present or absent, when present $Xaa_7$ is a L-serine or a D-serine;
$Xaa_C$ is present or absent, when present $Xaa_C$ is a L-asparagine or D-asparagine;

$Xaa_D$ is present or absent, when present $Xaa_D$ is a L-phenylalanine or D-phenylalanine;

$Xaa_E$ is present or absent, when present $Xaa_E$ is a L-alanine or D-alanine;

$Xaa_8$ is present or absent, when present $Xaa_8$ is a L- or D-amino acid residue; and B is present or absent and is a moiety improving the circulation half-life of the isolated peptide, wherein A and B are not a peptide.

20. A method for promoting the endogenous production of testosterone in a cell, said method comprising contacting the cell with at least one of:

the isolated peptide of claim 1 so as to promote the endogenous production of testosterone in the cell.

* * * * *